United States Patent
Bürli et al.

(10) Patent No.: US 9,371,332 B2
(45) Date of Patent: *Jun. 21, 2016

(54) PYRAZOLOPYRIDAZINES AND METHODS FOR TREATING RETINAL-DEGENERATIVE DISEASES AND HEARING LOSS ASSOCIATED WITH USHER SYNDROME

(71) Applicant: Usher III Initiative, Inc., Chicago, IL (US)

(72) Inventors: Roland Werner Bürli, Bishop's Stortford (GB); William Rameschandra Krishna Esmieu, Cambridge (GB); Christopher James Lock, Burwell (GB); Karine Fabienne Malagu, Saffron Walden (GB); Andrew Pate Owens, Huntingdon (GB); William E Harte, Moorpark, CA (US)

(73) Assignee: Usher III Initiative, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,535

(22) Filed: Jun. 5, 2015

(65) Prior Publication Data

US 2015/0265617 A1   Sep. 24, 2015

Related U.S. Application Data

(62) Division of application No. 13/791,744, filed on Mar. 8, 2013, now Pat. No. 9,227,976.

(60) Provisional application No. 61/718,611, filed on Oct. 25, 2012.

(51) Int. Cl.
*C07D 487/04* (2006.01)
*A61K 31/5025* (2006.01)

(52) U.S. Cl.
CPC .......... *C07D 487/04* (2013.01); *A61K 31/5025* (2013.01)

(58) Field of Classification Search
CPC ..... C07D 487/04; A61K 31/40; C07C 243/28
USPC .......................................... 514/250; 544/236
See application file for complete search history.

(56) References Cited

U.S. PATENT DOCUMENTS

| | | | |
|---|---|---|---|
| 7,390,808 | B2 | 6/2008 | Green et al. |
| 7,666,647 | B2 | 2/2010 | Ernst ter Haar et al. |
| 7,812,166 | B2 | 10/2010 | Dai et al. |
| 7,883,881 | B2 | 2/2011 | Ernst ter Haar et al. |
| 8,318,467 | B2 | 11/2012 | ter Haar et al. |
| 8,338,439 | B2 | 12/2012 | Singh et al. |
| 8,450,335 | B2 | 5/2013 | Singh et al. |
| 8,765,762 | B2 | 7/2014 | Bürli et al. |
| 9,079,909 | B2 * | 7/2015 | Burli ............... A61K 31/40 |
| 2008/0194562 | A1 | 8/2008 | Wyatt et al. |
| 2010/0029610 | A1 | 2/2010 | Singh et al. |
| 2013/0065879 | A1 | 3/2013 | Singh et al. |
| 2013/0065899 | A1 | 3/2013 | Singh et al. |
| 2013/0072469 | A1 | 3/2013 | Singh et al. |
| 2013/0165462 | A1 | 6/2013 | Singh et al. |
| 2013/0252936 | A1 | 9/2013 | Bürli et al. |
| 2014/0121197 | A1 | 5/2014 | Bürli et al. |
| 2015/0266812 | A1 | 9/2015 | Bürli et al. |

FOREIGN PATENT DOCUMENTS

| | | |
|---|---|---|
| JP | 2008-527031 | 7/2008 |
| JP | 2011-503103 | 1/2011 |
| WO | WO 03/080616 | 10/2003 |
| WO | WO 2006/077401 | 7/2006 |
| WO | WO 2007/075911 | 7/2007 |
| WO | WO 2009/039420 | 3/2009 |
| WO | WO 2009/062118 | 5/2009 |
| WO | WO 2010/046013 | 4/2010 |
| WO | WO 2012/148994 | 11/2012 |

OTHER PUBLICATIONS

U.S. Appl. No. 13/791,744, filed 2015.*
Supplementary European Search Report for European Application No. 12777328.1, mailed May 9, 2014.
Office Action for U.S. Appl. No. 13/791,205, mailed Aug. 6, 2014.
International Search Report and Written Opinion for International Application No. PCT/US2012/034959, mailed Sep. 21, 2012.
International Search Report and Written Opinion for International Application No. PCT/US2013/066938, mailed Jan. 30, 2014.
International Search Report and Written Opinion for International Application No. PCT/US2013/066939, mailed Mar. 5, 2014.
Office Action for U.S. Appl. No. 13/791,744, mailed Jun. 27, 2014.
Brana, M. F. et al., "Pyrazolo[3,4-c]pyridazines as Novel and Selective Inhibitors of Cyclin-Dependent Kinases," J. Med. Chem., 48(22):6843-6854 (2005).
Churcher, I., "Tau Therapeutic Strategies for the Treatment of Alzheimer's Disease," Current Topics in Medicinal Chemistry, 6(6):579-595 (2006).
El-Amraoui, A. et al., "Usher I Syndrome: unravelling the mechanisms that underlie the cohesion of the growing hair bundle in inner ear sensory cells," Journal of Cell Science, 118(20):4593-4603 (2005).
Tian, G. et al., "Clarin-1, encoded by the Usher Syndrome III causative gene, forms a membranous microdomain," The Journal of Biological Chemistry, 284(28):18980-18993 (2009).
Tretyakov, E. V. et al., "Investigations of the Richter reaction in a series of vicinal alkynylpyrazolediazonium salts," J. Chem. Soc., Perkin Trans., 1(24):3721-3726 (1999).
Tretyakov, E. V. et al., "New findings in the Richter reaction in series of vicinal alkynylpyrazolyldiazonium salts," Heterocyclic Communications, 4(6):519-524 (1998).
Vasilevsky, S. F. et al., "Cinnolines and pyrazolopyridazines. Novel synthetic and mechanistic aspects of the Richter reaction," Liebigs Ann., (5):775-779 (1995).

* cited by examiner

*Primary Examiner* — Paul V Ward
(74) *Attorney, Agent, or Firm* — Cooley LLP

(57) ABSTRACT

Compounds, compositions and methods for the treatment of retinal degenerative diseases, such as retinitis pigmentosa, Leber's congenital Amaurosis, Syndromic retinal degenerations, age-related macular degeneration and Usher Syndrome, and hearing loss associated with Usher Syndrome are described herein.

2 Claims, 1 Drawing Sheet

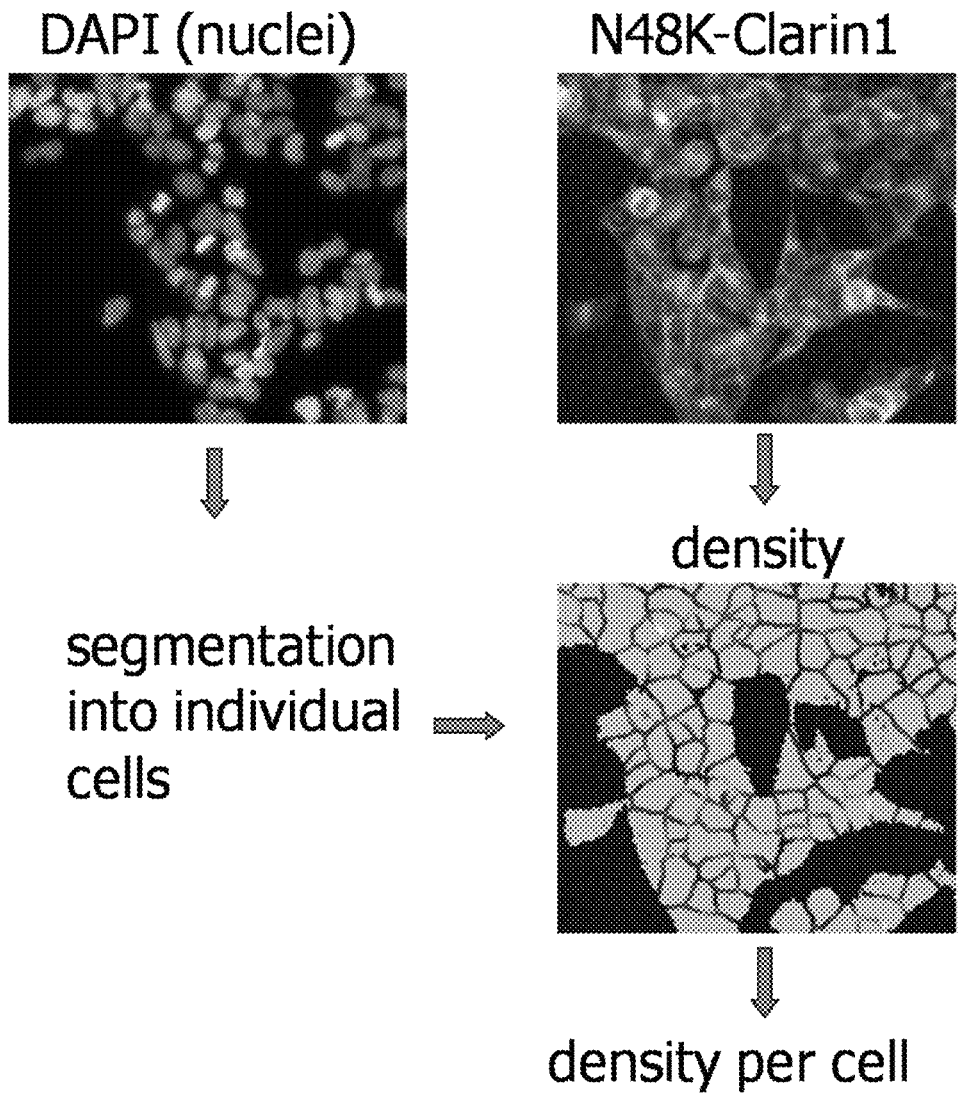
High content analysis. DAPI-stained nuclei are used to perform segmentation of the image into individual cells. The density observed in the N48K Clarin-1 channel (Cy3) is then calculated per cell and averaged over a field.

PYRAZOLOPYRIDAZINES AND METHODS FOR TREATING RETINAL-DEGENERATIVE DISEASES AND HEARING LOSS ASSOCIATED WITH USHER SYNDROME

This application is a division of U.S. application Ser. No. 13/791,744, filed Mar. 8, 2013, now U.S. Pat. No. 9,227,976, which claims the benefit of U.S. Provisional Application No. 61/718,611, filed Oct. 25, 2012, the disclosure of each of which is hereby incorporated by reference herein in its entirety.

BACKGROUND OF THE INVENTION

Usher Syndrome, a rare genetic disorder and a leading cause of deafness and blindness, is associated with a mutation in any one of ten genes. Other names for the syndrome include Hallgren Syndrome, Usher-Hallgren Syndrome, RP-Dysacusis Syndrome, and Dystrophia Retinae Dysacusis Syndrome.

Usher Syndrome is characterized by deafness and gradual vision loss. The hearing loss is associated with inner ear defects, whereas the vision loss is associated with retinitis pigmentosa (RP), a degeneration of the retinal cells. Usually, the rod cells of the retina are affected first, leading to early night blindness and the gradual loss of peripheral vision. Some cases involve early degeneration of the cone cells of the macula, leading to a loss of central acuity. In some cases, the sufferer's foveal vision is spared, leading to "doughnut vision," in which central and peripheral vision remain intact, but interrupted by a ring of blindness.

Usher Syndrome has three clinical subtypes, denoted: I, II and III. Usher I subjects are born profoundly deaf, begin to lose vision within ten years and exhibit balance difficulties. They are slow to learn to walk as children, due to vestibular abnormalities. Usher II subjects suffer lesser hearing loss, do not suffer physical imbalance and begin to lose vision in adolescence. Much of their hearing can be preserved into middle age. Usher III subjects suffer gradual loss of hearing and vision and can suffer physical imbalance.

Usher Syndrome is a variable condition; the degree of severity is not tightly linked to subtype. For example, an Usher III subject might be asymptomatic in childhood, but develop profound hearing and vision loss by early to mid adulthood. Substantial visual impairment prior to age 50 is common in Usher III subjects. An Usher I subject, on the other hand, might be deaf from birth, but sustain good central vision into old age.

SUMMARY OF THE INVENTION

The invention provides compounds of Formula I:

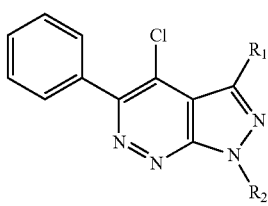

Formula I and pharmaceutically acceptable salts thereof, wherein $R_1$ is:

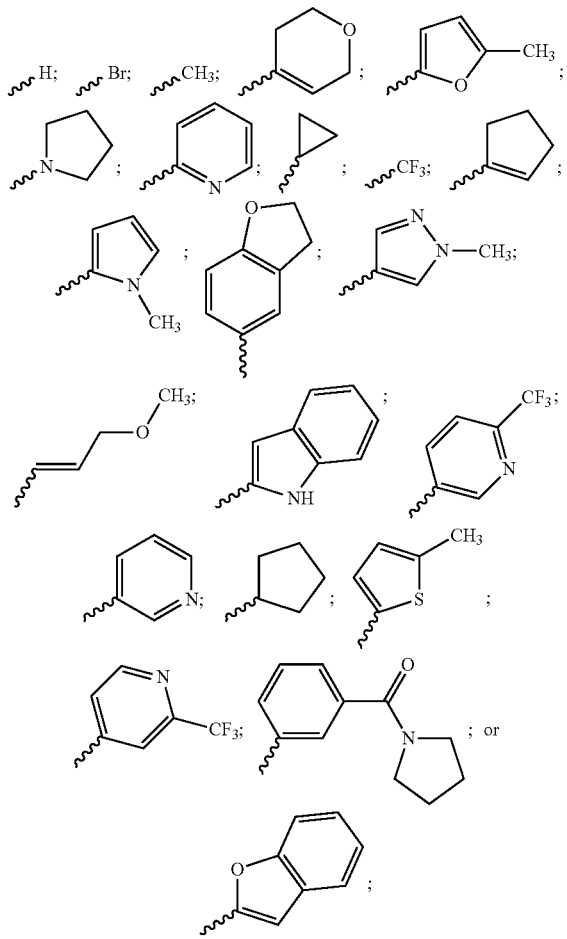

$R_2$ is:

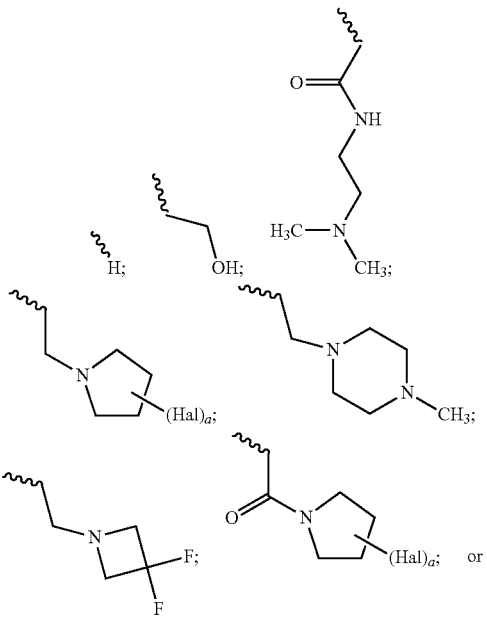

-continued

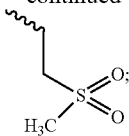

and
a is 0, 1, or 2.

The invention also provides compounds of Formula II:

Formula II

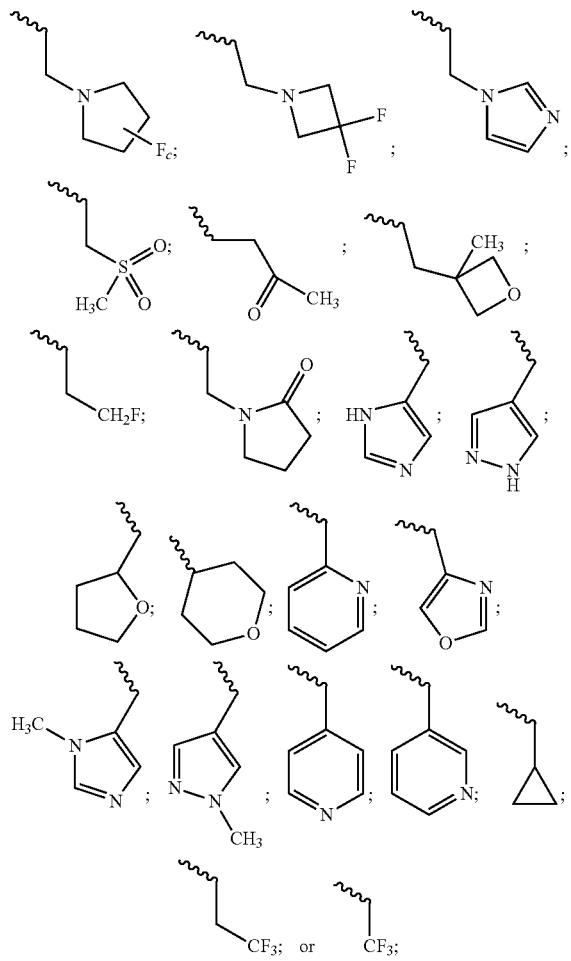

and pharmaceutically acceptable salts thereof,
wherein $R_3$ is:

b is 0 or 1; and
c is 1 or 2.

The invention additionally provides compounds of Formula III:

Formula III and pharmaceutically acceptable salts thereof,
wherein $R_4$ is

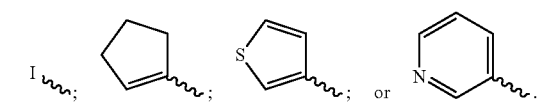

The invention further provides compounds of Formula XIII:

Formula XIII

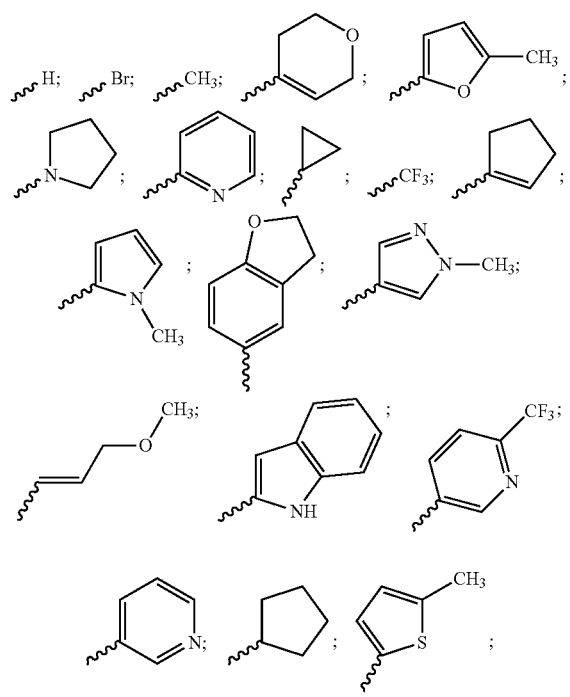

and pharmaceutically acceptable salts thereof,
wherein $R_5$ is:

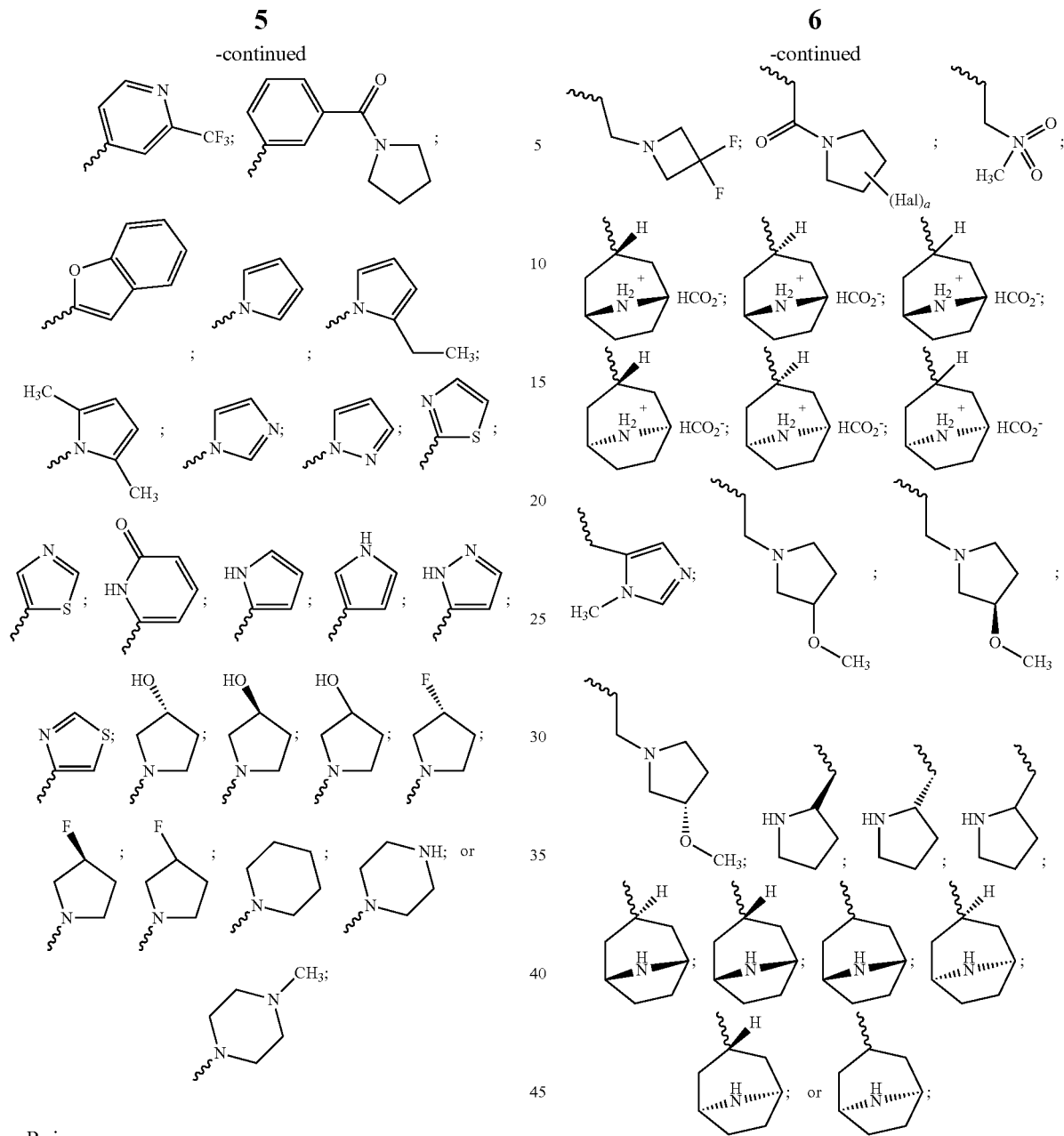
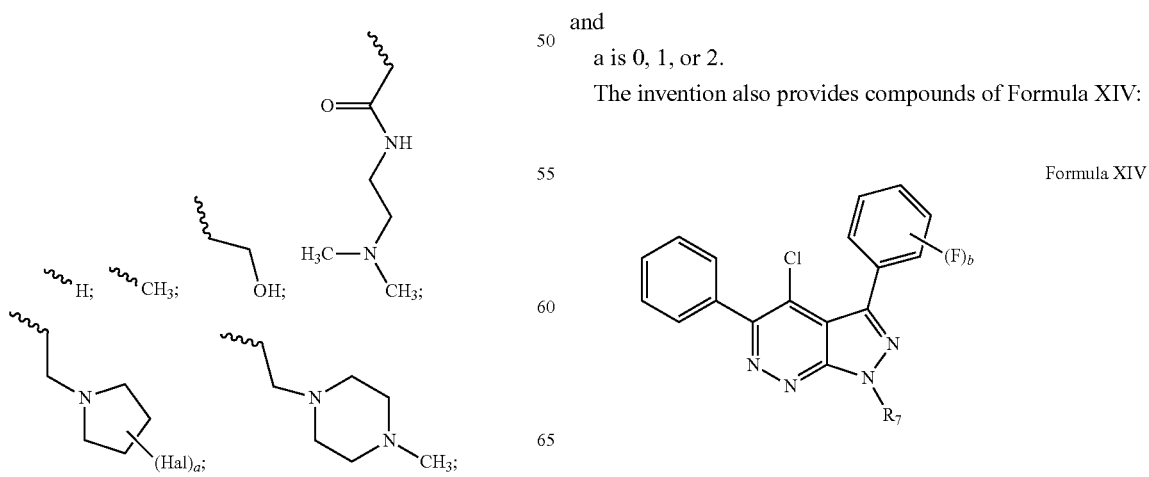
and
a is 0, 1, or 2.
The invention also provides compounds of Formula XIV:
Formula XIV
and pharmaceutically acceptable salts thereof, wherein $R_7$ is:
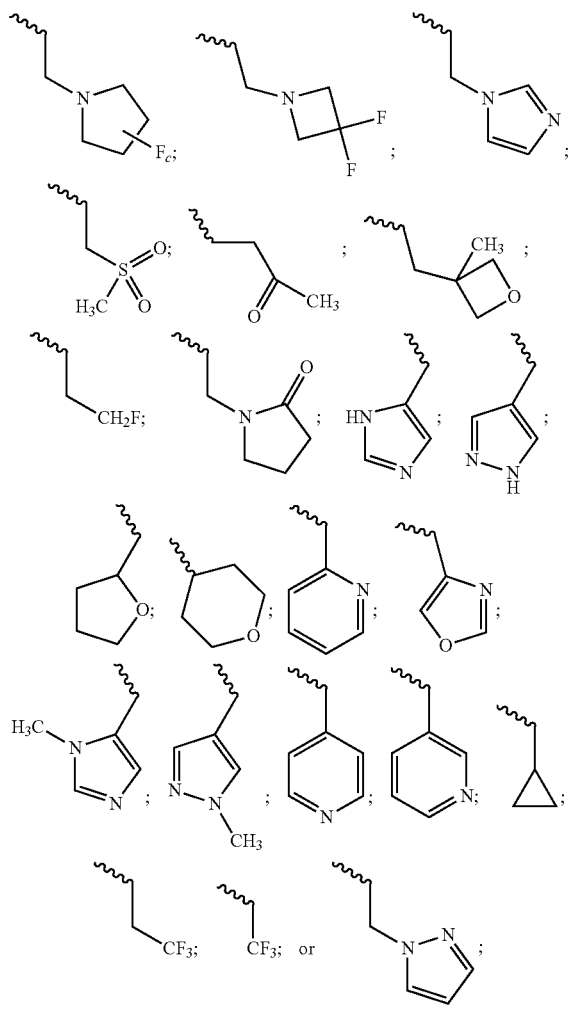
b is 0 or 1; and
c is 1 or 2.
The invention also provides compounds of Formula XV:
Formula XV
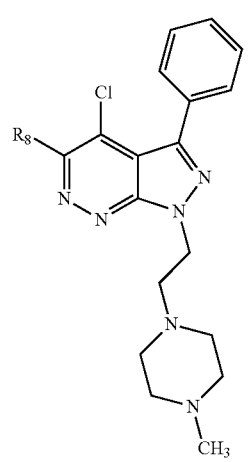
and pharmaceutically acceptable salts thereof,
wherein $R_8$ is:
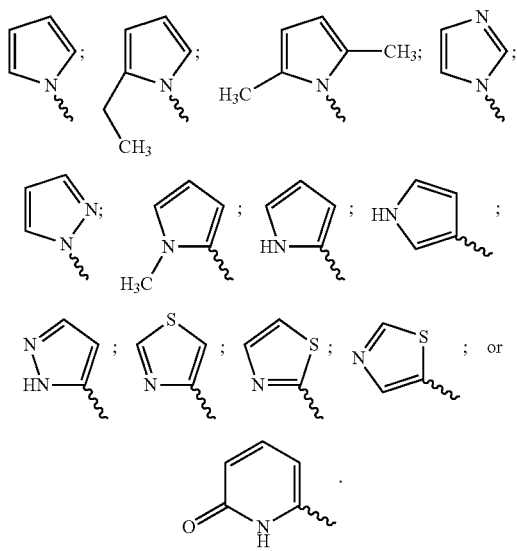
The invention further provides the following Pyrazolopyridazine compounds:
20
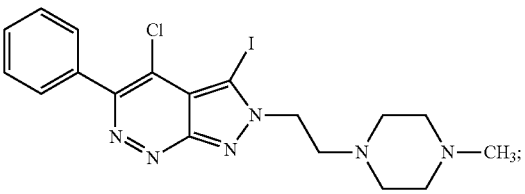
21
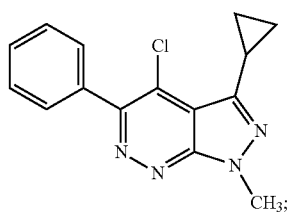
22
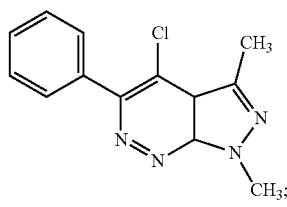
23
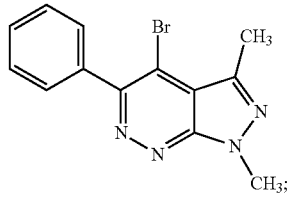

-continued

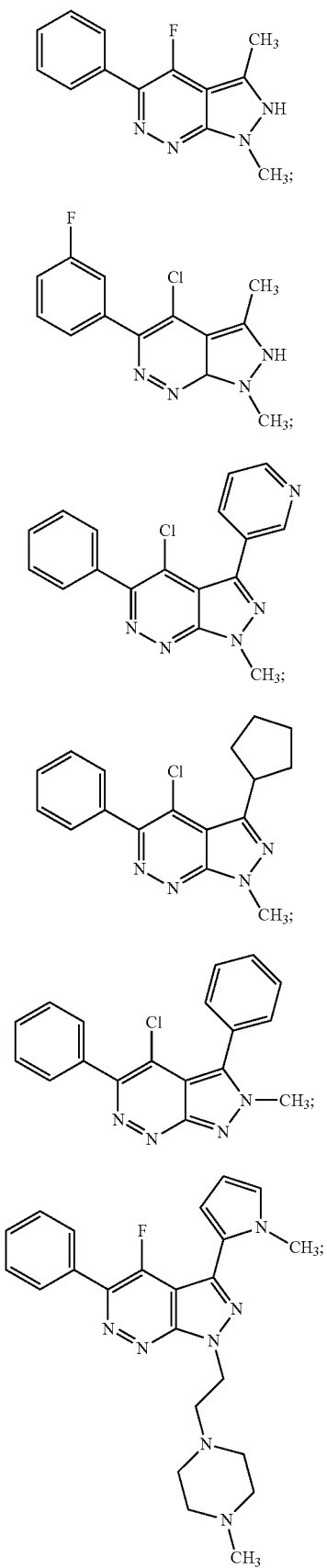

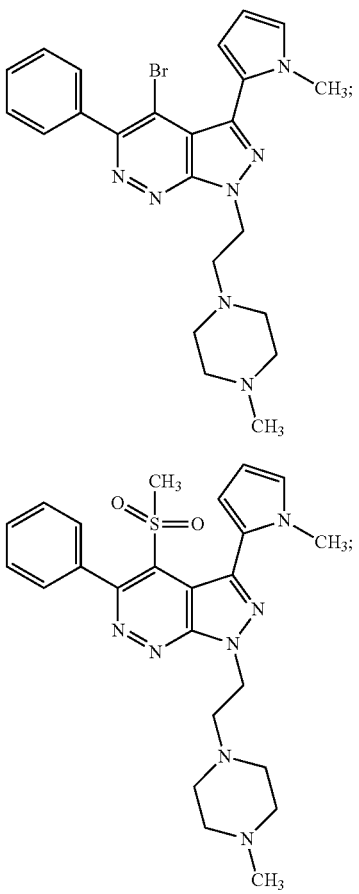

and pharmaceutically acceptable salts thereof.

A compound of Formula I, II, III, XIII, or XIV, Compound 20-30 or 31, or a pharmaceutically acceptable salt thereof, (a "Pyrazolopyridazine compound" or a "compound of the invention") is useful for treating a retinal degenerative disease or hearing loss associated with Usher Syndrome.

The invention further provides compositions comprising an effective amount of a Pyrazolopyridazine compound and a pharmaceutically acceptable carrier or vehicle. The compositions are useful for treating a retinal degenerative disease or hearing loss associated with Usher Syndrome.

The invention further provides methods for treating a retinal degenerative disease, comprising administering to a subject in need thereof an effective amount of a Pyrazolopyridazine compound.

The invention still further provides methods for treating hearing loss associated with Usher Syndrome, comprising administering to a subject in need thereof an effective amount of a Pyrazolopyridazine compound.

BRIEF DESCRIPTION OF THE FIGURE

FIG. 1 illustrates density of N48K Clarin-1 expression in cells.

DETAILED DESCRIPTION OF THE INVENTION

The invention provides compounds of the invention, compositions comprising a compound of the invention, and methods for treating a retinal degenerative disease or hearing loss associated with Usher Syndrome, comprising administering a Pyrazolopyridazine compound or a pharmaceutically acceptable salt thereof.

Compounds of the Invention

The word "about" when immediately preceding a numerical value means a range of plus or minus 10% of that value, e.g., "about 100 mg" means 90 mg to 110 mg, "about 300 mg" means 270 mg to 330 mg, etc.

ABBREVIATIONS

APCI Atmospheric Pressure Chemical Ionization
DAPI 4',6-diamidino-2-phenylindole
DIPEA diisopropylethylamine
DMEM Dulbecco's Modified Eagle Medium
DMF dimethylformamide
DMSO Dimethyl sulfoxide
EDAC 1-(3-dimethylaminopropyl)-3-ethylcarbodiimide hydrochloride
ESI Electrospray ionization
ESI-TOF Electrospray ionization-Time-of-flight
HATU 2-(7-Aza-1H-benzotriazole-1-yl)-1,1,3,3-tetramethyluronium hexafluorophosphate
HOPO 2-hydroxypyridine-N-oxide
HPLC High-performance liquid chromatography
LCMS Liquid chromatography-mass spectrometry
LDA lithium diisopropyl amide
m/z Mass-to-charge ratio
MALDI-TOF Matrix Assisted Laser Desorption Ionization-Time-of-flight
MS Mass spectrometry
PBS phosphate-buffered saline
Rt Retention time
SDS sodium dodecylsulfate
THF tetrahydrofuran Compounds of Formula I In one embodiment, the Pyrazolopyridazine compound is a compound of Formula I:

Formula I or a pharmaceutically acceptable salt thereof,
wherein $R_1$ is:

$R_2$ is:

and a is 0, 1, or 2.

In particular embodiments, $R_1$ is —I. In other embodiments, $R_1$ is —H. In yet other embodiments, $R_1$ is —$CH_3$. In certain embodiments, $R_1$ is —$CF_3$.

In yet other embodiments, $R_1$ is

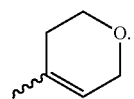

In certain embodiments, $R_1$ is

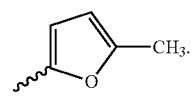

In still further embodiments, $R_1$ is

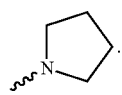

In particular embodiments, $R_1$ is

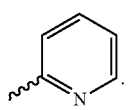

In other embodiments, $R_1$ is

In yet other embodiments, $R_1$ is

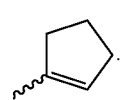

In certain embodiments, $R_1$ is

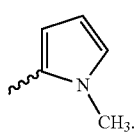

In particular embodiments, $R_1$ is

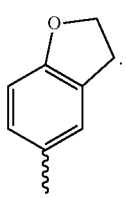

In certain embodiments, $R_1$ is

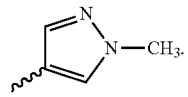

In still further embodiments, $R_1$ is

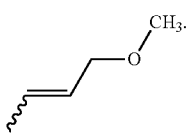

In other embodiments, $R_1$ is

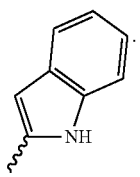

In yet other embodiments, $R_1$ is

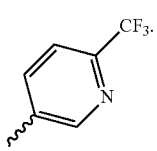

In certain embodiments, $R_1$ is

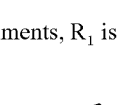

In still further embodiments, $R_1$ is

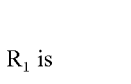

In other embodiments, $R_1$ is

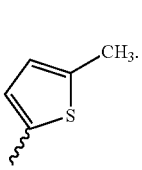

In particular embodiments, R₁ is

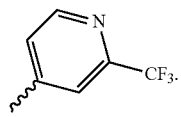

In further embodiments, R₁ is

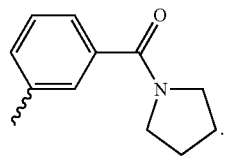

In still further embodiments, R₁ is

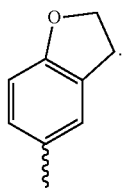

In certain embodiments, R₂ is —H. In yet other embodiments, R₂ is

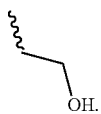

In particular embodiments, R₂ is

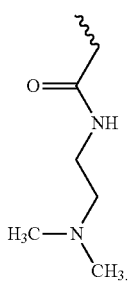

In yet other embodiments, R₂ is

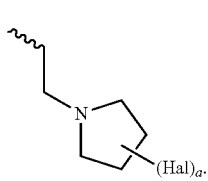

In further embodiments, R₂ is

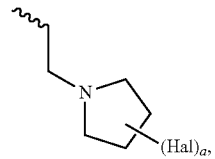

a=1, and Hal is —F.

In certain embodiments, R₂ is

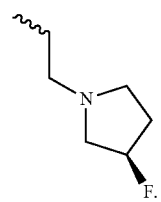

In still further embodiments, R₂ is

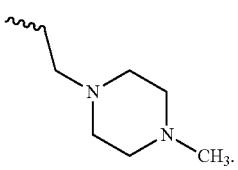

In particular embodiments, R₂ is

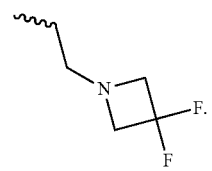

In other embodiments, R₂ is

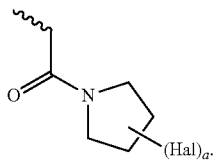

In yet other embodiments, R₂ is

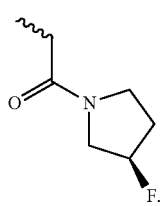

In certain embodiments, R₂ is
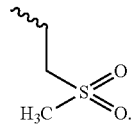
In further embodiments, when a is 2, each Hal is the same or different.
Illustrative compounds of Formula I are:
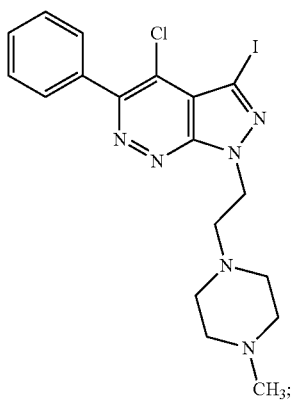
Ia
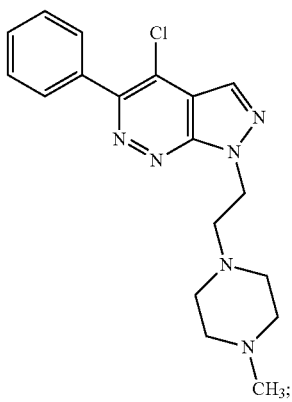
Ib
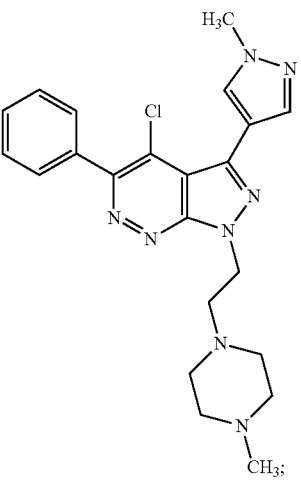
Ic
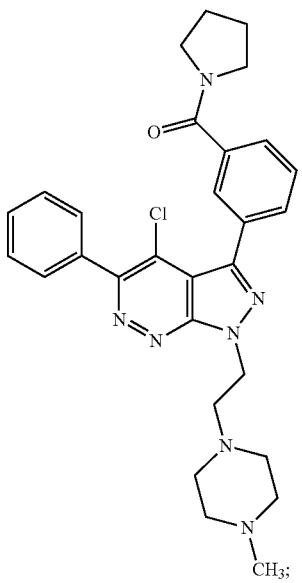
Id
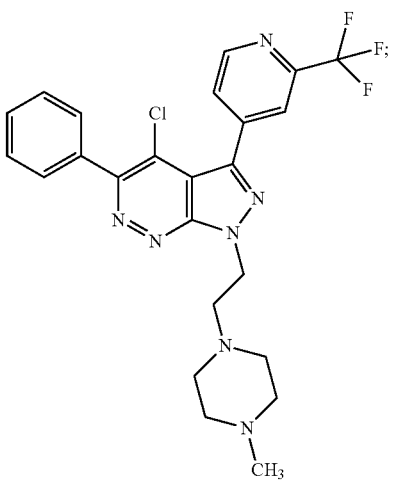
Ie
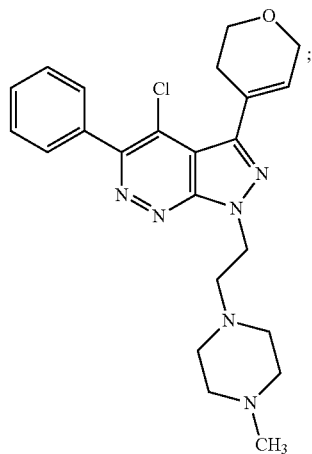
If

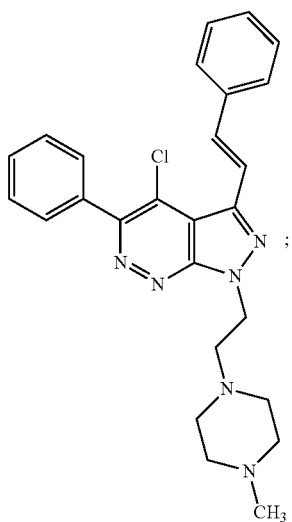
Ig
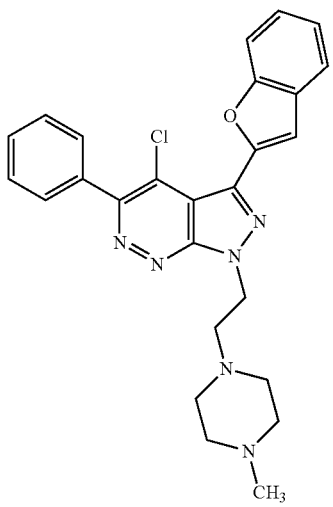
Ij
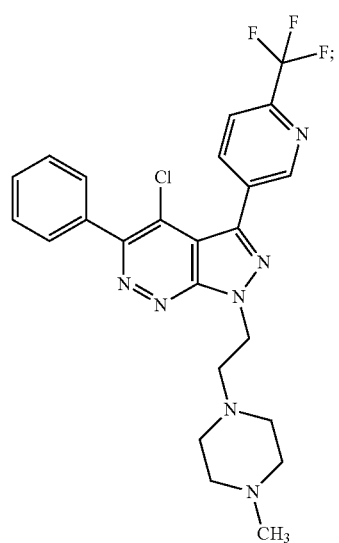
Ih
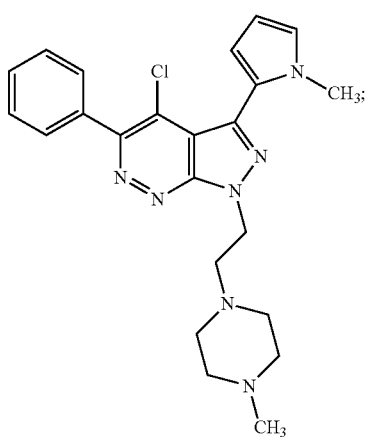
Ik
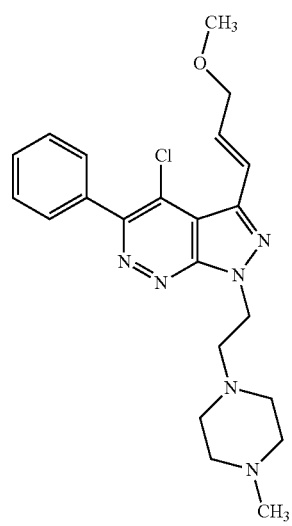
Ii
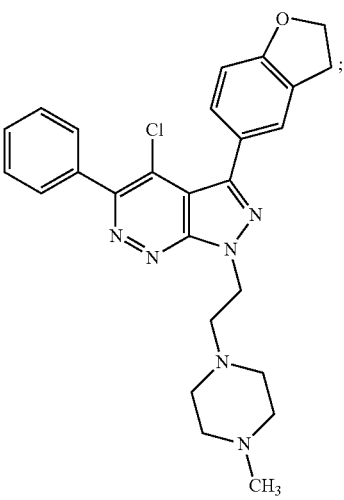
Il -continued
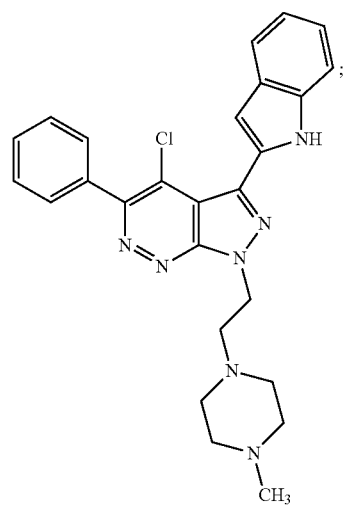
Im
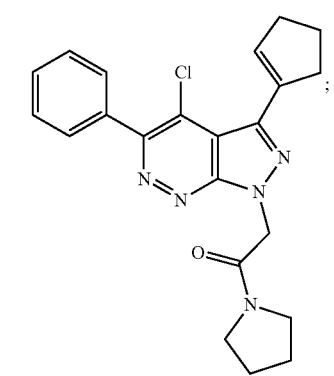
In
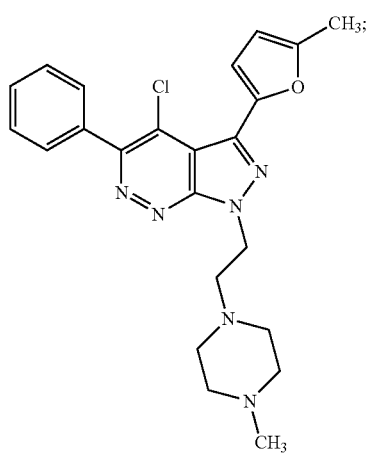
Io
-continued
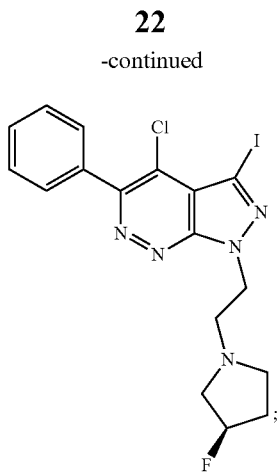
Ip
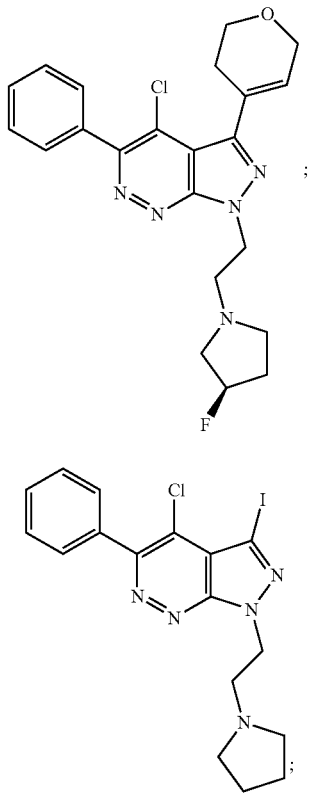
Iq
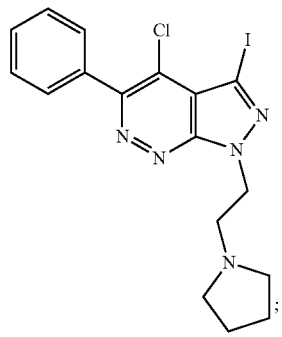
Ir
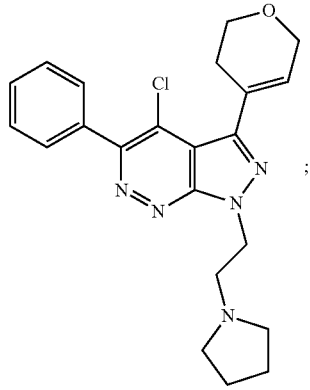
Is -continued
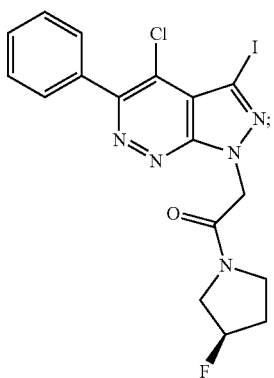
It
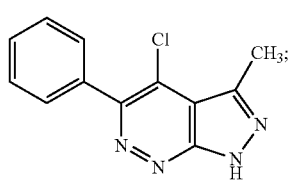
Iu
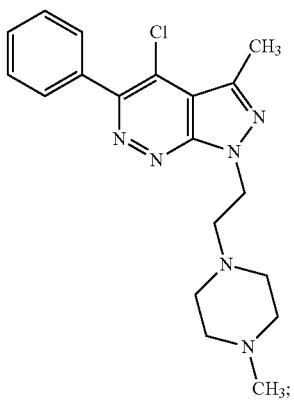
Iv
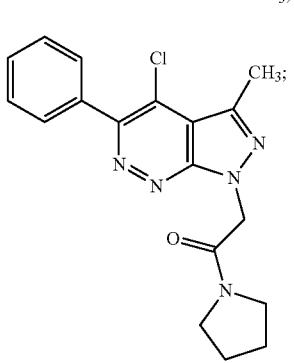
Iw
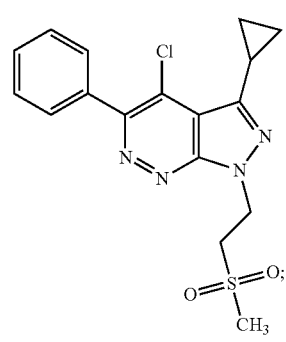
Ix
-continued
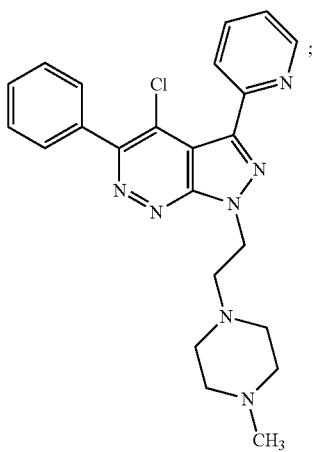
Iy
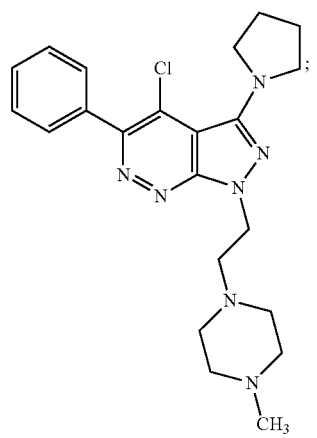
Iz
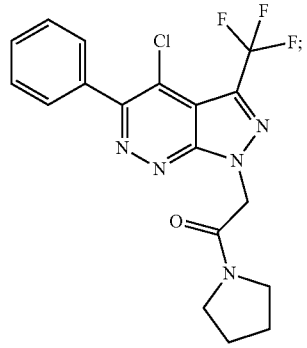
Iaa
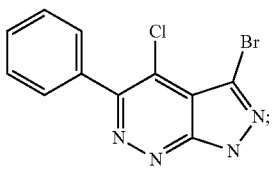
Ibb Icc
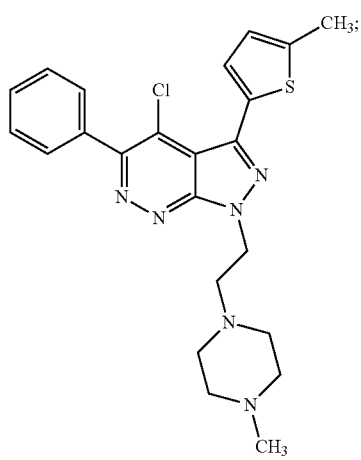
Idd
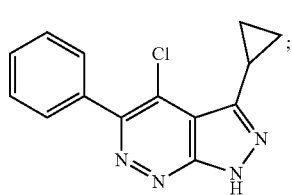
Iee
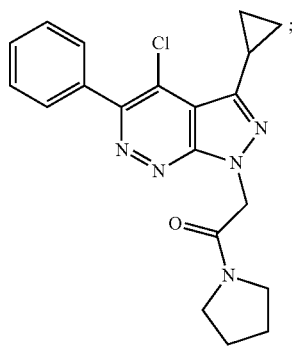
Iff
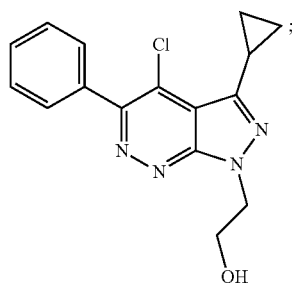
Igg
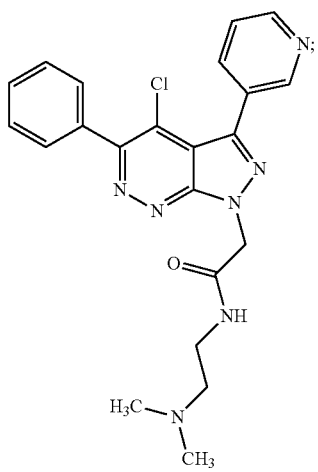
Ihh
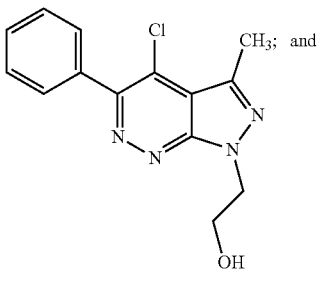
Iii
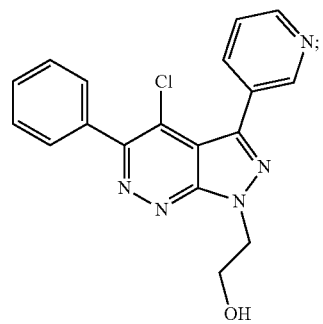
and pharmaceutically acceptable salts thereof.
Compounds of Formula II
The invention also provides compounds of Formula II:
Formula II
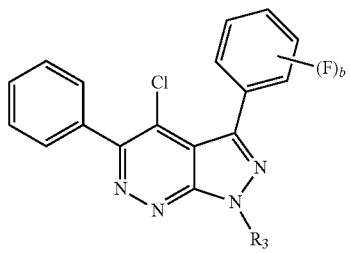
and pharmaceutically acceptable salts thereof, wherein R₃ is:

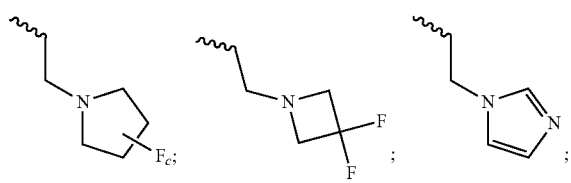

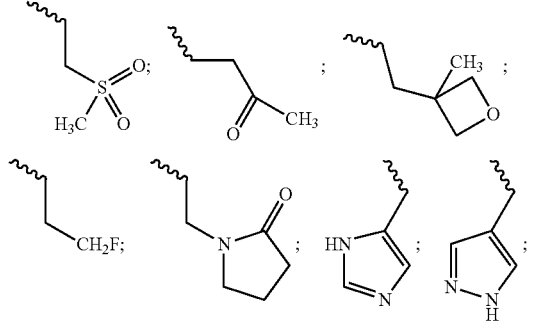

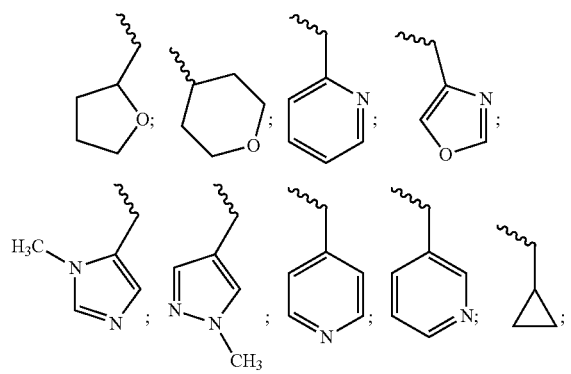

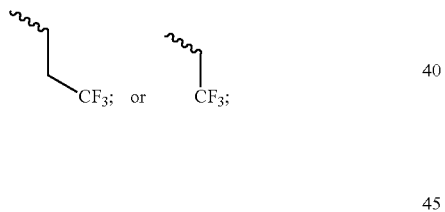

and
b is 0 or 1; and
c is 1 or 2.

In particular embodiments, b is 0. In other embodiments b is 1 and the —F is in the meta position relative to the pyrazolopyridazino ring system. In yet other embodiments b is 1 and the —F is in the para position relative to the pyrazolopyridazino ring system.

In particular embodiments R₃ is —CF₃. In certain embodiments R₃ is

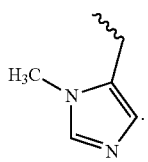

In other embodiments R₃ is

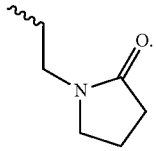

In yet other embodiments R₃ is

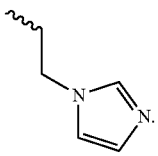

In further embodiments R₃ is

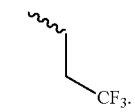

In still further embodiments R₃ is

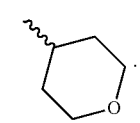

In particular embodiments R₃ is

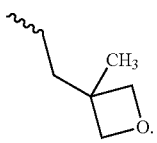

In other embodiments R₃ is

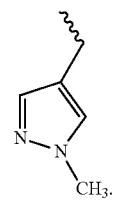

In yet other embodiments R₃ is

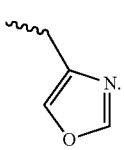

In certain embodiments R₃ is

In further embodiments R₃ is

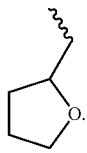

In further embodiments R₃ is

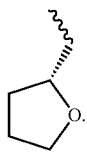

In certain embodiments R₃ is

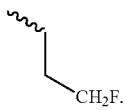

In other embodiments R₃ is

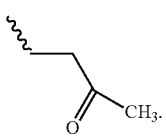

In yet other embodiments R₃ is

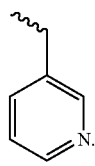

In further embodiments R₃ is

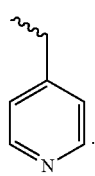

In still further embodiments R₃ is

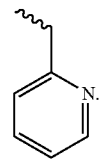

In particular embodiments R₃ is

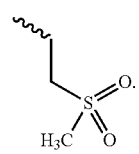

In certain embodiments R₃ is

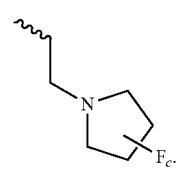

In further embodiments R₃ is c

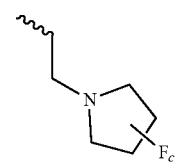

and c=1. In still further embodiments R₃ is

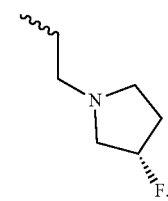

In particular embodiments R₃ is

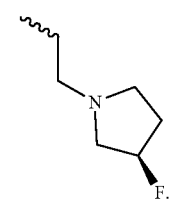

In other embodiments $R_3$ is
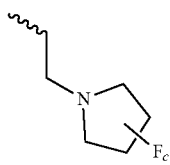
and c=2. In yet other embodiments $R_3$ is
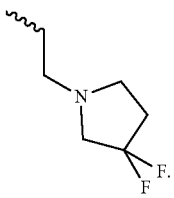
In certain embodiments $R_3$ is
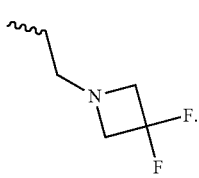
In other embodiments $R_3$ is
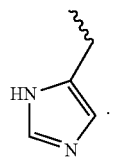
In yet other embodiments $R_3$ is
Illustrative compounds of Formula II are:
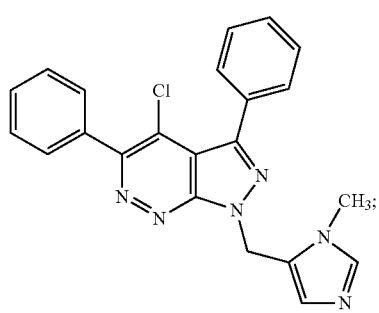
IIa
-continued
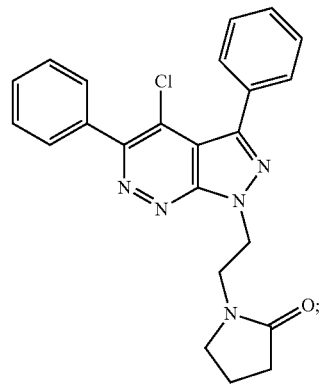
IIb
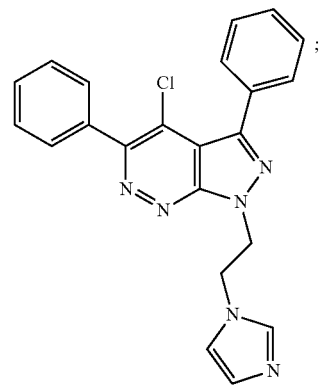
IIc
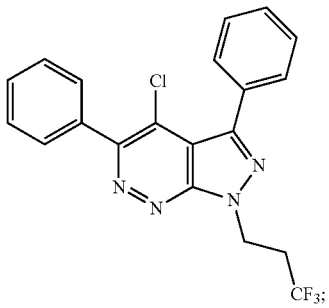
IId
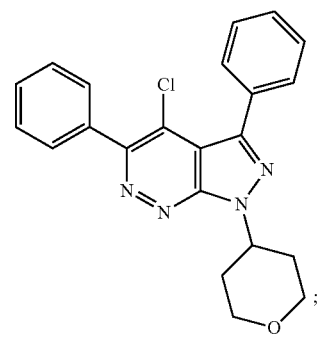
IIe -continued
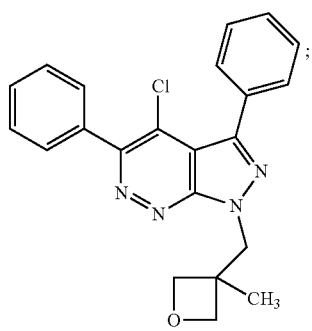
IIf
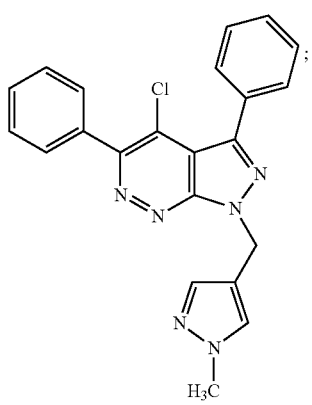
IIg
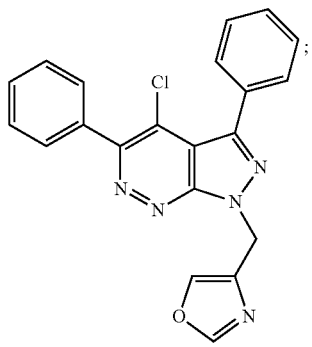
IIh
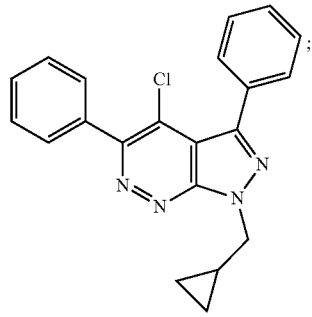
IIi
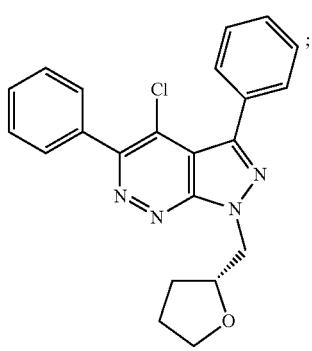
IIj
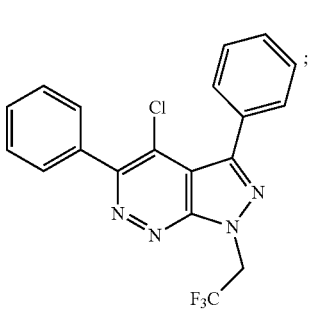
IIk
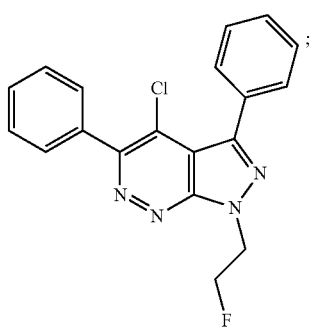
IIl
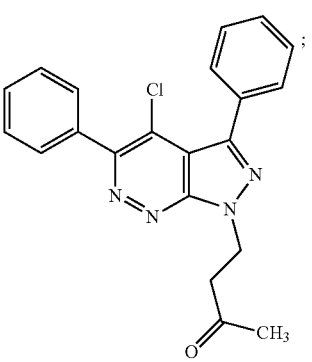
IIm IIn
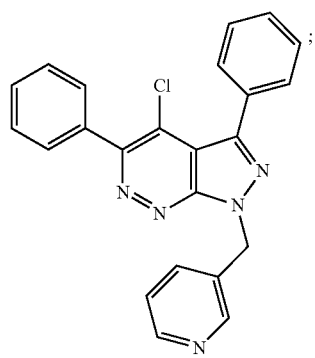
IIo
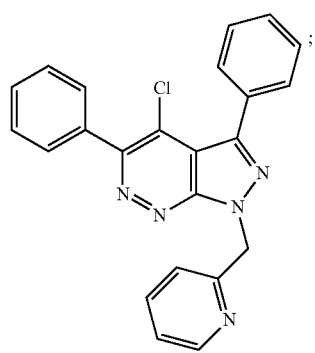
IIp
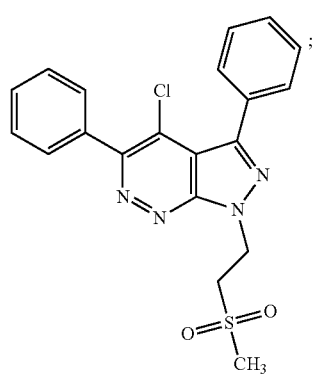
IIq
IIr
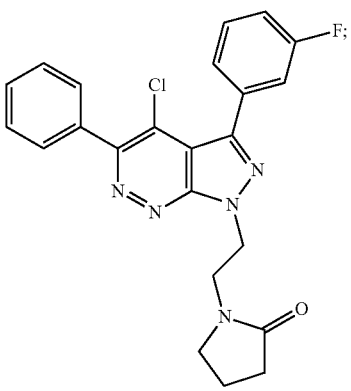
IIs
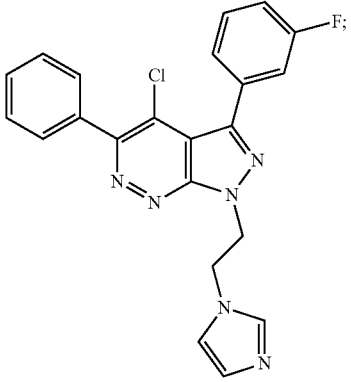
IIt
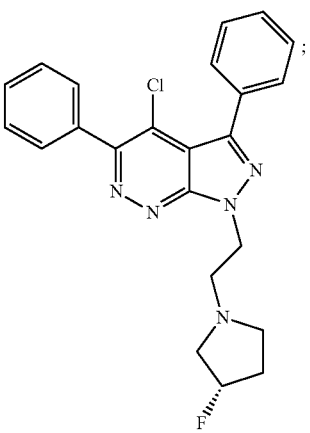
IIu
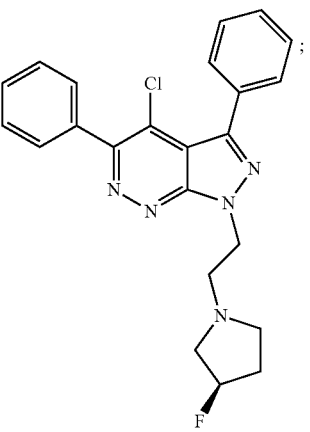

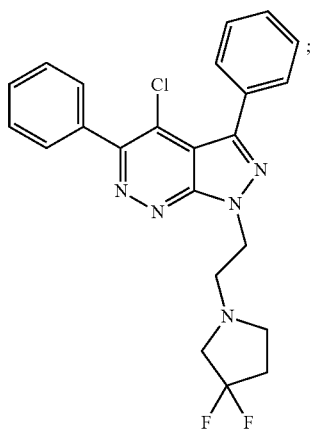
IIv
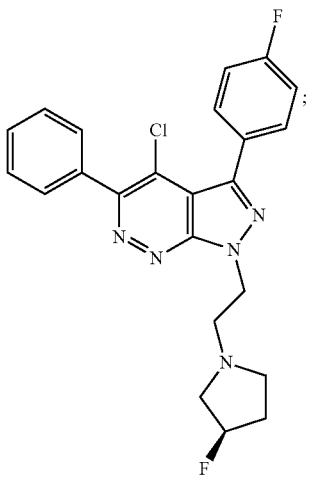
IIy
and pharmaceutically acceptable salts thereof.
Compounds of Formula III
The invention additionally provides compounds of Formula III:
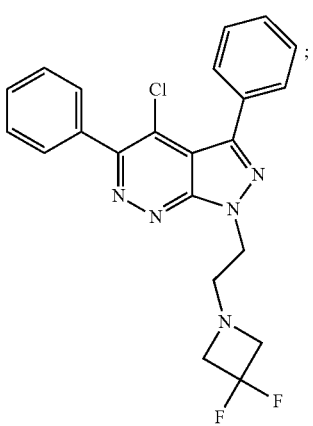
IIw
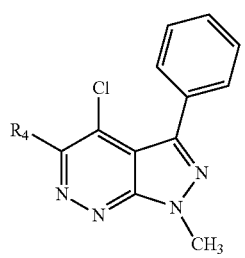
Formula III
and pharmaceutically acceptable salts thereof,
wherin R₄ is
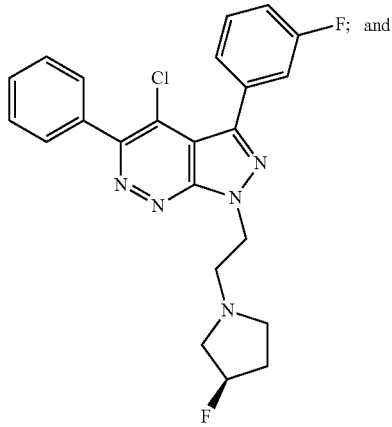
IIx
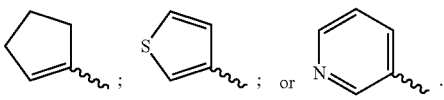
In certain embodiments R₄ is
In particular embodiments R₄ is

In other embodiments $R_4$ is
In yet other embodiments $R_4$ is
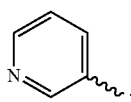
Illustrative compounds of Formula III are:
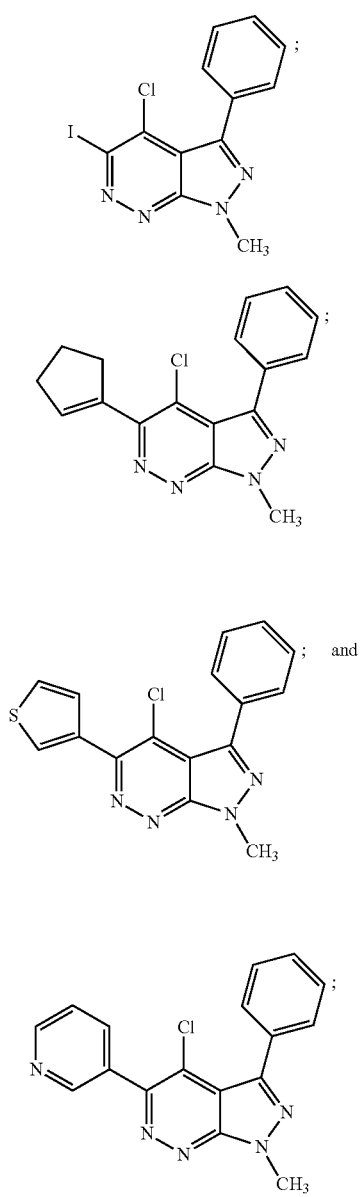
IIIa
IIIb
IIIc
IIId
and pharmaceutically acceptable salts thereof.
Compounds of Formula XIII
The invention provides compounds of Formula XIII:
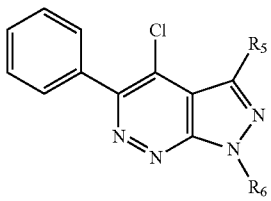
Formula XIII
and pharmaceutically acceptable salts thereof,
wherein $R_5$ is:
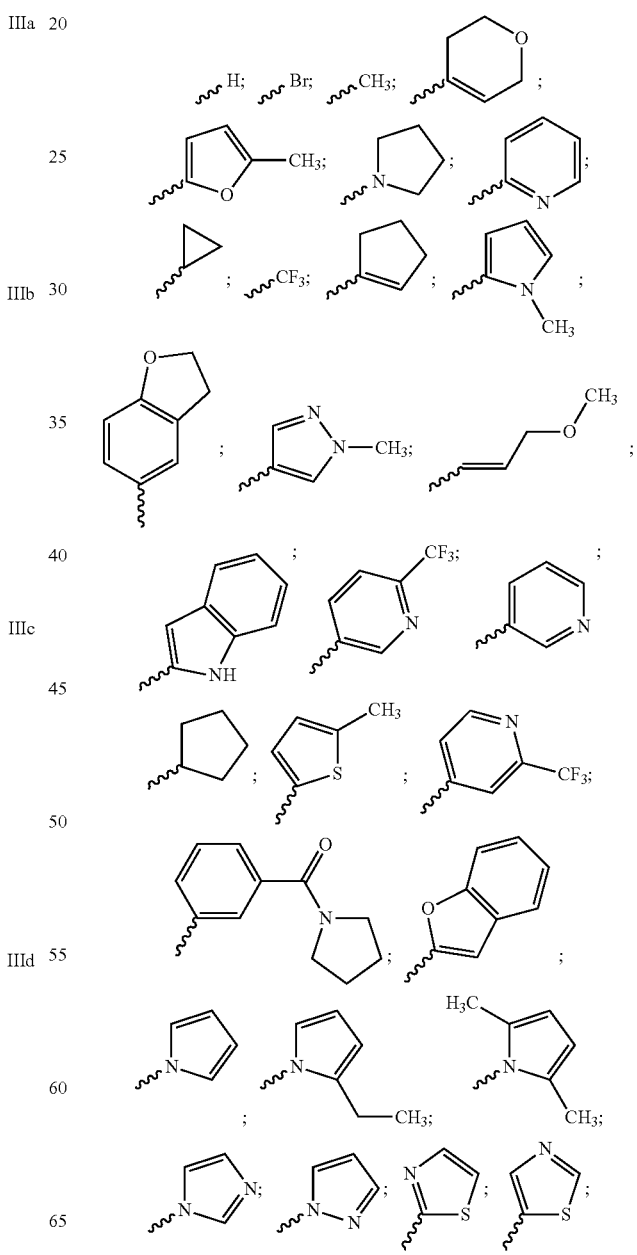

-continued
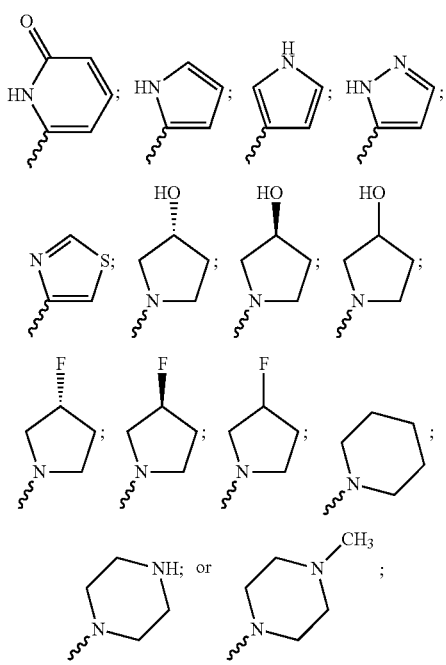
$R_6$ is:
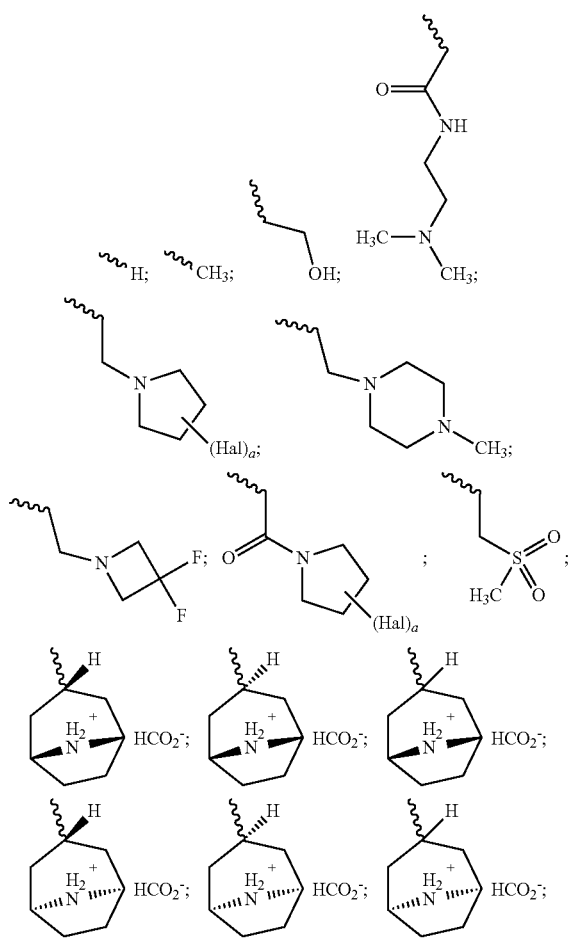
-continued
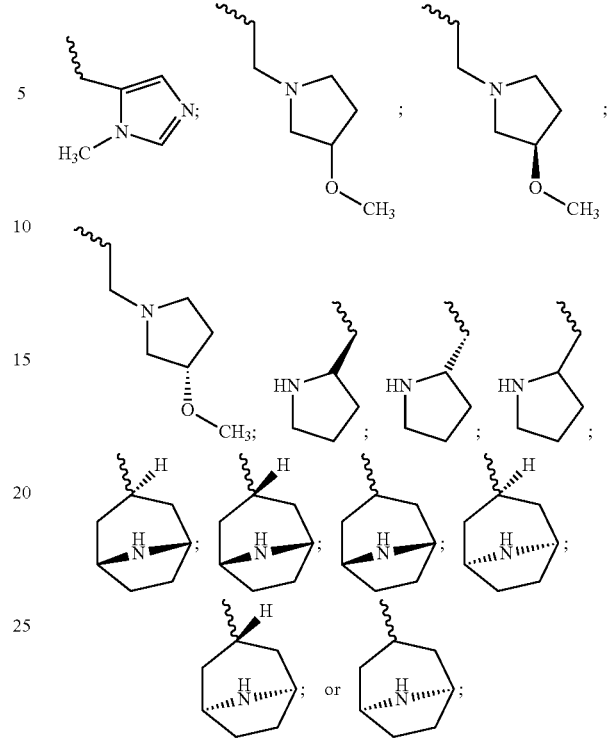
and
a is 0, 1, or 2.
In particular embodiments, $R_5$ is —I. In other embodiments, $R_5$ is —H. In yet other embodiments, $R_5$ is —$CH_3$. In certain embodiments, $R_5$ is —$CF_3$.
In yet other embodiments, $R_5$ is
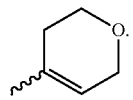
In certain embodiments, $R_5$ is
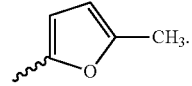
In still further embodiments, $R_5$ is N
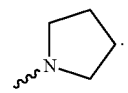
In particular embodiments, $R_5$ is N
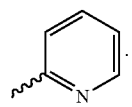

In other embodiments, $R_5$ is

In yet other embodiments, $R_5$ is

In certain embodiments, $R_5$ is

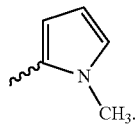

In particular embodiments, $R_5$ is

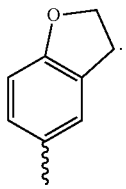

In certain embodiments, $R_5$ is

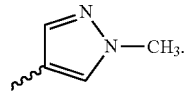

In still further embodiments, $R_5$ is

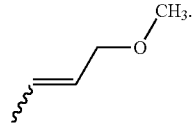

In other embodiments, $R_5$ is

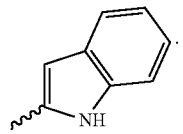

In yet other embodiments, $R_5$ is

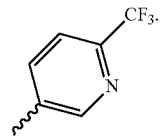

In certain embodiments, $R_5$ is

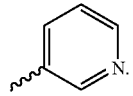

In still further embodiments, $R_5$ is

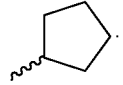

In other embodiments, $R_5$ is

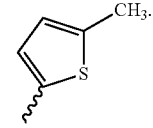

In particular embodiments, $R_5$ is

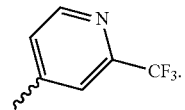

In further embodiments, $R_5$ is

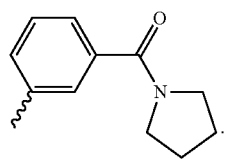

In still further embodiments, $R_5$ is

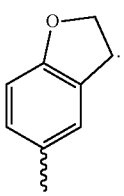

In certain embodiments, $R_5$ is

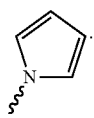

In further embodiments, $R_5$ is

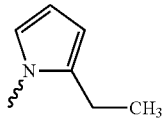

In further embodiments, $R_5$ is

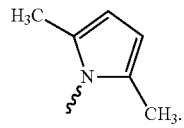

In other embodiments, $R_5$ is

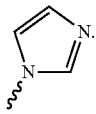

In yet other embodiments, $R_5$ is

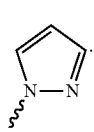

In particular embodiments, $R_5$ is

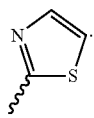

In further embodiments, $R_5$ is

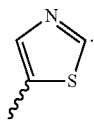

In still further embodiments, $R_5$ is

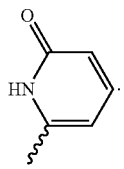

In certain embodiments, $R_5$ is

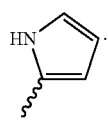

other embodiments, $R_5$

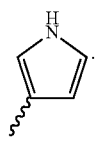

In yet other embodiments, $R_5$ is

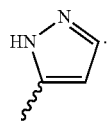

In particular embodiments, $R_5$ is

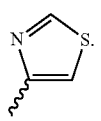

In further embodiments, $R_5$ is

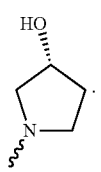

In still further embodiments, $R_5$ is

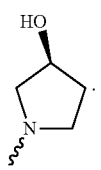

In certain embodiments, $R_5$ is

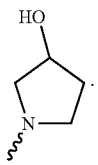

In other embodiments, $R_5$ is

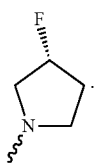

In yet other embodiments, $R_5$ is

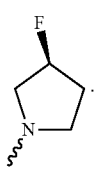

In particular embodiments, $R_5$ is

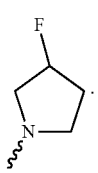

In further embodiments, $R_5$ is

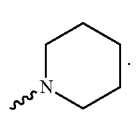

In still further embodiments, $R_5$ is

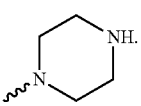

In certain embodiments, $R_5$ is

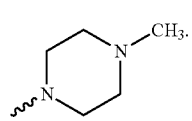

In certain embodiments, $R_6$ is

In further embodiments, $R_6$ is

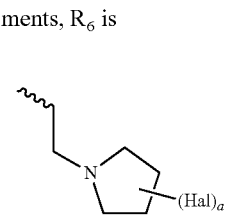

and a=0. In other embodiments, $R_6$ is

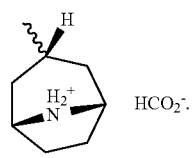

In yet other embodiments, $R_6$ is

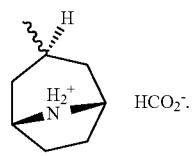

In particular embodiments, $R_6$ is

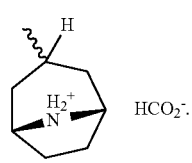

In certain embodiments, $R_6$ is

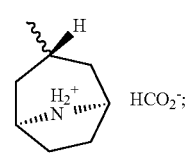

In further embodiments, $R_6$ is

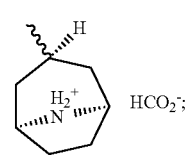

In further embodiments, R$_6$ is

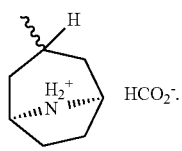

In certain embodiments, R$_6$ is

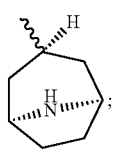

In further embodiments, R$_6$ is

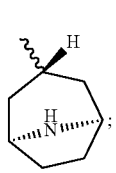

In particular embodiments, R$_6$ is

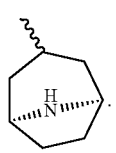

In further embodiments, R$_6$ is

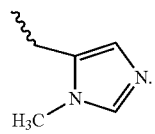

In still further embodiments, R$_6$ is

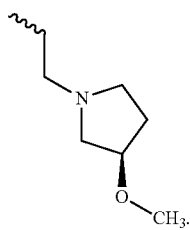

In other embodiments, R$_6$ is

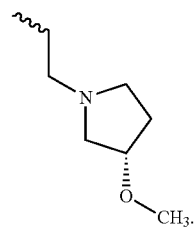

In certain embodiments, R$_6$ is

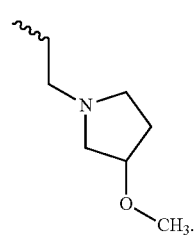

In yet other embodiments, R$_6$ is

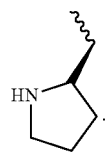

In particular embodiments, R$_6$ is

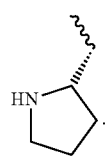

In further embodiments, R$_6$ is

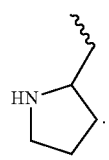

In still further embodiments, R$_6$ is

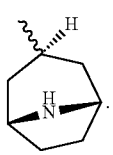

In certain embodiments, $R_6$ is
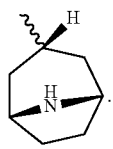
In other embodiments, $R_6$ is
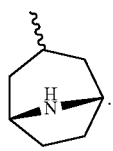
In further embodiments, when a is 2, each Hal is the same or different.
Illustrative compounds of Formula XIII are:
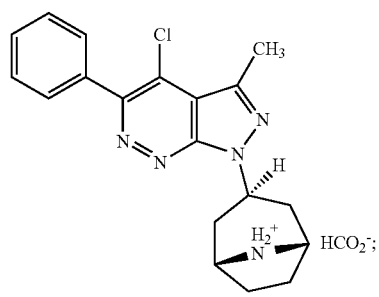
XIIIa
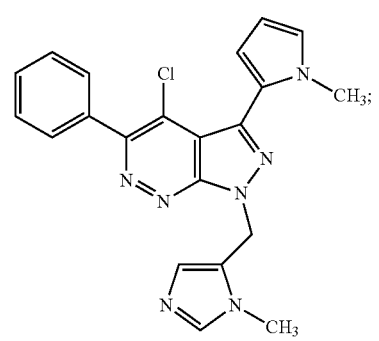
XIIIb
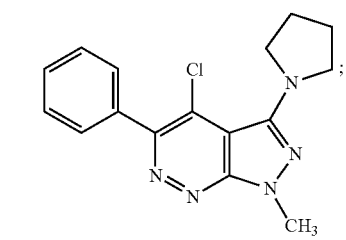
XIIIc
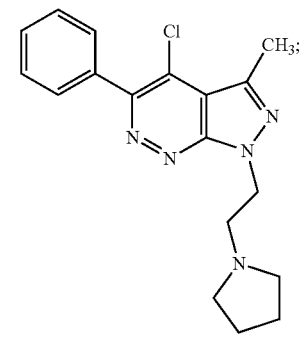
XIIId
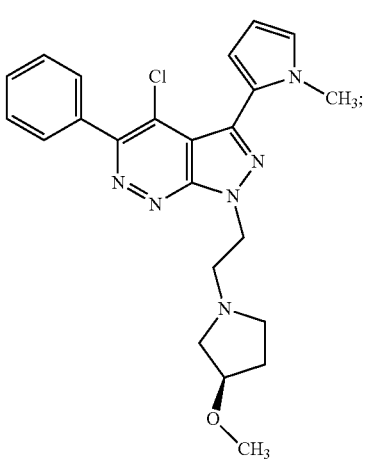
XIIIe
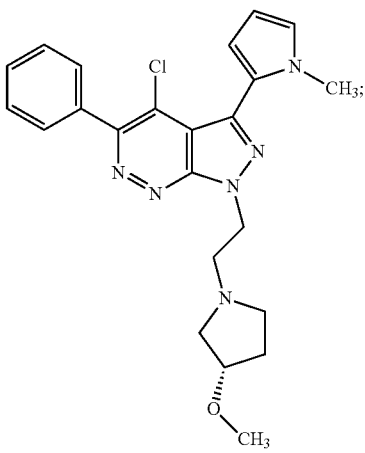
XIIIf
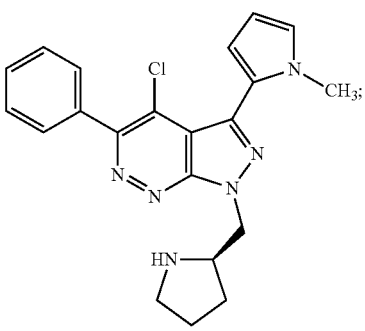
XIIIg

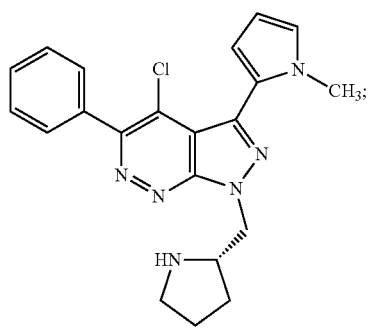
XIIIh
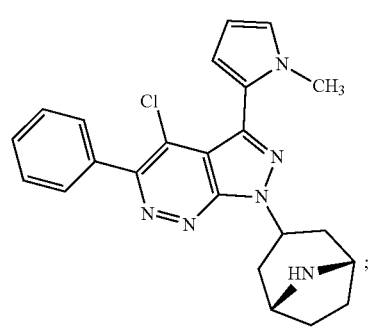
XIIIi
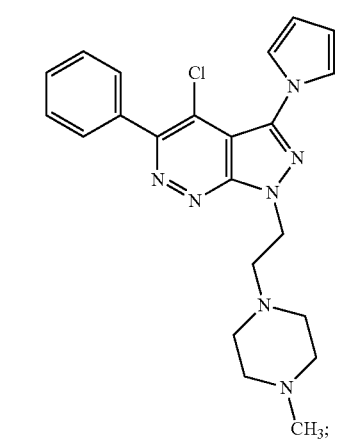
XIIIj
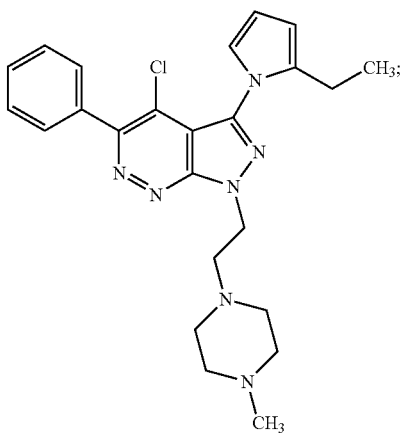
XIIIk
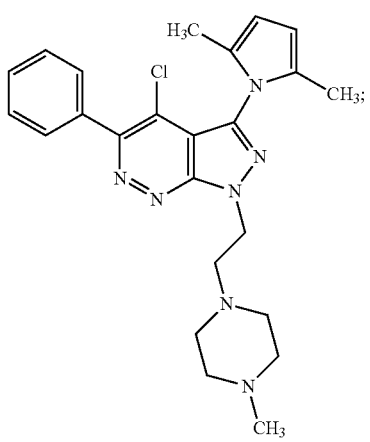
XIIIl
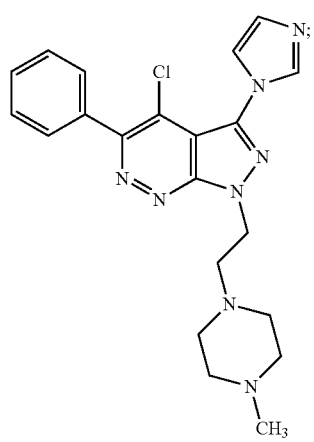
XIIIm
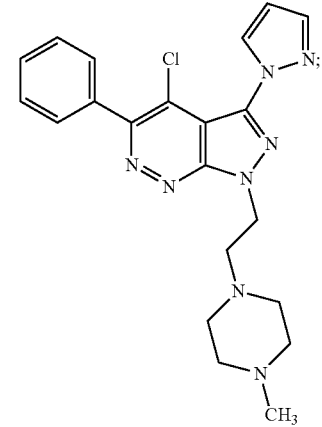
IIIn

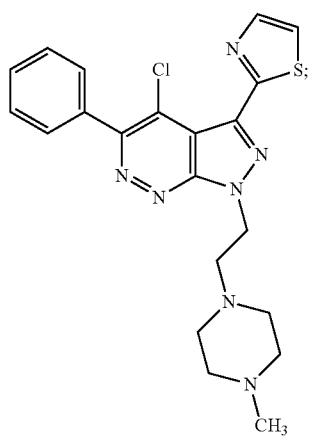
XIIIo
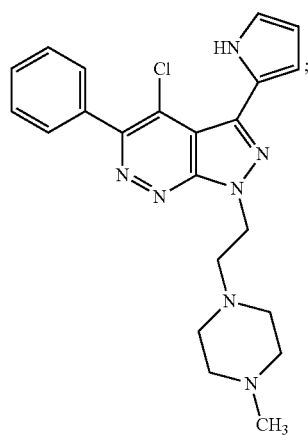
XIIIr
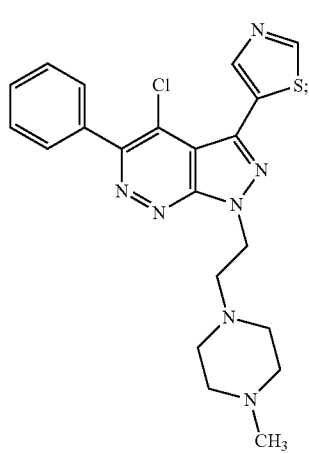
XIIIp
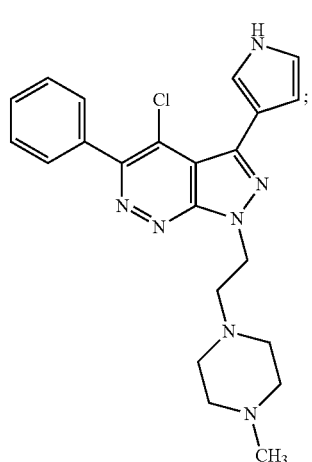
XIIIs
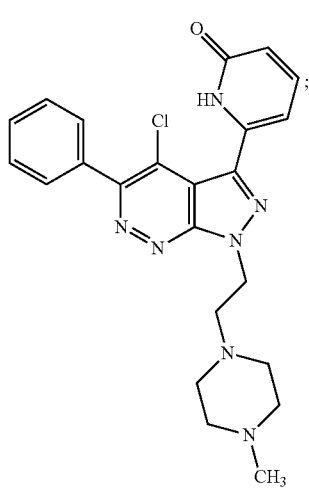
XIIIq
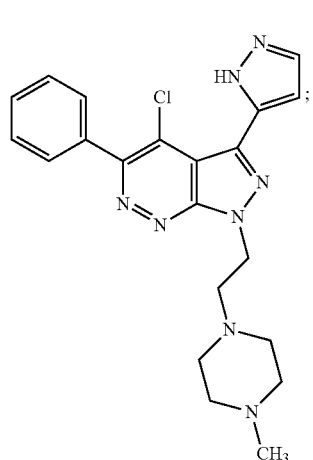
XIIIt

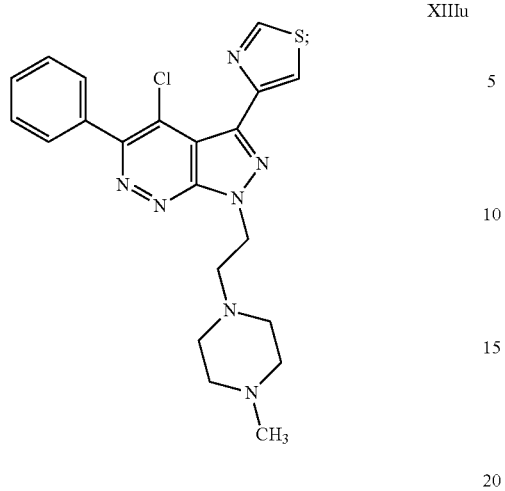
XIIIu
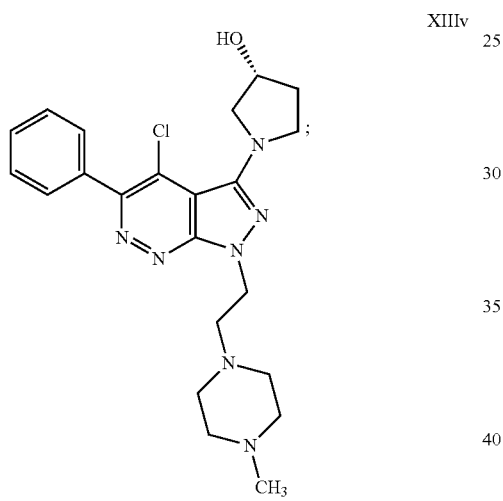
XIIIv
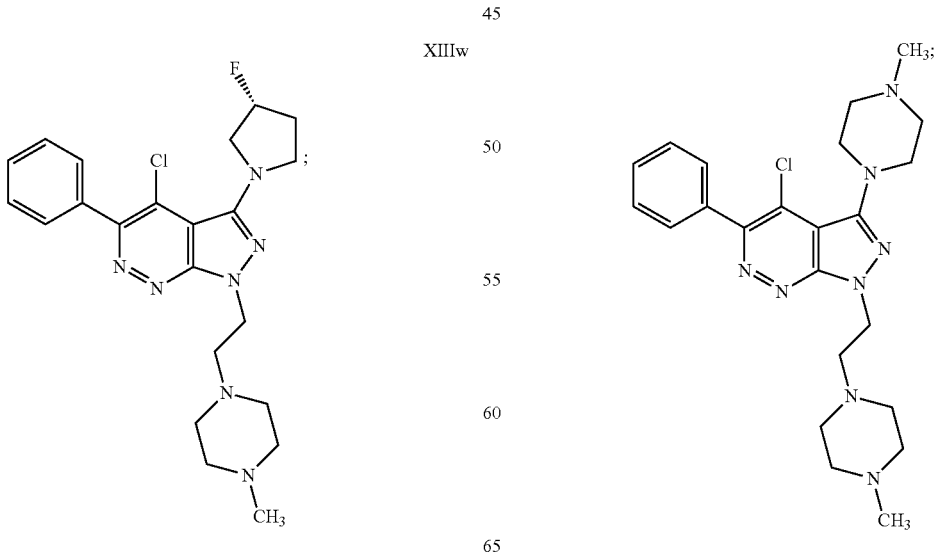
XIIIw
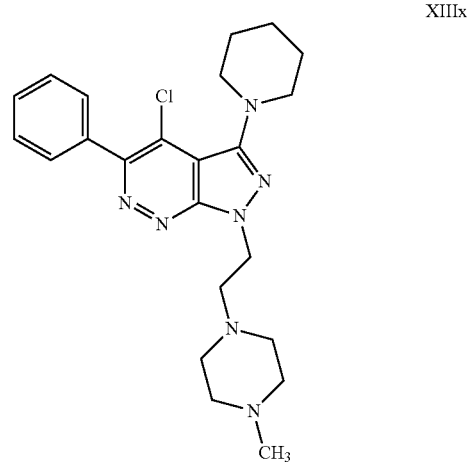
XIIIx
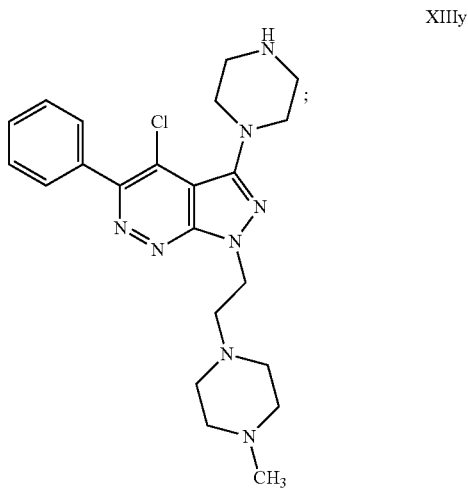
XIIIy
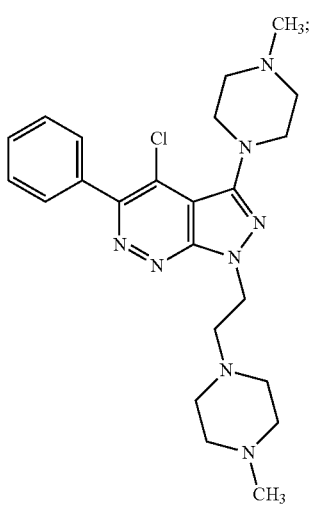
XIIIz
and pharmaceutically acceptable salts thereof.

Compounds of Formula XIV

The invention also provides compounds of Formula XIV:

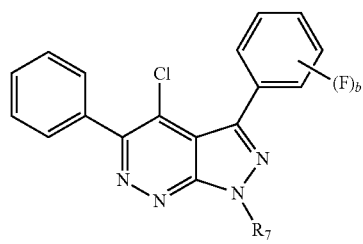

Formula XIV and pharmaceutically acceptable salts thereof,
wherein $R_7$ is:

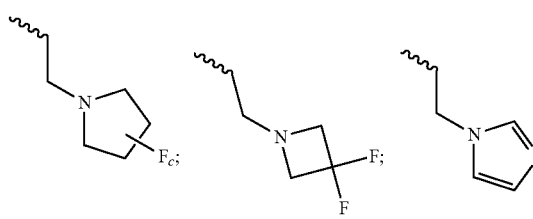

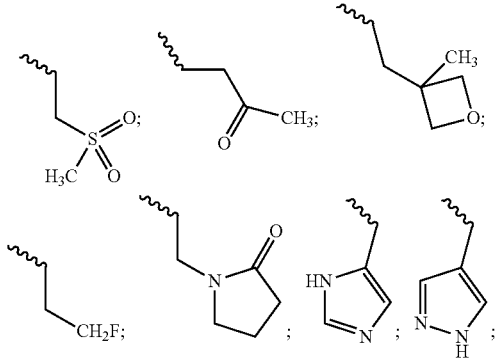

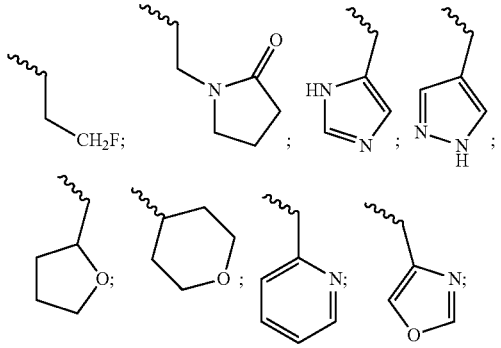

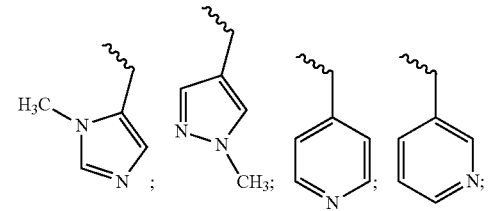

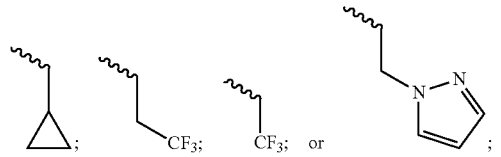

b is 0 or 1; and
c is 1 or 2.

In particular embodiments, b is 0. In other embodiments b is 1 and the —F is in the meta position relative to the pyrazolopyridazino ring system. In yet other embodiments b is 1 and the —F is in the para position relative to the pyrazolopyridazino ring system.

In particular embodiments $R_3$ is —$CF_3$. In certain embodiments $R_3$ is

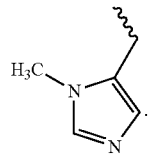

In other embodiments $R_3$ is

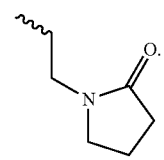

In yet other embodiments $R_3$ is

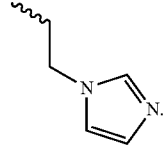

In further embodiments $R_3$ is

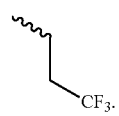

In still further embodiments $R_3$ is

In particular embodiments $R_3$ is

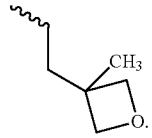

In other embodiments R₃ is

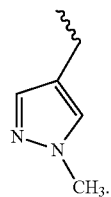

In yet other embodiments R₃ is

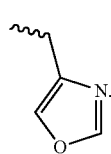

In certain embodiments R₃ is

In further embodiments R₃ is

In further embodiments R₃ is

In certain embodiments R₃ is

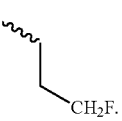

In other embodiments R₃ is

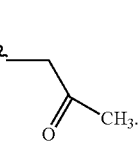

In yet other embodiments R₃ is

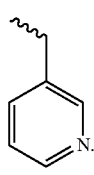

In further embodiments R₃ is N

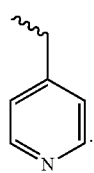

In still further embodiments R₃ is

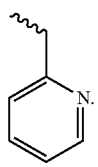

In particular embodiments R₃ is

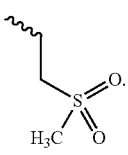

In certain embodiments R₃ is

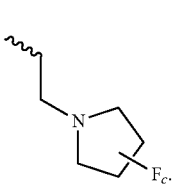

In further embodiments R₃ is

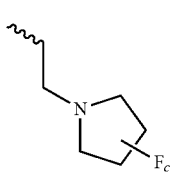

and c=1. In still further embodiments $R_3$ is

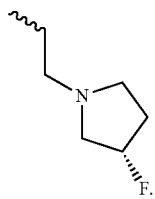

In particular embodiments $R_3$ is

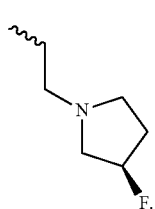

In other embodiments $R_3$ is

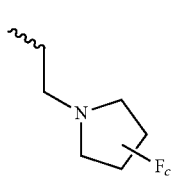

and c=2. In yet other embodiments $R_3$ is

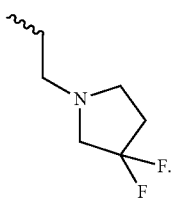

In certain embodiments $R_3$ is

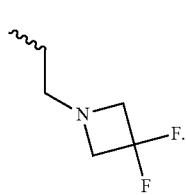

In other embodiments $R_3$ is

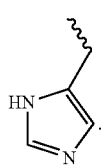

In yet other embodiments $R_3$ is

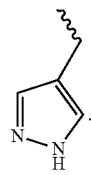

In yet other embodiments $R_3$ is

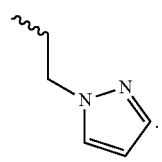

An illustrative compound of Formula XIV is:
XIVa:

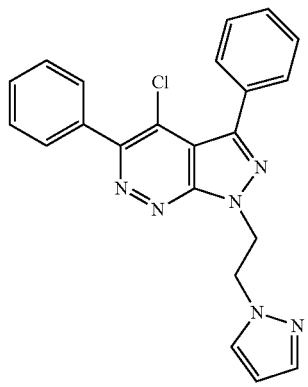 [SMILES: Clc1c(-c2ccccc2)nnc2c1c(-c1ccccc1)nn2CCn1cccn1]

and pharmaceutically acceptable salts thereof.

Compounds of Formula XV

The invention also provides compounds of Formula XV:

Formula XV

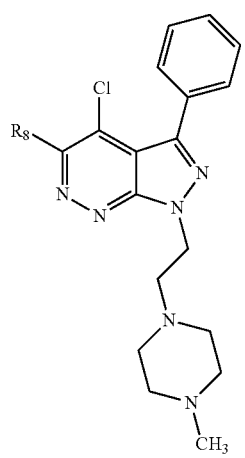

and pharmaceutically acceptable salts thereof, wherein R₈ is:

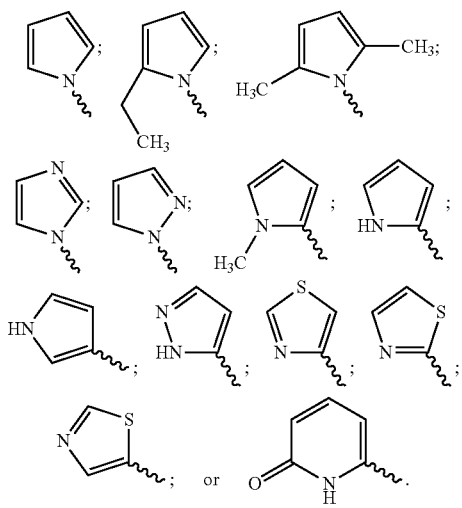

In particular embodiments R₈ is N

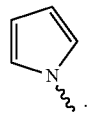

In certain embodiments R₈ is

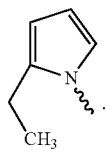

In other embodiments R₈ is

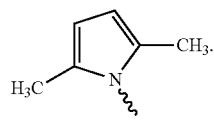

In yet other embodiments R₈ is

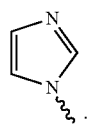

In further embodiments R₈ is

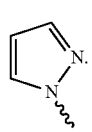

In still further embodiments R₈ is

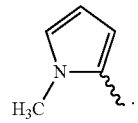

In particular embodiments R₈ is

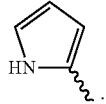

In particular embodiments R₈ is

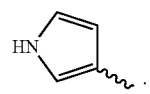

In certain embodiments R₈ is

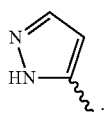

In other embodiments R₈ is

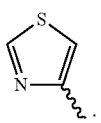

In yet other embodiments R₈ is

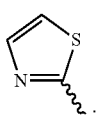

In further embodiments R₈ is

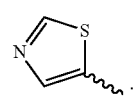

In still further embodiments R₈ is

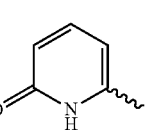

Illustrative compounds of Formula XV are:
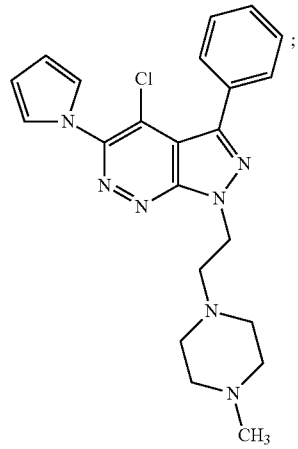
XVa
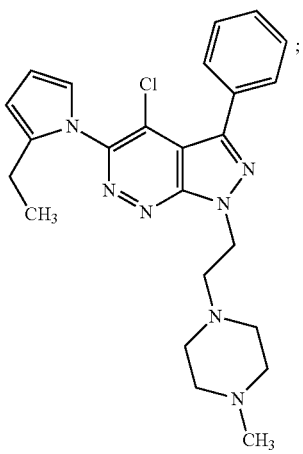
XVb
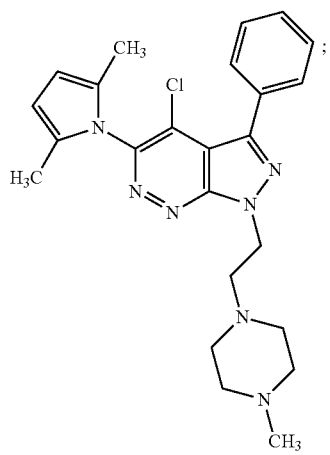
XVc
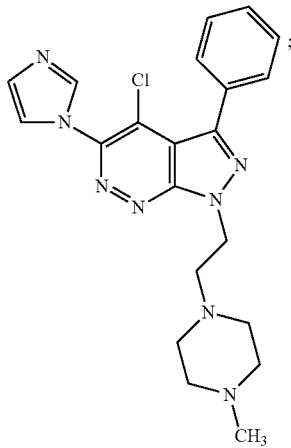
XVd
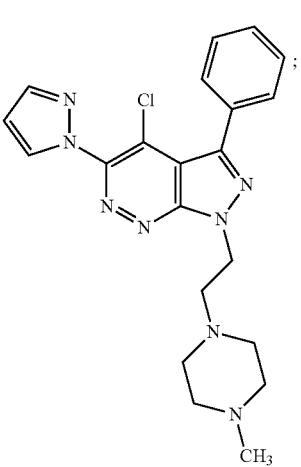
XVe
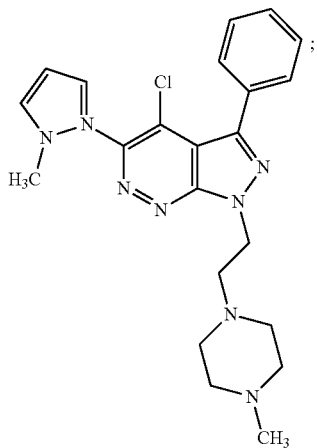
XVf -continued
XVg
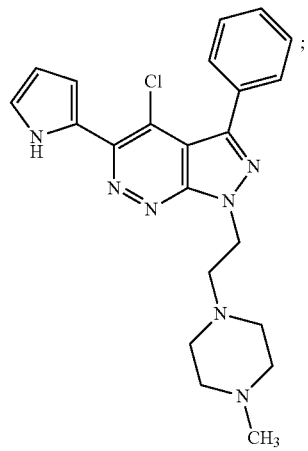
XVh
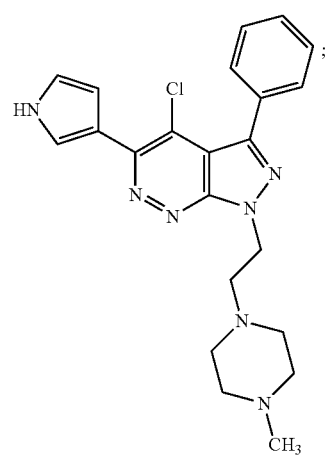
XVi
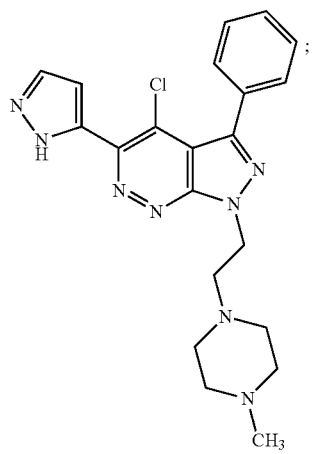
-continued
XVj
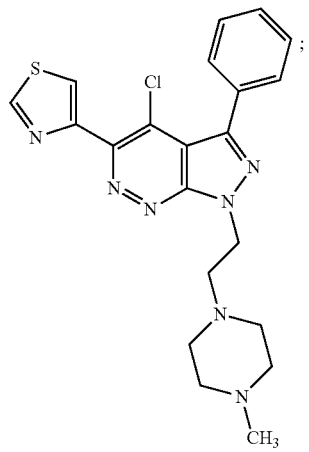
XVk
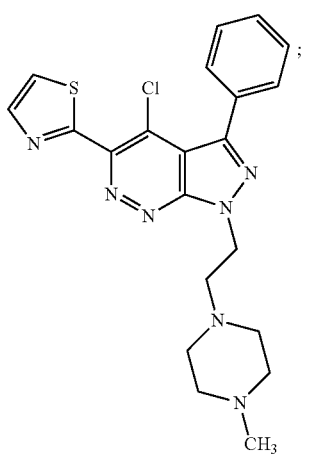
XVl
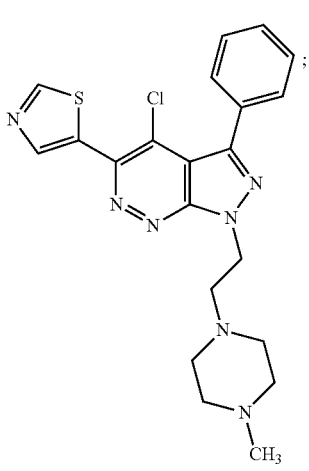

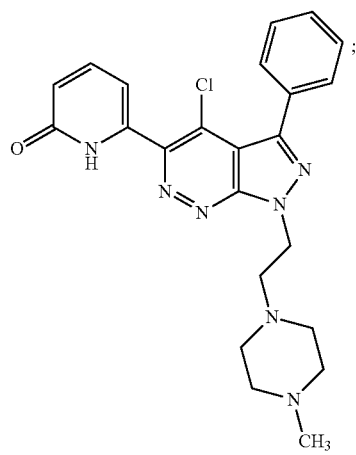
XVm
and pharmaceutically acceptable salts thereof.
Additional Pyrazolopyridazine Compounds
The invention further provides the following Pyrazolopyridazine compounds:
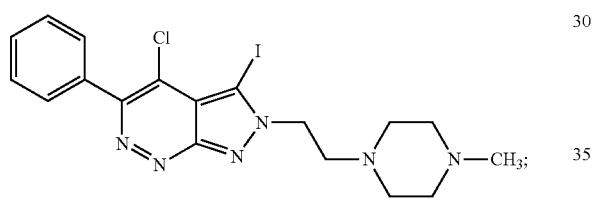
20
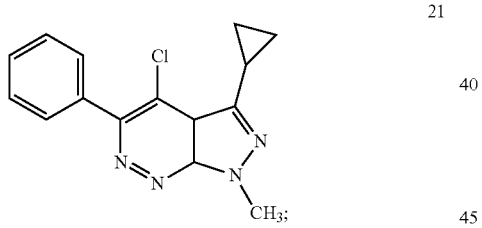
21
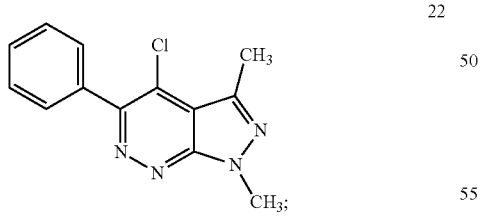
22
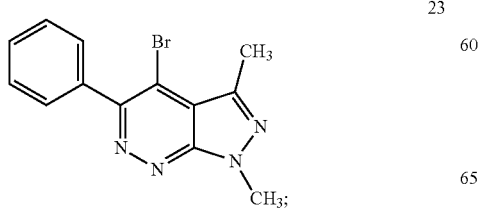
23
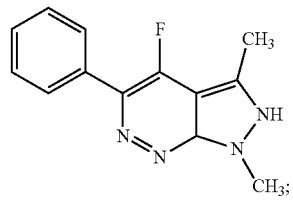
24
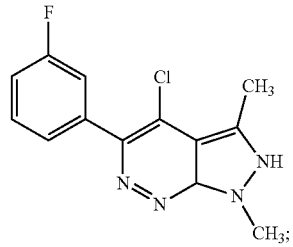
25
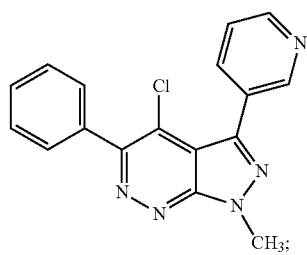
26
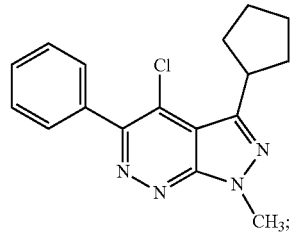
27
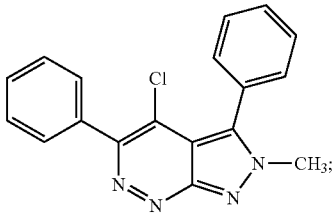
28
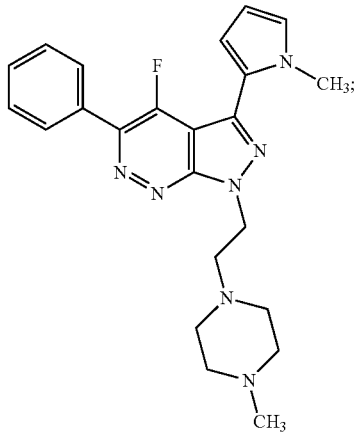
29

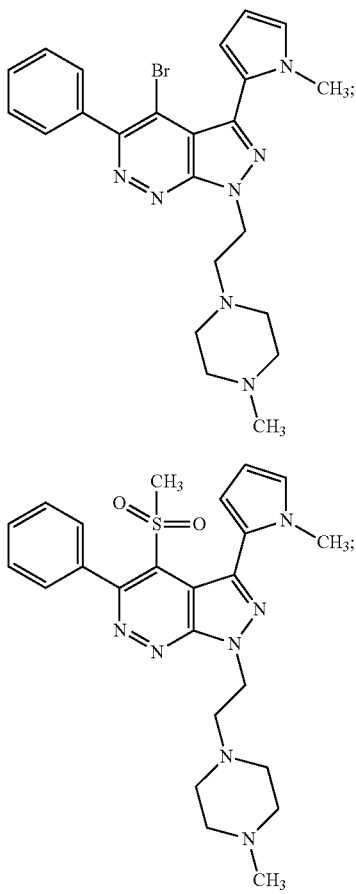

and pharmaceutically acceptable salts thereof.

Some of the compounds disclosed herein, for example, Compounds Ip, Iq, It, IIj, IIt, IIu, IIx, IIy, XIIIe, XIIIf, XIIIg, XIIIh. XIIIi; XIIIv, and XIIIw; are depicted having a bold or hatched wedge, indicating absolute stereochemistry.

Without being bound by any particular mechanism, it is believed that the bisphenyl pyrazolopyridazine moiety of Pyrazolopyridazine compounds is involved in the restoration of the activity and trafficking of Clarin I, which is the protein encoded by the gene mutated in Usher III Syndrome (Adato et al., Eur J Hum Genet. 2002 June; 10(6):339-50)

The compounds of the invention can be in the form of a salt. In some embodiments, the salt is a pharmaceutically acceptable salt. Pharmaceutically acceptable salts include, for example, acid-addition salts and base-addition salts. The acid that forms an acid-addition salt can be an organic acid or an inorganic acid. A base that forms a base-addition salt can be an organic base or an inorganic base. In some embodiments, a pharmaceutically acceptable salt is a metal salt. In some embodiments, a pharmaceutically acceptable salt is an ammonium salt.

Acid-addition salts can arise from the addition of an acid to the free-base form of a compound of the invention. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid-addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound of the invention having a carboxyl group. The inorganic base consists of a metal cation paired with a basic couterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, a aluminum salt, a copper salt, a cadmium salt, and a zinc salt.

Ammonium salts can arise from the addition of ammonia or an organic amine to a compound of the invention having a carboxyl group. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethylammonium salt, a diisopropylammonium salt, an ethanolammonium salt, a diethanolammonium salt, a triethanolammonium salt, a morpholinium salt, an N-methylmorpholinium salt, a piperidinium salt, an N-methylpiperidinium salt, an N-ethylpiperidinium salt, a dibenzylammonium salt, a piperazinium salt, a pyridinium salt, a pyrrazolium salt, an imidazolium salt, a pyrazinium salt, an ethylenediammonium salt, an N,N'-dibenzylethylenediammonium salt, a procaine salt, a chloroprocaine salt, a choline salt, a dicyclohexylammonium salt, and a N-methylglucamine salt.

Therapeutic Uses

A compound of the invention can be administered to a subject in need thereof for the treatment of a retinal degenerative disease. Non-limiting examples of retinal degenerative diseases include: retinitis pigmentosa, Leber's congenital Amaurosis, Syndromic retinal degenerations, age-related macular degeneration including wet and dry age-related macular degeneration, and Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

In a further embodiment of the invention, a compound of the invention can be administered to a subject in need thereof for the treatment of hearing loss associated with Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

A "subject" is a mammal, e.g., a human, mouse, rat, guinea pig, dog, cat, horse, cow, pig, or non-human primate, such as a monkey, chimpanzee, baboon or rhesus. In one embodiment, the subject is a human.

The compounds of the invention can be administered to a subject as a component of a composition that comprises a pharmaceutically acceptable carrier or vehicle. Non-limiting examples of suitable pharmaceutical carriers or vehicles include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, and phosphate buffered saline. These compositions can be administered as, for example, drops, solutions, suspensions, tablets, pills, capsules, powders, and sustained-release formulations. In some embodiments, the compositions comprise, for example, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate, and mineral oil. The compositions can additionally comprise lubricating agents, wetting agents, emulsifying and suspending agents, preserving agents, sweetening agents or flavoring agents.

The compositions can comprise an effective amount of a compound of the invention. An "effective amount" of a compound of the invention is an amount that is effective to treat a retinal degenerative disease or hearing loss associated with Usher Syndrome in a subject. The compositions can be formulated in a unit dosage form that comprises an effective amount of a compound of the invention. In some embodiments, the compositions comprise, for example, from about 1 ng to about 1,000 mg of a compound of the invention. In some embodiments, the compositions comprise from about 100 mg to about 1,000 mg of a compound of the invention. In some embodiments, the compositions comprise from about 100 mg to about 500 mg of a compound of the invention. In some embodiments, the compositions comprise from about 200 mg to about 300 mg of a compound of the invention.

The dosage of a compound of the invention can vary depending on the symptoms, age, and body weight of the subject, the nature and severity of the retinal degenerative disease or hearing loss associated with Usher Syndrome, the route of administration, and the form of the composition. The compositions described herein can be administered in a single dose or in divided doses. In some embodiments, the dosage of a compound of the invention ranges from about 0.01 ng to about 10 g per kg body mass of the subject, from about 1 ng to about 0.1 g per kg, or from about 100 ng to about 10 mg per kg.

Administration can be, for example, topical, intraaural, intraocular, parenteral, intravenous, intra-arterial, subcutaneous, intramuscular, intracranial, intraorbital, intraventricular, intracapsular, intraspinal, intracisternal, intraperitoneal, intranasal, aerosol, suppository, or oral. Formulations for oral use include tablets containing a compound of the invention in a mixture with non-toxic pharmaceutically acceptable excipients. These excipients can be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for ocular use can be in the form of eyedrops.

A compound of the invention or composition thereof can be provided in lyophilized form for reconstituting, for instance, in isotonic, aqueous, or saline buffers for parental, subcutaneous, intradermal, intramuscular, or intravenous administration. A composition of the invention can also be in the form of a liquid preparation useful for oral, intraaural, nasal, or sublingual administration, such as a suspension, syrup or elixir. A composition of the invention can also be in a form suitable for oral administration, such as a capsule, tablet, pill, and chewable solid formulation. A composition of the invention can also be prepared as a cream for dermal administration as a liquid, a viscous liquid, a paste, or a powder. A composition of the invention can also be prepared as a powder for pulmonary administration with or without an aerosolizing component.

The compositions can be in oral, intraaural, intranasal, sublingual, intraduodenal, subcutaneous, buccal, intracolonic, rectal, vaginal, mucosal, pulmonary, transdermal, intradermal, parenteral, intravenous, intramuscular and ocular dosage forms as well as being able to traverse the blood-brain barrier.

The compositions of the invention can be administered by various means known in the art. For example, the compositions of the invention can be administered orally, and can be formulated as tablets, capsules, granules, powders or syrups. Alternatively, compositions of the invention can be administered parenterally as injections (for example, intravenous, intramuscular or subcutaneous), drop infusion preparations or suppositories. For ophthalmic application compositions of the invention can be formulated as eye drops or eye ointments. Aural compositions can be formulated as ear drops, ointments, creams, liquids, gels, or salves for application to the ear, either internally or superficially. These formulations can be prepared by conventional means, and the compositions can be mixed with any conventional additive, such as an excipient, a binder, a disintegrating agent, a lubricant, a solubilizing agent, a suspension aid, an emulsifying agent, or a coating agent.

Compositions of the invention can include wetting agents, emulsifiers, and lubricants, coloring agents, release agents, coating agents, sweetening, flavoring and perfuming agents, preservatives and antioxidants.

Compositions can be suitable, for example, for oral, intraaural, intraocular, nasal, topical (including buccal and sublingual), rectal, vaginal, aerosol and/or parenteral administration. The compositions can be provided in a unit dosage form, and can be prepared by any methods known in the art.

Formulations suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia. Compositions of the invention can also be administered as a bolus, electuary, or paste.

Additional examples of pharmaceutically acceptable carriers or vehicles include: (1) fillers or extenders, such as starches, lactose, sucrose, glucose, mannitol, and/or silicic acid; (2) binders, such as carboxymethyl cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; (10) coloring agents; and (11) buffering agents. Similar compositions can be employed as fillers in soft- or hard-filled gelatin capsules.

Liquid dosage forms for oral administration include pharmaceutically acceptable emulsions, microemulsions, gels, solutions, suspensions, syrups and elixirs. The liquid dosage form can contain inert diluents commonly used in the art, for example, water or other solvents, solubilizing agents and emulsifiers, such as ethyl alcohol, isopropyl alcohol, diethyl carbonate, ethyl acetate, benzyl alcohol, benzyl benzoate, propylene glycol, 1,3-butylene glycol, oils such as, cottonseed, groundnut, corn, germ, olive, castor and sesame oils, glycerol, tetrahydrofuryl alcohol, polyethylene glycols, fatty acid esters of sorbitan, and mixtures thereof.

Suspension dosage forms can contain suspending, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The dosage forms for transdermal administration of a subject composition include drops, powders, sprays, ointments, pastes, creams, lotions, gels, solutions, and patches. The ointments, pastes, creams, and gels can contain excipients, such as animal and vegetable fats, oils, waxes, paraffin, starch, tragacanth, cellulose derivatives, polyethylene glycols, silicones, bentonite, silicic acid, talc and zinc oxide, or mixtures thereof.

Powders and sprays can contain excipients such as lactose, talc, silicic acid, aluminum hydroxide, calcium silicates, polyamide powder, or mixtures thereof. Sprays may additionally contain customary propellants, such as chlorofluorohydrocarbons and volatile unsubstituted hydrocarbons, such as butane and propane.

Compositions can be administered by aerosol of solid particles. A non-aqueous (e.g., fluorocarbon propellant) suspension could be used. Sonic nebulizers can be used because they minimize exposure to shear, which might cause degradation.

An aqueous aerosol can be made by formulating an aqueous solution or suspension of a compound of the invention with any conventional pharmaceutically acceptable carriers or vehicles such non-ionic surfactants (Tweens, Pluronics, or polyethylene glycol); proteins such as serum albumin; sorbitan esters; fatty acids; lecithin; amino acids; buffers; salts; sugars; or sugar alcohols.

Compositions suitable for parenteral administration comprise a compound of the invention and one or more pharmaceutically acceptable sterile isotonic aqueous or non-aqueous solutions, dispersions, suspensions, or emulsions, or sterile powders which can be reconstituted into sterile injectable solutions or dispersions just prior to use, which can contain antioxidants, buffers, bacteriostats, or solutes, which render the formulation isotonic with the blood of the subject, and suspending or thickening agents.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

General Synthetic Methods
Standard acidic LC-MS conditions: (10 cm_ESCI_Formic_MeCN)

A Phenomenex Luna 5 μm C18 (2), 100×4.6 mm (plus guard cartridge) column using an acetonitrile (Far UV grade) with 0.1% (V/V) formic acid: water (high purity via PureLab Option unit) with 0.1% formic acid gradient was used. The flow rate was 2 mL/min. UV detection was done using a Waters diode array detector (start Range 210 nm, end range 400 nm, range interval 4 nm). Mass detection was performed via a single quadrapole LC-MS instrument. Ionisation is either ESI or APCI dependent on compound types. The gradient used ran from 95% of aqueous solvent at time 0.00 min to 5% of aqueous solvent at 3.50 min. This percentage was then held for a further 2 min.

Standard Basic LC-MS Conditions: (10 cm_ESCI_Bicarb_MeCN):

A Waters Xterra MS 5 m C18, 100×4.6 mm (plus guard cartridge) using an acetonitrile (Far UV grade): water (high purity via PureLab Option unit) with 10 mM ammonium bicarbonate (ammonium hydrogen carbonate) gradient was used. The flow rate was 2 mL/min. UV detection was done using a Waters diode array detector (start Range 210 nm, end range 400 nm, range interval 4 nm). Mass detection was performed via a single quadrapole LC-MS instrument. Ionisation is either ESI or APCI dependent on compound types. The gradient used ran from 95% of aqueous solvent at time 0.00 min to 5% of aqueous solvent at 4.0 min. This percentage was then held for a further 1.5 min.

Standard Acidic HPLC Conditions: (10 cm_Formic_ACE 3 C18 AR_HPLC_CH3CN)

A Hichrom ACE 3 C18-AR mixed mode 100×4.6 mm column using an acetonitrile (Far UV grade) with 0.1% (V/V) formic acid: water (high purity via PureLab Option unit) with 0.1% formic acid gradient was used. The flow rate was 1 mL/min. UV detection was done using an Agilent diode array detector (300 nm, band width 200 nm; ref. 450 nm, band width 100 nm). The gradient used ran from 98% of aqueous solvent from time 0.00 min to 3.00 min, to 100% of aqueous solvent at 12.00 min. This percentage was then held for a further 2.4 min.

Standard Basic HPLC Conditions: (15 cm_Bicarb_GeminiNX_HPLC)

A Phenomenex, Gemini NX, 3 m C18, 150×4.6 mm column using an acetonitrile (Far UV grade): water (high purity via PureLab Option unit) with 10 mM ammonium bicarbonate gradient was used. The flow rate was 1 mL/min. UV detection was done using an Agilent diode array detector (300 nm, band width 200 nm; ref. 450 nm, band width 100 nm). The gradient used ran from 95.5% of aqueous solvent at time 0.00 min to 0% of aqueous solvent at 9.00 min. This percentage was then held for a further 4.5 min.

Synthetic Schemes

Non-limiting examples of synthetic schemes that are useful for synthesizing the Pyrazolopyridazine compounds include the following.

Scheme I: General Scheme for Synthesising Compounds of Formula I

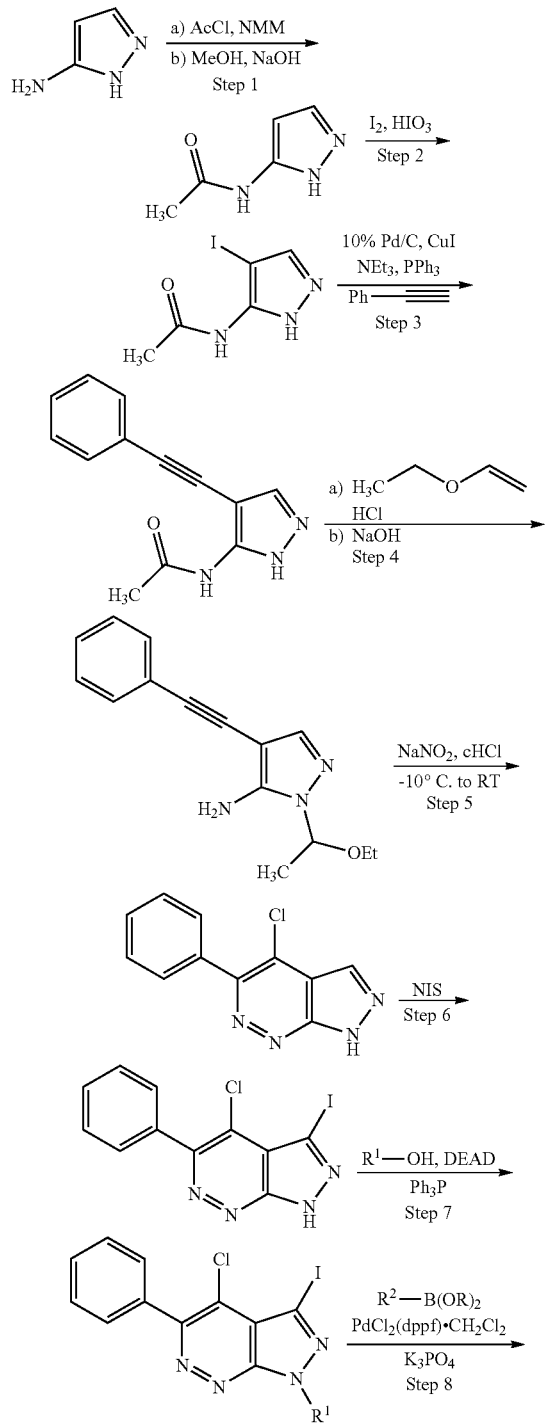

-continued

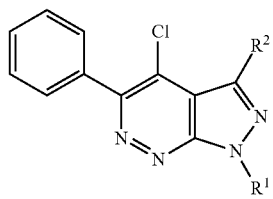

Example 1

4-chloro-3-(1-methyl-1H-pyrazol-4-yl)-1-(2-(4-methylpiperazin-1-yl)ethyl)-5-phenyl-1H-pyrazolo[3,4-c]pyridazine (Compound Ic)

Step 1: N-(1H-pyrazol-5-yl)acetamide

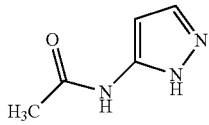

To a solution of 1H-pyrazol-5-amine (50 g, 0.602 mol) and N-methylmorpholine (160 mL, 1.44 mol) in $CH_2Cl_2$ (2 L) was added acetyl chloride (99 mL, 1.38 mol) dropwise at 0° C. under an atmosphere of nitrogen. The reaction mixture was stirred at room temperature for 1 d. Some di-acylated product was observed in an LCMS. The reaction mixture was concentrated in vacuo and the resulting solid was suspended in MeOH (2 L) and cooled to 0° C. 4 M NaOH solution (aq., 440 mL, 1.75 mol) was added slowly and the mixture allowed to warm to room temperature over 1.5 h. The MeOH was removed in vacuo and the solid was collected by filtration, washed with minimal cold water and dried in vacuo to provide the title compound as a solid (60 g).

Step 2: N-(4-iodo-1H-pyrazol-5-yl)acetamide

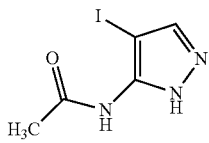

A suspension of N-(1H-pyrazol-5-yl)acetamide (60 g, 0.48 mol), iodic acid (21.1 g, 0.12 mol) and iodine (61 g, 0.24 mol) in ethanol (1.6 L) was heated at 60° C. for 1.5 h and cooled to room temperature. The reaction mixture was concentrated in vacuo and partitioned between ethyl acetate and 2 M $Na_2S_2O_3$ aq. solution. The layers were separated and the aqueous extracted with ethyl acetate. The combined organic

Step 3:
N-(4-(phenylethynyl)-1H-pyrazol-5-yl)acetamide

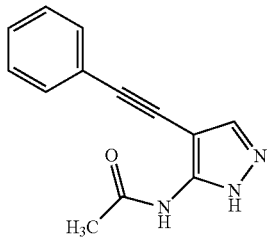 [SMILES: CC(=O)Nc1[nH]ncc1C#Cc1ccccc1]

Nitrogen was bubbled through a suspension of N-(4-iodo-1H-pyrazol-5-yl)acetamide (30 g, 120 mmol), 10% palladium on carbon (50% water, 7.4 g, 3 mmol), copper(I) iodide (1.14 g, 6 mmol), triphenylphosphine (6.3 g, 24 mmol) and triethylamine (50 mL, 360 mmol) in ethanol (600 mL) for 20 min. Phenyl acetylene was added and nitrogen bubbled through the mixture for a further 25 min. The reaction mixture was then heated and stirred under reflux conditions in an atmosphere of nitrogen for 3 d and cooled to room temperature. The reaction mixture was filtered through celite and the filtrate was concentrated in vacuo. The residue was purified by column chromatography (silica gel, iso-hexanes/ethyl acetate 9:1 to 0:1) yielding the title compound as a solid (17.6 g).

Step 4: 1-(1-ethoxyethyl)-4-(phenylethynyl)-1H-pyrazol-5-amine

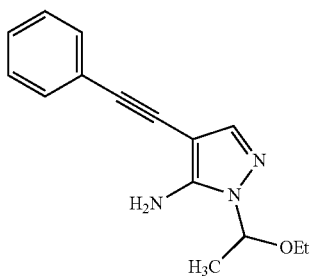 [SMILES: CCOC(C)n1ncc(C#Cc2ccccc2)c1N]

A solution of N-(4-(phenylethynyl)-1H-pyrazol-5-yl)acetamide (17.6 g, 78 mmol), ethoxyethene (11.2 mL, 117 mmol) and HCl in 1,4-dioxane (1 mL, 4 mmol) in CH$_2$Cl$_2$ (520 mL) was stirred at room temperature for 1 h and concentrated in vacuo. The residue was dissolved in ethanol (260 mL) and 25% aq. NaOH solution (260 mL) and the reaction mixture was heated to 75° C. for 4 h and cooled to room temperature. The ethanol was part concentrated in vacuo and the resulting solid collected by filtration, washed with water and minimum cold ethanol and dried in vacuo to provide the title compound as a solid (16 g).

Step 5: 4-chloro-5-phenyl-1H-pyrazolo[3,4-c]pyridazine

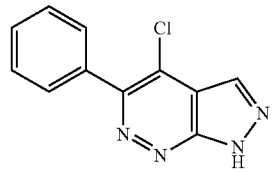 [SMILES: Clc1c(-c2ccccc2)nnc2[nH]ncc12]

Sodium nitrite (4.3 g, 63 mmol) was added to conc. HCl (314 mL) at −15° C. and stirred for 10 min. 1-(1-ethoxyethyl)-4-(phenylethynyl)-1H-pyrazol-5-amine (3 g, 31.4 mmol) was added and the mixture stirred at −10° C. for 10 min and room temperature for 1 d. The reaction mixture was cooled to 0° C. and CH$_2$Cl$_2$ (250 mL) was added. Under vigorous stirring, Na$_2$CO$_3$ (160 g) was added carefully followed by sat. aq. NaHCO$_3$ solution over a period of 2 h until the pH was 7 and there was no more foaming on further addition of base. The layers were separated and the aqueous phase was extracted with CH$_2$Cl$_2$. The combined organic layers were dried (MgSO$_4$), filtered and concentrated in vacuo. The residue was purified by column chromatography (silica gel, iso-hexanes/diethyl ether 1:0 to 0:1) yielding the title compound as a solid (3.43 g).

Step 6: 4-chloro-3-iodo-5-phenyl-1H-pyrazolo[3,4-c]pyridazine

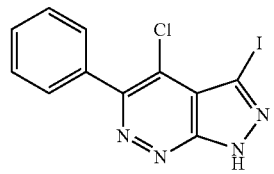 [SMILES: Clc1c(-c2ccccc2)nnc2[nH]nc(I)c12]

A suspension of 4-chloro-5-phenyl-1H-pyrazolo[3,4-c]pyridazine (2.44 g, 10.6 mmol) and N-iodosuccinimide (3.58 g, 15.9 mmol) in acetonitrile (106 mL) was heated at reflux for 1 d. The yellow solid was collected by filtration whilst warm to provide a mixture of the title compound and starting material (9:1, 4 g).

Step 7: 4-Chloro-3-iodo-1-(2-(4-methylpiperazin-1-yl)ethyl)-5-phenyl-1H-pyrazolo[3,4-c]pyridazine (Compound Ia), 4-chloro-1-(2-(4-methylpiperazin-1-yl)ethyl)-5-phenyl-1H-pyrazolo[3,4-c]pyridazine (Compound Ib) and 4-chloro-3-iodo-2-(2-(4-methylpiperazin-1-yl)ethyl)-5-phenyl-2H-pyrazolo[3,4-c]pyridazine (Compound 20)

Ia

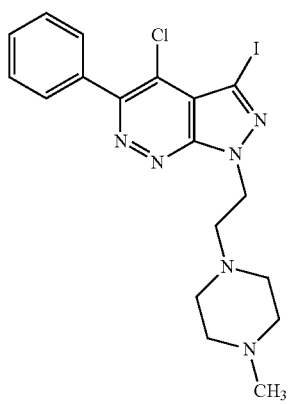

-continued

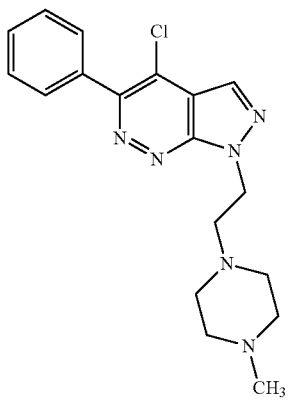

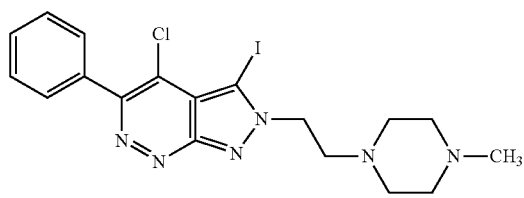

A solution of 4-chloro-3-iodo-5-phenyl-1H-pyrazolo[3,4-c]pyridazine and 4-chloro-5-phenyl-1H-pyrazolo[3,4-c]pyridazine (9:1, 1.4 g), 2-(4-methylpiperazin-1-yl)ethanol (1.13 g, 7.8 mmol), diethyl azodicarboxylate (1.37 g, 7.8 mmol) and triphenyl phosphine (2.07 g, 7.9 mmol) in 1,4-dioxane (26 mL) was heated to 85° C. for 1 h and then cooled to room temperature and concentrated in vacuo. The residue was partially purified by column chromatography (silica gel, starting with iso-hexanes/ethyl acetate 1:0 to 0:1 and finishing with ethyl acetate/4 M $NH_3$ in MeOH 1:0 to 9:1). The residue was purified by preparative HPLC to provide Compounds Ia, Ib, and 20.

4-Chloro-3-iodo-1-(2-(4-methylpiperazin-1-yl)ethyl)-5-phenyl-1H-pyrazolo[3,4-c]pyridazine (Compound Ia)

$^1$H NMR δ (ppm) ($CHCl_3$-d): 7.79-7.75 (2 H, m), 7.57-7.49 (3 H, m), 4.87 (2 H, t), 3.01 (2 H, t), 2.61 (4 H, br s), 2.34 (4 H, br s), 2.23 (3 H, s).
LCMS (10 cm_ESCI_Formic_MeCN) Rt 2.67 min; m/z 483 [M+H] 97.65% purity.

4-Chloro-1-(2-(4-methylpiperazin-1-yl)ethyl)-5-phenyl-H-pyrazolo[3,4-c]pyridazine (Compound Ib)

$^1$H NMR δ (ppm) ($CHCl_3$-d): 8.21 (1 H, s), 7.84-7.81 (2 H, m), 7.56-7.47 (3 H, m), 4.89 (2 H, t), 3.03 (2 H, t), 2.62 (4 H, br s), 2.35 (4 H, br s), 2.23 (3 H, s).
LCMS (10 cm_ESCI_Formic_MeCN) Rt 2.48 min; m/z 357 [M+H] 99.73% purity.

4-Chloro-3-iodo-2-(2-(4-methylpiperazin-1-yl)ethyl)-5-phenyl-2H-pyrazolo[3,4-c]pyridazine (Compound 20)

$^1$H NMR δ (ppm) ($CHCl_3$-d): 7.83 (2 H, m), 7.56-7.47 (3 H, m), 4.78 (2 H, t), 3.10 (2 H, t), 2.66 (4 H, br s), 2.47 (4 H, br s), 2.30 (3 H, s).
LCMS (10 cm_ESCI_Bicarb_MeCN) Rt 3.07 min; m/z 483 [M+H] 94.53% purity.

Step 8: 4-chloro-3-(1-methyl-1H-pyrazol-4-yl)-1-(2-(4-methylpiperazin-1-yl)ethyl)-5-phenyl-1H-pyrazolo[3,4-c]pyridazine (Compound Ic)

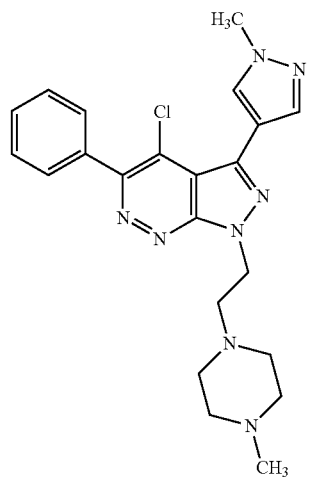 [SMILES: CN1CCN(CCn2nc(-c3cnn(C)c3)c3c(Cl)c(-c4ccccc4)nnc32)CC1]

Nitrogen was bubbled through a suspension of 4-chloro-3-iodo-1-(2-(4-methylpiperazin-1-yl)ethyl)-5-phenyl-1H-pyrazolo[3,4-c]pyridazine (75 mg, 0.16 mmol), 1-methyl-4-(4,4,5,5-tetramethyl-1,3,2-dioxaborolan-2-yl)-1H-pyrazole (37 mg, 0.18 mmol) and $K_3PO_4$ (99 mg, 0.47 mmol) in DMF (1.2 mL) and water (0.4 mL) for 20 min. 1,1'-Bis(diphenylphosphino)ferrocene-palladium(II)dichloride dichloromethane complex (13 mg, 0.016 mmol) was added and the tube sealed and heated using microwave irradiation to 60° C. for 30 min. The crude reaction mixture was filtered and purified by preparative HPLC to provide Compound Ic (42 mg).

$^1$H NMR δ (ppm) ($CHCl_3$-d): 8.00 (1 H, s), 7.89 (1 H, s), 7.78-7.75 (2 H, m), 7.56-7.47 (3 H, m), 4.89 (2 H, t), 4.00 (3 H, s), 3.04 (2 H, t), 2.70-2.58 (4 H, m), 2.44-2.30 (4 H, m), 2.24 (3 H, s).
LCMS (10 cm_ESCI_Formic_MeCN) Rt 2.47 min; m/z 437 [M+H] 98.88% purity.

Example 2

(3-(4-chloro-1-(2-(4-methylpiperazin-1-yl)ethyl)-5-phenyl-1H-pyrazolo[3,4-c]pyridazin-3-yl)phenyl)(pyrrolidin-1-yl)methanone (Compound Id)

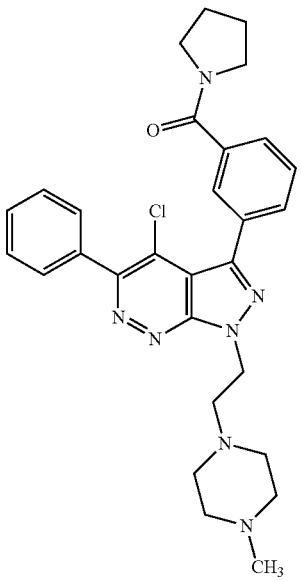 [SMILES: CN1CCN(CCn2nc(-c3cccc(C(=O)N4CCCC4)c3)c3c(Cl)c(-c4ccccc4)nnc32)CC1]

Compound Id was synthesized according to Example 1, but using (3-(pyrrolidine-1-carbonyl)phenyl)boronic acid instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.44 (1 H, t), 7.84-7.75 (3 H, m), 7.62 (1 H, dt), 7.56-7.46 (4 H, m), 4.94 (2 H, t), 3.68 (2 H, t), 3.49 (2 H, t), 3.07 (2 H, t), 2.65 (4 H, br s), 2.37 (4 H, br s), 2.24 (3 H, s), 2.01-1.85 (4 H, m).

LCMS (15 cm_Bicarb_GeminiNX_HPLC_CH3CN) Rt 9.9 min; m/z 530 [M+H] 92.56% purity.

Example 3

4-chloro-1-(2-(4-methylpiperazin-1-yl)ethyl)-5-phenyl-3-(2-(trifluoromethyl)pyridin-4-yl)-1H-pyrazolo[3,4-c]pyridazine (Compound Ie)

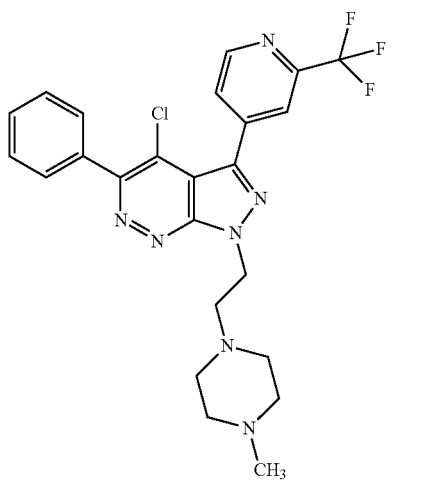 [SMILES: CN1CCN(CCn2nc(-c3ccnc(C(F)(F)F)c3)c3c(Cl)c(-c4ccccc4)nnc32)CC1]

Compound Ie was synthesized according to Example 1, but using (2-(trifluoromethyl)pyridin-4-yl)boronic acid instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 8.88 (1 H, d), 8.19 (1 H, s), 7.98 (1 H, dd), 7.81-7.77 (2 H, m), 7.57-7.51 (3 H, m), 4.99 (2 H, t), 3.12 (2 H, t), 2.80 (4 H, br s), 2.62 (4 H, br s), 2.40 (3 H, s).

LCMS (10 cm_ESCI_Formic_MeCN) Rt 2.85 min; m/z 502 [M+H] 90.64% purity.

Example 4

4-chloro-3-(3,6-dihydro-2H-pyran-4-yl)-1-(2-(4-methylpiperazin-1-yl)ethyl)-5-phenyl-1H-pyrazolo[3,4-c]pyridazine (Compound If)

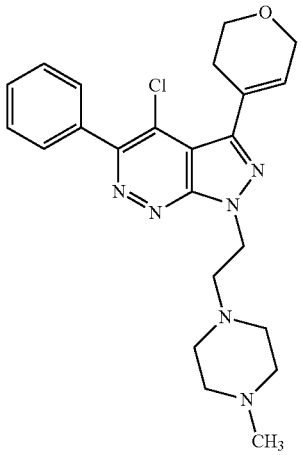 [SMILES: CN1CCN(CCn2nc(C3=CCOCC3)c3c(Cl)c(-c4ccccc4)nnc32)CC1]

Compound If was synthesized according to Example 1, but using 2-(3,6-dihydro-2H-pyran-4-yl)-4,4,5,5-tetramethyl-1,3,2-dioxaborolane instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.68-7.64 (2 H, m), 7.45-7.36 (3 H, m), 6.23-6.20 (1 H, m), 4.76 (2 H, t), 4.29 (2 H, m), 3.89 (2 H, t), 2.92 (2 H, t), 2.68-2.52 (6 H, m), 2.30 (4 H, br s), 2.17 (3 H, s).

LCMS (10 cm_Formic_ACE 3 C18 AR_HPLC_CH3CN) Rt 9.06 min; m/z 439 [M+H] 93.3% purity.

Example 5

(E)-4-chloro-1-(2-(4-methylpiperazin-1-yl)ethyl)-5-phenyl-3-styryl-1H-pyrazolo[3,4-c]pyridazine (Compound Ig)

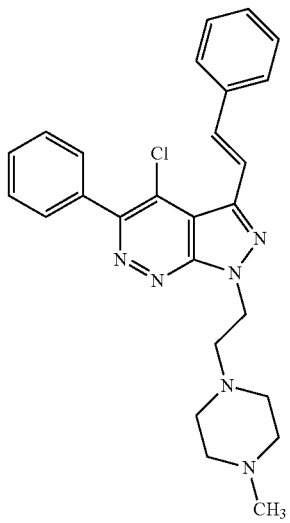 [SMILES: CN1CCN(CCn2nc(/C=C/c3ccccc3)c3c(Cl)c(-c4ccccc4)nnc32)CC1]

Compound Ig was synthesized according to Example 1, but using (E)-styrylboronic acid instead of 1-methyl-4-(4,4,5,5-tetramethyl-1,3,2-dioxaborolan-2-yl)-1H-pyrazole in Step 8.

$^1$H NMR δ (ppm) (DMSO-$d_6$): 7.85-7.75 (5 H, m), 7.70-7.56 (4 H, m), 7.52-7.45 (2 H, m), 7.44-7.38 (1 H, m), 4.92 (2 H, t), 3.01 (2 H, t), 2.57-2.54 (4 H, m), 2.32-2.20 (4 H, m), 2.15 (3 H, s).

LCMS (10 cm_ESCI_Formic_MeCN) Rt 3.01 min; m/z 459 [M+H] 96.98% purity.

Example 6

4-chloro-1-(2-(4-methylpiperazin-1-yl)ethyl)-5-phenyl-3-(6-(trifluoromethyl)pyridin-3-yl)-1H-pyrazolo[3,4-c]pyridazine (Compound Ih)

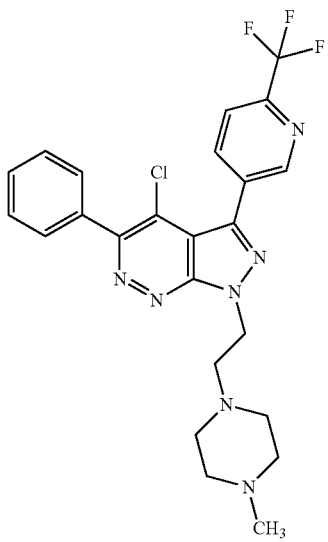 [SMILES: CN1CCN(CCn2nc(-c3ccc(C(F)(F)F)nc3)c3c(Cl)c(-c4ccccc4)nnc32)CC1]

Compound Ih was synthesized according to Example 1, but using (6-(trifluoromethyl)pyridin-3-yl)boronic acid instead of 1-methyl-4-(4,4,5,5-tetramethyl-1,3,2-dioxaborolan-2-yl)-1H-pyrazole in Step 8.

$^1$H NMR δ (ppm) (DMSO-$d_6$): 9.26 (1 H, d), 8.60 (1 H, dd), 8.17 (1 H, d), 7.82 (2 H, m), 7.67-7.58 (3 H, m), 5.01 (2 H, t), 3.04 (2 H, t), 2.57-2.54 (4 H, br s), 2.76 (4 H, br s), 2.15 (3 H, s).

LCMS (10 cm_ESCI_Formic_MeCN) Rt 2.86 min; m/z 502 [M+H] 97.31% purity.

Example 7

(E)-4-chloro-3-(3-methoxyprop-1-en-1-yl)-1-(2-(4-methylpiperazin-1-yl)ethyl)-5-phenyl-1H-pyrazolo[3,4-c]pyridazine (Compound Ii)

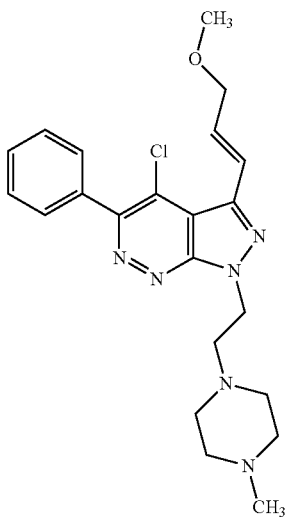 [SMILES: COC/C=C/c1nn(CCN2CCN(C)CC2)c2nnc(-c3ccccc3)c(Cl)c12]

Compound Ii was synthesized according to Example 1, but using (E)-2-(3-methoxyprop-1-en-1-yl)-4,4,5,5-tetramethyl-1,3,2-dioxaborolane instead of 1-methyl-4-(4,4,5,5-tetramethyl-1,3,2-dioxaborolan-2-yl)-1H-pyrazole in Step 8.

$^1$H NMR δ (ppm) (DMSO-$d_6$): 7.80-7.77 (2 H, m), 7.67-7.57 (3 H, m), 7.23 (1 H, dt), 6.80 (1 H, dt), 4.88 (2 H, t), 4.21 (2 H, dd), 3.40 (3 H, s), 2.97 (2 H, t), 2.57-2.54 ((4H), 2.24 (4 H, br s), 2.14 (3 H, s).

LCMS (10 cm_ESCI_Formic_MeCN) Rt 2.68 min; m/z 427 [M+H] 96.83% purity.

Example 8

3-(benzofuran-2-yl)-4-chloro-1-(2-(4-methylpiperazin-1-yl)ethyl)-5-phenyl-1H-pyrazolo[3,4-c]pyridazine (Compound Ij)

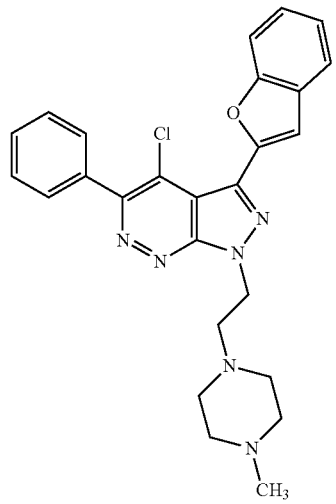 [SMILES: CN1CCN(CCn2nc(-c3cc4ccccc4o3)c3c(Cl)c(-c4ccccc4)nnc32)CC1]

Compound Ij was synthesized according to Example 1, but using benzofuran-2-ylboronic acid instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.83 (2 H, m), 7.72 (1 H, d), 7.64 (1 H, d), 7.57 (3 H, m), 7.50 (1 H, s), 7.42 (1 H, t), 7.33 ((1 H, t), 5.02 (2 H, t), 3.12 (2 H, t), 2.68 (4 H, br s), 2.40 (4 H, br s), 2.26 ((3 H, s).

LCMS (10 cm_Formic_ACE 3 C18 AR_HPLC_CH3CN) Rt 10.39 min; m/z 473 [M+H] 93.83% purity.

Example 9

4-chloro-3-(1-methyl-1H-pyrrol-2-yl)-1-(2-(4-methylpiperazin-1-yl)ethyl)-5-phenyl-1H-pyrazolo[3,4-c]pyridazine (Compound Ik)

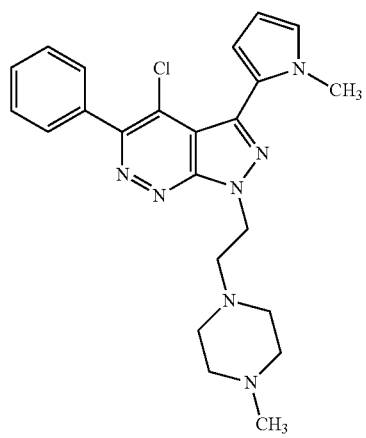 [SMILES: CN1CCN(CCn2nc(-c3cccn3C)c3c(Cl)c(-c4ccccc4)nnc32)CC1]

Compound Ik was synthesized according to Example 1, but using 1-methyl-2-(4,4,5,5-tetramethyl-1,3,2-dioxaborolan-2-yl)-1H-pyrrole instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.78 (2 H, m), 7.55-7.49 (3 H, m), 6.82 (1 H, t), 6.58 (1 H, dd), 6.26 (1 H, dd), 4.91 (2 H, t), 3.71 (3 H, s), 3.08 (2 H, t), 2.74 (4 H, br s), 2.52 (4 H, br s), 2.34 (3 H, s).

LCMS (10 cm_ESCI_Formic_MeCN) Rt 2.79 min; m/z 436 [M+H] 96.5% purity.

Example 10

4-chloro-3-(2,3-dihydrobenzofuran-5-yl)-1-(2-(4-methylpiperazin-1-yl)ethyl)-5-phenyl-1H-pyrazolo[3,4-c]pyridazine (Compound Il)

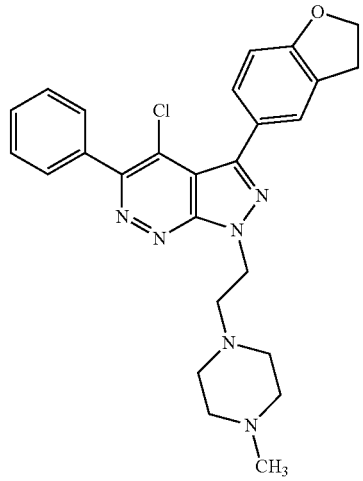 [SMILES: CN1CCN(CCn2nc(-c3ccc4c(c3)CCO4)c3c(Cl)c(-c4ccccc4)nnc32)CC1]

Compound Il was synthesized according to Example 1, but using (2,3-dihydrobenzofuran-5-yl)boronic acid instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.78-7.75 (2 H, m), 7.58 (1 H, s), 7.54-7.47 (4 H, m), 6.90 (1 H, d), 4.91 (2 H, t), 4.66 (2 H, t), 3.30 (2 H, t), 3.08 (2 H, t), 2.72 (4 H, br s), 2.50 (4 H, br s), 2.32 (3 H, s).

LCMS (10 cm_Formic_ACE 3 C18 AR_HPLC_CH3CN) Rt 9.86 min; m/z 475 [M+H] 96.92% purity.

Example 11

4-chloro-3-(1H-indol-2-yl)-1-(2-(4-methylpiperazin-1-yl)ethyl)-5-phenyl-1H-pyrazolo[3,4-c]pyridazine (Compound Im)

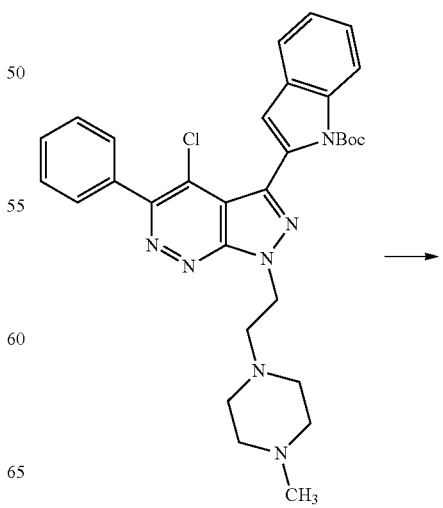

-continued

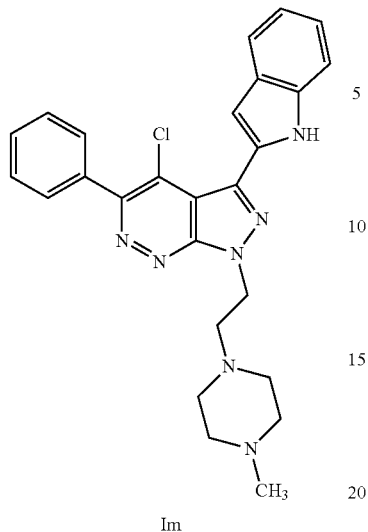

Im

Tert-butyl 2-(4-chloro-1-(2-(4-methylpiperazin-1-yl)ethyl)-5-phenyl-1H-pyrazolo[3,4-c]pyridazin-3-yl)-1H-indole-1-carboxylate was synthesized according to Example 1, but using (1-(tert-butoxycarbonyl)-1H-indol-2-yl)boronic acid instead of 1-methyl-4-(4,4,5,5-tetramethyl-1,3,2-dioxaborolan-2-yl)-1H-pyrazole in Step 8 which was deprotected to yield Compound Im as follows.

A solution of tert-butyl 2-(4-chloro-1-(2-(4-methylpiperazin-1-yl)ethyl)-5-phenyl-1H-pyrazolo[3,4-c]pyridazin-3-yl)-1H-indole-1-carboxylate (29 mg, 0.051 mmol) in $CH_2Cl_2$ (3 mL) and trifluoroacetic acid (0.8 mL) was stirred at room temperature for 1 d. Solid $NaHCO_3$ was added until no gas was evolved and sat. aq. $NaHCO_3$ solution and $CH_2Cl_2$ was added. The layers were separated and the aqueous was extracted with $CH_2Cl_2$, the combined organics were dried ($MgSO_4$), filtered and concentrated in vacuo. The residue was freeze dried from acetonitrile and water to provide Compound Im as a solid.

$^1$H NMR δ (ppm) ($CHCl_3$-d): 9.14 (1 H, s), 7.79 (2 H, m), 7.70 (1 H, d), 7.60-7.50 (3 H, m), 7.49-7.42 (2 H, m), 7.29 (1 H, t), 7.15 (1H, t), 4.92 (2 H, t), 3.14 (2 H, t), 2.87 (8 H, br s), 2.56 (3 H, s).

LCMS (10 cm_ESCI_Bicarb_MeCN) Rt 3.68 min; m/z 472 [M+H] 95.85% purity.

Example 12

2-(4-chloro-3-(cyclopent-1-en-1-yl)-5-phenyl-1H-pyrazolo[3,4-c]pyridazin-1-yl)-1-(pyrrolidin-1-yl)ethanone (Compound In)

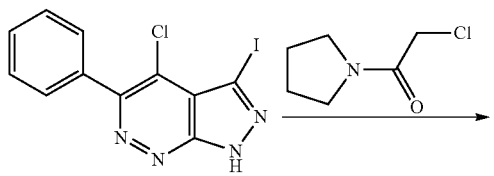

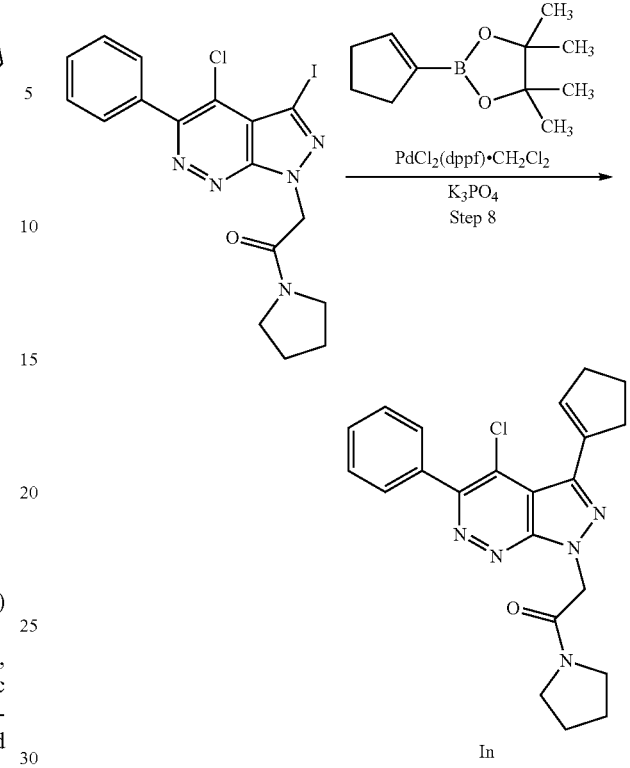

In

4-Chloro-3-iodo-5-phenyl-1H-pyrazolo[3,4-c]pyridazine was synthesized according to Example 1 through step 6. Sodium hydride (60% in mineral oil, 32 mg, 1.75 mmol) was added to a solution of 4-chloro-3-iodo-5-phenyl-1H-pyrazolo[3,4-c]pyridazine (400 mg, 1.12 mmol) and 2-chloro-1-(pyrrolidin-1-yl)ethanone (54 mg, 1.8 mmol) in dry DMF (7.5 mL) at room temperature. After 1.5 h at room temperature further sodium hydride (60% in mineral oil, 27 mg) was added and the suspension stirred for 2 h. 4% LiCl aq. solution and ethyl acetate was added. The layers were separated and the aqueous was extracted with ethyl acetate. The combined organics were dried ($MgSO_4$), filtered and concentrated in vacuo. The residue was partially purified by column chromatography (silica gel, iso-hexanes/ethyl acetate 1:0 to 0:1). The resulting solid was dissolved in minimum $CH_2Cl_2$ and diethyl ether was added until a solid precipitated. The solid was collected by filtration to provide 2-(4-chloro-3-iodo-5-phenyl-1H-pyrazolo[3,4-c]pyridazin-1-yl)-1-(pyrrolidin-1-yl)ethanone (246 mg).

Compound In was synthesized according to Example 1 Step 8, except 2-(4-chloro-3-iodo-5-phenyl-1H-pyrazolo[3,4-c]pyridazin-1-yl)-1-(pyrrolidin-1-yl)ethanone was used instead of 4-chloro-3-iodo-1-(2-(4-methylpiperazin-1-yl)ethyl)-5-phenyl-1H-pyrazolo[3,4-c]pyridazine and 2-(cyclopent-1-en-1-yl)-4,4,5,5-tetramethyl-1,3,2-dioxaborolane was used instead of 1-methyl-4-(4,4,5,5-tetramethyl-1,3,2-dioxaborolan-2-yl)-1H-pyrazole.

$^1$H NMR δ (ppm) ($CHCl_3$-d): 7.73 (2 H, m), 7.54-7.47 (3 H, m), 6.58 (1 H, m), 5.48 (2 H, s), 3.63 (2 H, t), 3.52 (2 H, t), 2.96 (2 H, m), 2.65-2.59 (2 H, m), 2.11-2.01 (4 H, m), 1.94-1.87 (2 H, m).

LCMS (10 cm_ESCI_Formic_MeCN) Rt 4.52 min; m/z 408 [M+H] 97.97% purity.

Example 13

4-chloro-3-(5-methyl-2-furyl)-1-[2-(4-methylpiperazin-1-yl)ethyl]-5-phenyl-pyrazolo[3,4-c]pyridazine (Compound Io)

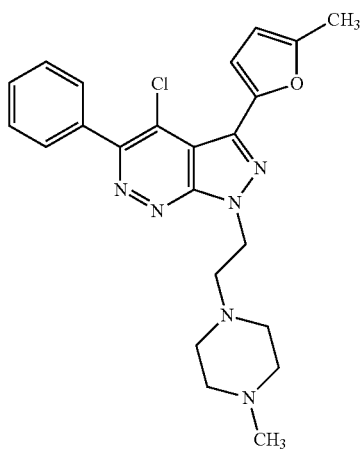 [SMILES: Cc1ccc(-c2nn(CCN3CCN(C)CC3)c3nnc(-c4ccccc4)c(Cl)c23)o1]

Compound Io was synthesized according to Example 1, but using (5-methyl-2-furyl)boronic acid instead of 1-methyl-4-(4,4,5,5-tetramethyl-1,3,2-dioxaborolan-2-yl)-1H-pyrazole in Step 8.

¹H NMR δ (ppm) (CHCl₃-d): 7.79-7.76 (2 H, m), 7.55-7.49 (3 H, m), 6.97 (1 H, d), 6.17 (1 H, d), 4.92 (2 H, t), 3.05 (2 H, t), 2.64 (4 H, bs), 2.44 (3 H, s), 2.36 (4 H, bs), 2.24 (3H, s).

LCMS (10 cm_ESCI_Bicarb_MeCN) Rt 3.87 min; m/z 437 [M+H] 96.26% purity.

Example 14

4-chloro-1-[2-[(3R)-3-fluoropyrrolidin-1-yl]ethyl]-3-iodo-5-phenyl-pyrazolo[3,4-c]pyridazine (Compound Ip)

Step 1: 2-[(3R)-3-fluoropyrrolidin-1-yl]ethanol

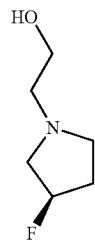

2-[(3R)-3-fluoropyrrolidin-1-yl]ethanol was synthesized as followed: a suspension of (3R)-3-fluoropyrrolidine hydrochloride (1 g, 8 mmol) in CH₂Cl₂ was cooled to 0° C. Triethylamine (2.79 mL, 20 mmol) and methyl bromoacetate (0.83 mL, 8.8 mmol) were added and the reaction mixture was stirred at room temperature for 16 h. The reaction mixture was diluted with CH₂Cl₂ and water. The layers were separated and the aqueous layer was extracted with CH₂Cl₂. The combined organic phases were dried (phase separator cartridge) and concentrated in vacuo, yielding methyl 2-[(3R)-3-fluoropyrrolidin-1-yl]acetate, which was used in the next step without further purification (1.29 g). A solution of lithium aluminium hydride in THF (2 M, 8 mL, 6 mmol) was slowly added to a solution of methyl 2-[(3R)-3-fluoropyrrolidin-1-yl]acetate (1.29 g, 8 mmol) in THF (72 mL). The reaction mixture was stirred at 70° C. for 2 h. The reaction mixture was cooled to 0° C. and ice-cold 10% KOH aqueous solution was added slowly. The reaction mixture was filtered and the solid was washed with 10% KOH aqueous solution and hot ethyl acetate. The layers were separated and the aqueous was extracted with ethyl acetate. The combined organics were dried (MgSO₄), filtered and concentrated in vacuo, yielding 2-[(3R)-3-fluoropyrrolidin-1-yl]ethanol as an oil (779 mg).

Step 2: 4-chloro-1-[2-[(3R)-3-fluoropyrrolidin-1-yl]ethyl]-3-iodo-5-phenyl-pyrazolo[3,4-c]pyridazine (Compound Ip)

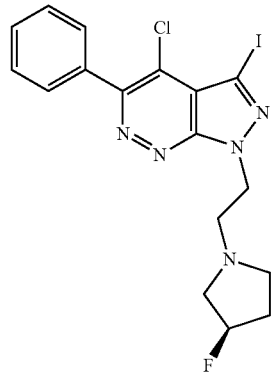 [SMILES: F[C@@H]1CCN(CCn2nc(I)c3c(Cl)c(-c4ccccc4)nnc32)C1]

Compound Ip was synthesized according to Example 1, Step 7, but using 2-[(3R)-3-fluoropyrrolidin-1-yl]ethanol instead of 2-(4-methylpiperazin-1-yl)ethanol in Step 7. ¹H NMR δ (ppm) (CHCl₃-d): 7.78-7.74 (2 H, m), 7.57-7.47 (3 H, m), 5.18-5.01 (1 H, m), 4.91-4.84 (2 H, m), 3.23-3.15 (2 H, m), 2.99-2.85 (3 H, m), 2.66 (1 H, q), 2.09-1.95 (2 H, m).

LCMS (10 cm_ESCI_Formic_MeCN) Rt 2.65 min; m/z 472 [M+H] 94.21% purity.

Example 15

4-chloro-3-(3,6-dihydro-2H-pyran-4-yl)-1-[2-[(3R)-3-fluoropyrrolidin-1-yl]ethyl]-5-phenyl-pyrazolo[3,4-c]pyridazine (Compound Iq)

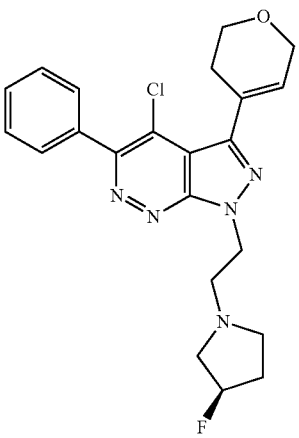 [SMILES: F[C@@H]1CCN(CCn2nc(C3=CCOCC3)c3c(Cl)c(-c4ccccc4)nnc32)C1]

Compound Iq was synthesized according to Example 1, but using 2-(3,6-dihydro-2H-pyran-4-yl)-4,4,5,5-tetramethyl-1,3,2-dioxaborolane instead of 1-methyl-4-(4,4,5,5-tetramethyl-1,3,2-dioxaborolan-2-yl)-1H-pyrazole and 4-chloro-1-[2-[(3R)-3-fluoropyrrolidin-1-yl]ethyl]-3-iodo-5-phenyl-pyrazolo[3,4-c]pyridazine instead of 4-chloro-3-iodo-1-(2-(4-methylpiperazin-1-yl)ethyl)-5-phenyl-1H-pyrazolo[3,4-c]pyridazine in Step 8.

¹H NMR δ (ppm) (CHCl₃-d): 7.77-7.73 (2 H, m), 7.55-7.46 (3 H, m), 6.33-6.31 (1 H, m), 5.22-5.04 (1 H, m), 4.88 (2 H, t), 4.39 (2 H, q), 3.99 (2 H, t), 3.20 (2 H, t), 2.98-2.89 (3 H, m), 2.76-2.63 (3 H, m), 2.12-1.93 (2 H, m).

LCMS (15 cm_Bicarb_GeminiNX_HPLC_CH3CN) Rt 10.56 min; m/z 428 [M+H] 90.43% purity.

Example 16

4-chloro-3-iodo-5-phenyl-1-(2-pyrrolidin-1-ylethyl)pyrazolo[3,4-c]pyridazine (Compound Ir)

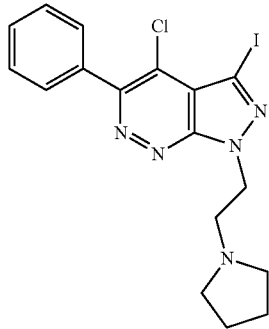 [SMILES: Clc1c(-c2ccccc2)nnc2c1c(I)nn2CCN1CCCC1]

Compound Ir was synthesized according to Example 1 through Step 7, using 2-pyrrolidin-1-ylethanol instead of 2-(4-methylpiperazin-1-yl)ethanol in Step 7.

¹H NMR δ (ppm) (CHCl₃-d): 7.79-7.75 (2 H, m), 7.57-7.49 (3 H, m), 4.89 (2 H, t), 3.14 (2 H, t), 2.66-2.60 (4 H, m), 1.76-1.71 (4 H, m).

LCMS (10 cm_ESCI_Formic_MeCN) Rt 2.66 min; m/z 454 [M+H] 99.44% purity.

Example 17

4-chloro-3-(3,6-dihydro-2H-pyran-4-yl)-5-phenyl-1-(2-pyrrolidin-1-ylethyl)pyrazolo[3,4-c]pyridazine (Compound Is)

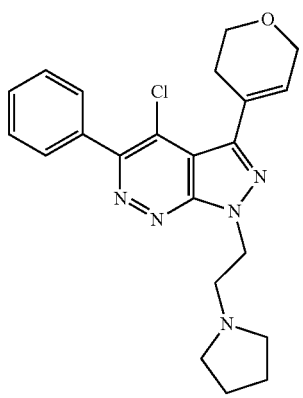 [SMILES: Clc1c(-c2ccccc2)nnc2c1c(C1=CCOCC1)nn2CCN1CCCC1]

Compound Is was synthesized according to Example 1, using 2-(3,6-dihydro-2H-pyran-4-yl)-4,4,5,5-tetramethyl-1,3,2-dioxaborolane instead of 1-methyl-4-(4,4,5,5-tetramethyl-1,3,2-dioxaborolan-2-yl)-1H-pyrazole and 4-chloro-3-iodo-5-phenyl-1-(2-pyrrolidin-1-ylethyl)pyrazolo[3,4-c]pyridazine instead of 4-chloro-3-iodo-1-(2-(4-methylpiperazin-1-yl)ethyl)-5-phenyl-1H-pyrazolo[3,4-c]pyridazine in Step 8.

¹H NMR δ (ppm) (CHCl₃-d): 7.76-7.73 (2 H, m), 7.55-7.46 (3 H, m), 6.36-6.27 (1H, m), 4.89 (2 H, t), 4.40-4.37 (2 H, m), 3.99 (2 H, t), 3.17 (2 H, t), 2.75-2.63 (6 H, m), 1.77 (4 H, bs).

LCMS (10 cm_ESCI_Bicarb_MeCN) Rt 3.58 min; m/z 410 [M+H] 99.45% purity.

Example 18

2-(4-chloro-3-iodo-5-phenyl-pyrazolo[3,4-c]pyridazin-1-yl)-1-[(3R)-3-fluoropyrrolidin-1-yl]ethanone (Compound It)

Step 1:
2-chloro-1-[(3R)-3-fluoropyrrolidin-1-yl]ethanone

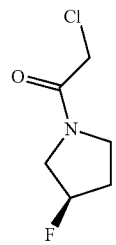

Chloroacetyl chloride (632 μL, 7.94 mmol) was added dropwise to a solution of (3R)-3-fluoropyrrolidine (1 g, 7.94 mmol) and triethylamine (2.2 mL, 15.9 mmol) in CH₂Cl₂ (20 mL) at 5° C. The reaction mixture was stirred at room temperature for 1 h. Water and CH₂Cl₂ were added. The layers were separated and the aqueous was extracted with CH₂Cl₂. The combined organics were dried (MgSO₄), filtered and concentrated in vacuo, to yield 2-chloro-1-[(3R)-3-fluoropyrrolidin-1-yl]ethanone (4.7 g).

Step 2: 2-(4-chloro-3-iodo-5-phenyl-pyrazolo[3,4-c]pyridazin-1-yl)-1-[(3R)-3-fluoropyrrolidin-1-yl]ethanone (Compound It)

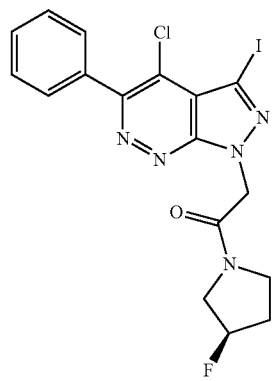 [SMILES: O=C(Cn1nc(I)c2c(Cl)c(-c3ccccc3)nnc21)N1CC[C@@H](F)C1]

Sodium hydride (60% in mineral oil, 240 mg, 6 mmol) was added to a solution of 4-chloro-3-iodo-5-phenyl-1H-pyrazolo[3,4-c]pyridazine (1.06 g, 3 mmol) and 2-chloro-1-[(3R)-3-fluoropyrrolidin-1-yl]ethanone (740 mg, 4.5 mmol) in dry DMF (20 mL) at room temperature. The reaction mixture was stirred at room temperature for 16 h. 4% LiCl aq. solution and ethyl acetate was added. The layers were separated and the aqueous was extracted with ethyl acetate. The combined organics were dried (MgSO$_4$), filtered and concentrated in vacuo. The residue was partially purified by column chromatography (silica gel, isohexane/ethyl acetate 1:0 to 3:7). The resulting solid was dissolved in minimum CH$_2$Cl$_2$ and diethyl ether was added until a solid precipitated. The solid was collected by filtration to provide Compound It as a solid (846 mg).

$^1$H NMR δ (ppm) (CHCl$_3$-d): 7.76-7.72 (2 H, m), 7.56-7.49 (3 H, m), 5.61-5.45 (2 H, m), 5.36-5.20 (1 H, m), 3.97-3.75 (3 H, m), 3.67-3.53 (1 H, m), 2.55-1.90 (1 H, m).

LCMS (15 cm_Bicarb_GeminiNX_HPLC_CH3CN) Rt 10.21 min; m/z 486 [M+H] 95.11% purity.

Scheme II: Additional General Scheme for Synthesising Compounds of Formula I

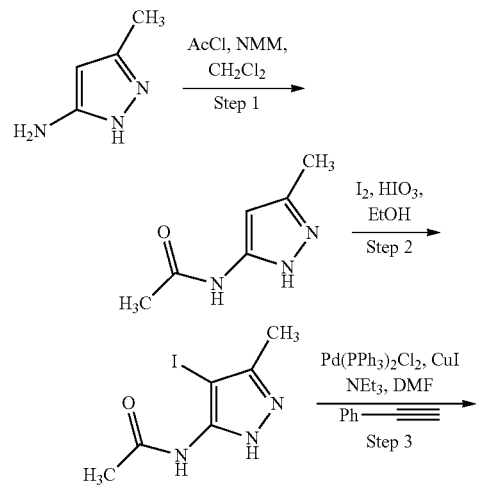

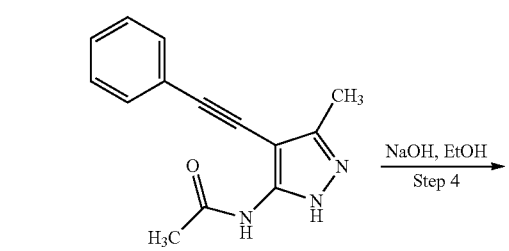

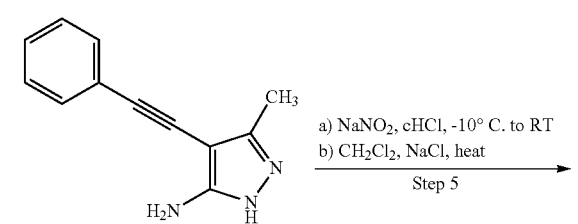

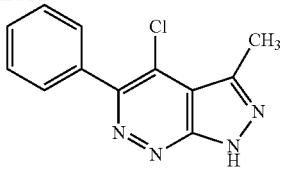

Example 19

4-chloro-3-methyl-5-phenyl-1H-pyrazolo[3,4-c]pyridazine (Compound Iu)

Step 1: N-(3-methyl-1H-pyrazol-5-yl)acetamide

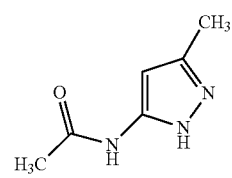

Acetyl chloride (41 g, 0.530 mol) was added dropwise to a solution of 3-methyl-1H-pyrazol-5-amine (25.6 g, 0.264 mol) and N-methylmorpholine (58 mL, 0.530 mol) in CH$_2$Cl$_2$ (250 mL) at 0° C. under an atmosphere of nitrogen. The reaction mixture was stirred at room temperature for 16 h. Water was added to the reaction mixture and the organic layer concentrated in vacuo. The residue was taken up in a mixture of MeOH/THF (100 mL/100 mL), cooled to 10° C. and treated with 1M NaOH solution. The reaction mixture was stirred for 0.25 h, acidified to pH 5 and organic solvents were removed in vacuo. The resulting precipitate was filtered, washed (water, diethyl ether) and dried to provide the title compound as a white solid (29.6 g).

Step 2: N-(4-iodo-3-methyl-1H-pyrazol-5-yl)acetamide

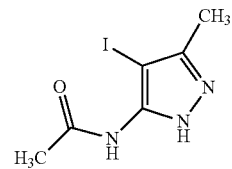

A suspension of N-(3-methyl-1H-pyrazol-5-yl)acetamide (29.6 g, 0.213 mol), iodic acid (9.3 g, 0.053 mol) and iodine (32.5 g, 0.128 mol) in ethanol (300 mL) was heated at 50° C. for 3 h and cooled to room temperature. The reaction mixture was concentrated in vacuo and taken up in ethyl acetate. The solution was washed twice with 2 M Na$_2$S$_2$O$_3$ followed by brine solution. The organic layer was dried (magnesium sulphate), filtered and concentrated in vacuo. The residue was triturated from diethyl ether, filtered and dried to provide the title compound as a white solid (32.5 g).

Step 3: N-(3-methyl-4-(phenylethynyl)-1H-pyrazol-5-yl)acetamide

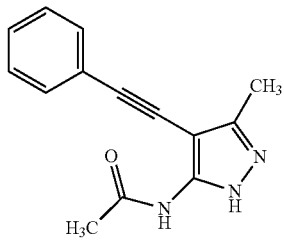 [SMILES: CC(=O)Nc1[nH]nc(C)c1C#Cc1ccccc1]

Nitrogen was bubbled through a mixture of N-(4-iodo-3-methyl-1H-pyrazol-5-yl)acetamide (32.5 g, 0.122 mol), phenylacetylene (25.0 g, 0.245 mol), triethylamine (300 mL) and DMF (100 mL) for 15 min. Copper iodide (2.3 g, 12 mmol) and bis(triphenylphosphine)palladium(II) dichloride (4.2 g, 6.0 mmol) were added and the reaction mixture stirred at 90° C. under nitrogen for 3 h. The reaction mixture was cooled to room temperature, diluted with ethyl acetate and water. The organic phase was washed with water and brine, dried (MgSO$_4$), filtered and concentrated in vacuo. The residue was purified by column chromatography (silica gel, isohexane/ethyl acetate 5:1 to 1:1) yielding the title compound as a solid (15 g).

Step 4: 3-methyl-4-(phenylethynyl)-1H-pyrazol-5-amine

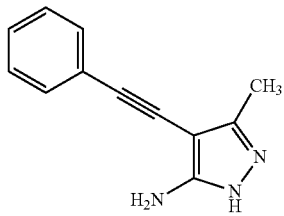

A mixture of N-(3-methyl-4-(phenylethynyl)-1H-pyrazol-5-yl)acetamide (15 g, 63 mmol), ethanol (50 mL) and 25% aq. NaOH solution (50 mL) was stirred at 90° C. for 1 h and cooled to room temperature. The reaction mixture was diluted with ethyl acetate and water. The organic phase was washed with water and brine, dried (phase separator cartridge) and concentrated in vacuo. Diethyl ether was added to the residue and the solid was collected by filtration, washed with diethyl ether and dried in vacuo to provide the title compound as a solid (3.3 g).

Step 5: 4-chloro-3-methyl-5-phenyl-1H-pyrazolo[3,4-c]pyridazine (Compound Iu)

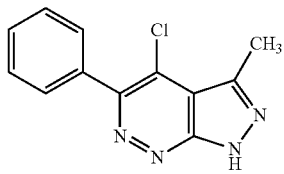 [SMILES: Cc1n[nH]c2nnc(-c3ccccc3)c(Cl)c12]

Sodium nitrite (2.3 g, 33.8 mmol) was added portionwise to cHCl (33 mL) at −15° C. and stirred for 15 min. 3-methyl-4-(phenylethynyl)-1H-pyrazol-5-amine (3.3 g, 16.9 mmol) was added as a solid, followed by the addition of CH$_2$Cl$_2$ (5 mL). The reaction mixture was allowed to warm up and stirred at room temperature for 1 h. The reaction mixture was diluted with CH$_2$Cl$_2$ (28 mL) and NaCl (1.0 g) was added. The reaction mixture was heated to 50° C. for 16 h, then cooled to room temperature and partitioned between water and CH$_2$Cl$_2$. The organic layer was washed with water and brine, dried (phase separator cartridge) and concentrated in vacuo. The residue was purified by column chromatography (silica gel, CH$_2$Cl$_2$, then CH$_2$Cl$_2$/ethyl acetate 9:1) yielding Compound Iu as a light yellow solid (1.9 g).

$^1$H NMR δ (ppm) (CHCl$_3$-d): 11.79 (1 H, s), 7.80-7.77 (2 H, m), 7.57-7.48 (3 H, m).

LCMS (15 cm_Bicarb_GeminiNX_HPLC_CH3CN) Rt 9.56 min; m/z 245 [M+H] 95.61% purity.

Example 20

General Procedure for Mitsunobu Reaction

A mixture of 4-chloro-3-methyl-5-phenyl-1H-pyrazolo[3,4-c]pyridazine (0.33 mmol), the alcohol (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide the title compound.

Example 21

4-chloro-3-methyl-1-[2-4-methylpiperazin-1-yl)ethyl]-5-phenyl-pyrazolo[3,4-c]pyridazine (Compound Iv)

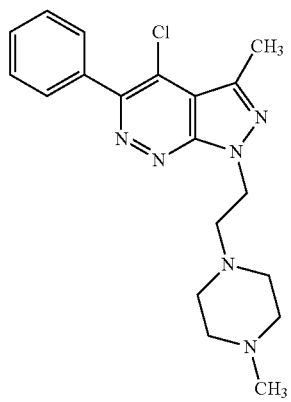 [SMILES: Cc1nn(CCN2CCN(C)CC2)c2nnc(-c3ccccc3)c(Cl)c12]

Compound Iv was synthesized from 4-chloro-3-methyl-5-phenyl-1H-pyrazolo[3,4-c]pyridazine and 2-(4-methylpiperazin-1-yl)ethanol following the general procedure for the Mitsunobu reaction described above.

$^1$H NMR δ (ppm) (CHCl$_3$-d): 7.80-7.77 (2 H, m), 7.56-7.48 (3 H, m), 4.80 (2 H, t), 2.99 (2 H, t), 2.80 (3 H, s), 2.64 (4 H, br s), 2.40 (4 H, br s), 2.26 (3 H, s).

LCMS (10 cm_ESCI_Formic_MeCN) Rt 2.53 min; m/z 371 [M+H] 99.25% purity.

Example 22

2-(4-chloro-3-methyl-5-phenyl-pyrazolo[3,4-c]pyridazin-1-yl)-1-pyrrolidin-1-yl-ethanone (Compound Iw)

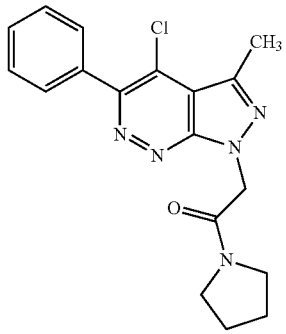 [SMILES: Cc1nn(CC(=O)N2CCCC2)c2nnc(-c3ccccc3)c(Cl)c12]

Compound Iw was synthesized from 4-chloro-3-methyl-5-phenyl-1H-pyrazolo[3,4-c]pyridazine and 2-hydroxy-1-(pyrrolidin-1-yl)ethanone following the general procedure for the Mitsunobu reaction described above.

$^1$H NMR δ (ppm) (CHCl$_3$-d): 7.78-7.74 (2 H, m), 7.54-7.50 (3 H, m), 5.44 (2 H, s), 3.63 (2 H, t), 3.52 (2 H, t), 2.81 (3 H, s), 2.07 (2 H, q), 1.90 (2 H, q).

LCMS (10 cm_ESCI_Bicarb_MeCN) Rt 3.15 min; m/z 356 [M+H] 98.98% purity.

Example 23

4-chloro-3-cyclopropyl-1-(2-methylsulfonylethyl)-5-phenyl-pyrazolo[3,4-c]pyridazine (Compound Ix)

Step 1: 4-Chloro-3-cyclopropyl-5-phenyl-1H-pyrazolo[3,4-c]pyridazine

4-Chloro-3-cyclopropyl-5-phenyl-1H-pyrazolo[3,4-c]pyridazine was synthesized according to Example 19, except using 3-cyclopropyl-1H-pyrazol-5-amine instead of 3-methyl-1H-pyrazol-5-amine.

Step 2: 4-chloro-3-cyclopropyl-1-(2-methylsulfonylethyl)-5-phenyl-pyrazolo[3,4-c]pyridazine (Compound Ix)

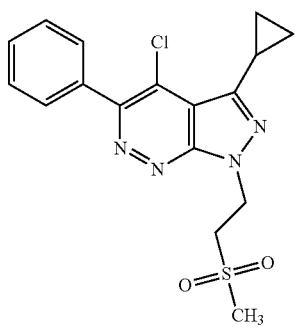 [SMILES: CS(=O)(=O)CCn1nc(C2CC2)c2c(Cl)c(-c3ccccc3)nnc21]

Compound Ix was synthesized from 4-chloro-3-cyclopropyl-5-phenyl-1H-pyrazolo[3,4-c]pyridazine and 2-(methylsulfonyl)ethanol following the general procedure for the Mitsunobu reaction as described above.

$^1$H NMR δ (ppm) (CHCl$_3$-d): 7.78-7.75 (2 H, m), 7.57-7.50 (3 H, m), 5.13 (2 H, t), 3.76 (2 H, t), 2.98 (3 H, s), 2.60-2.55 (1 H, m), 1.16-1.10 (4 H, m).

LCMS (10 cm_ESCI_Bicarb_MeCN) Rt 3.37 min; m/z 377 [M+H] 99.7% purity.

Example 24

4-chloro-1-[2-(4-methylpiperazin-1-yl)ethyl]-5-phenyl-3-(2-pyridyl)pyrazolo[3,4-c]pyridazine (Compound Iy)

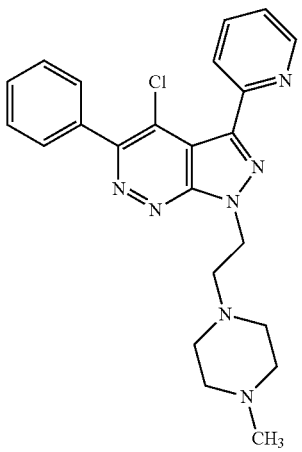 [SMILES: CN1CCN(CCn2nc(-c3ccccn3)c3c(Cl)c(-c4ccccc4)nnc32)CC1]

Nitrogen was bubbled through a mixture of 4-chloro-3-iodo-1-(2-(4-methylpiperazin-1-yl)ethyl)-5-phenyl-1H-pyrazolo[3,4-c]pyridazine (100 mg, 0.21 mmol) in DMF (1.4 mL) for 10 min. Tetrakis(triphenylphosphine)palladium (24 mg, 0.021 mmol) was added and nitrogen was bubbled in the resulting mixture for another 10 min. 2-(Tributylstannyl)pyridine was added and nitrogen was bubbled for another 10 min. The tube was sealed and heated using microwave irradiation to 100° C. for 1 h, 120° C. for 1 h, 130° C. for 2 h, then to 140° C. for 3 h. The crude reaction mixture was filtered and partially purified by preparative HPLC. The residue was dissolved in DMSO (2 mL) and water was added. The solid was filtered off, washed with water and dried to provide Compound Iy as a solid (10 mg).

$^1$H NMR δ (ppm) (CHCl$_3$-d): 8.81-8.77 (1 H, m), 7.90-7.78 (4 H, m), 7.55-7.46 (3 H, m), 7.39 (1 H, m), 4.97 (2 H, t, J=6.7 Hz), 3.08 (2 H, t, J=6.7 Hz), 2.70-2.55 (4 H, br s), 2.36 (4 H, br s), 2.23 (3 H, s).

LCMS (10 cm_Formic_ACE 3 C18 AR_HPLC_CH3CN) Rt 8.98 min; m/z 434 [M+H] 96.6% purity.

Example 25

4-chloro-1-[2-(4-methylpiperazin-1-yl)ethyl]-5-phenyl-3-pyrrolidin-1-yl-pyrazolo[3,4-c]pyridazine (Compound Iz)

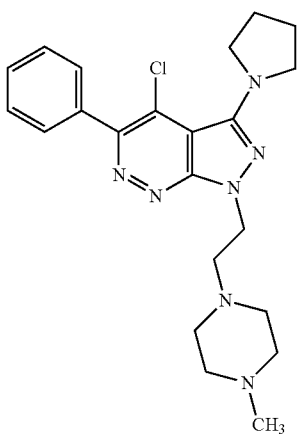 [SMILES: CN1CCN(CCn2nc(N3CCCC3)c3c(Cl)c(-c4ccccc4)nnc32)CC1]

Step 1: 3-iodo-1-[2-(4-methylpiperazin-1-yl)ethyl]-5-phenyl-pyrazolo[3,4-c]pyridazin-4-ol

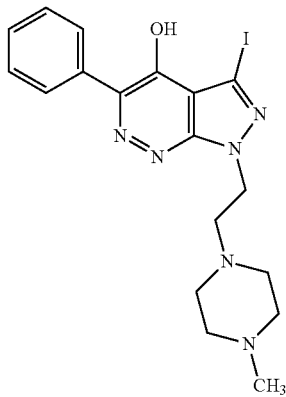 [SMILES: CN1CCN(CCn2nc(I)c3c(O)c(-c4ccccc4)nnc32)CC1]

A suspension of 4-chloro-3-iodo-1-(2-(4-methylpiperazin-1-yl)ethyl)-5-phenyl-1H-pyrazolo[3,4-c]pyridazine (140 mg, 0.29 mmol) in DMSO (3 mL) and NaOH aqueous solution (4 M, 3 mL) was heated to 50° C. for 2.5 h. The mixture was left to cool to rt, then neutralised to pH 2-3 before loading on an SCX (10 g) cartridge. The cartridge was eluted with MeOH then CH$_2$Cl$_2$/MeOH (1:1) and finally the product was released with 10% methanolic ammonia (7 N) in CH$_2$Cl$_2$/MeOH (1:1). Evaporation of the solvent gave the title compound (100 mg).

Step 2: 1-[2-(4-methylpiperazin-1-yl)ethyl]-5-phenyl-3-pyrrolidin-1-yl-pyrazolo[3,4-c]pyridazin-4-ol

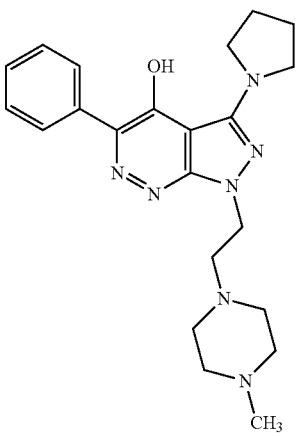 [SMILES: CN1CCN(CCn2nc(N3CCCC3)c3c(O)c(-c4ccccc4)nnc32)CC1]

To a solution of 3-iodo-1-[2-(4-methylpiperazin-1-yl)ethyl]-5-phenyl-pyrazolo[3,4-c]pyridazin-4-ol (120 mg, 0.26 mmol) in dioxane (1.7 mL) and DMSO (0.9 mL) was added pyrrolidine (233 µL, 2.8 mmol) and sodium t-butoxide (37 mg, 0.39 mmol) and nitrogen was bubbled in the resulting mixture for 30 min. Pd$_2$dba$_3$ (24 mg, 0.026 mmol) and Xantphos (9 mg, 0.016 mmol) were then added, the tube flushed with nitrogen, sealed and heated to 100° C. for 5 h. Pyrrolidine (40 µL, 0.49 mmol), Pd$_2$dba$_3$ (24 mg, 0.026 mmol) and Xantphos (9 mg, 0.016 mmol) were added and the mixture was heated to 100° C. for another 1 h. The mixture was left to cool to rt, then neutralised to pH 2-3 before loading on an SCX (10 g) cartridge. The cartridge was eluted with MeOH then CH$_2$Cl$_2$/MeOH (1:1) and finally the product was released with 10% methanolic ammonia (7 N) in CH$_2$Cl$_2$/MeOH (1:1). Evaporation of the solvent gave the title compound as a yellow glass (94 mg) which was reacted as such in the next step.

Step 3: 4-chloro-1-[2-(4-methylpiperazin-1-yl)ethyl]-5-phenyl-3-pyrrolidin-1-yl-pyrazolo[3,4-c]pyridazine (Compound Iz)

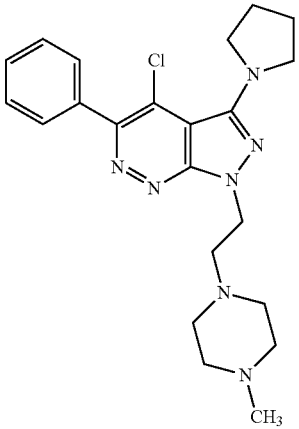 [SMILES: CN1CCN(CCn2nc(N3CCCC3)c3c(Cl)c(-c4ccccc4)nnc32)CC1]

A suspension of 1-[2-(4-methylpiperazin-1-yl)ethyl]-5-phenyl-3-pyrrolidin-1-yl-pyrazolo[3,4-c]pyridazin-4-ol (90 mg) in POCl$_3$ (6 mL) and CH$_2$Cl$_2$ (3 mL) was heated to 60° C. for 2.5 h. The mixture was concentrated in vacuo and the residue was partitioned between CH$_2$Cl$_2$ and sat. aq. NaHCO$_3$ solution. The layers were separated and the aqueous was extracted with CH$_2$Cl$_2$, the combined organics were dried (MgSO$_4$), filtered and concentrated in vacuo. The residue was purified by preparative HPLC to provide Compound Iz (12 mg).

$^1$H NMR δ (ppm) (CHCl$_3$-d): 7.75-7.71 (2 H, m), 7.53-7.43 (3 H, m), 4.69 (2 H, t, J=6.8 Hz), 3.62-3.55 (4 H, m), 2.94 (2 H, t, J=6.8 Hz), 2.63 (4 H, br s), 2.40 (4 H, br s), 2.26 (3 H, s), 2.02-1.97 (4 H, m).

LCMS (15 cm_Formic_ASCENTIS_HPLC_CH3CN) Rt 7.86 min; m/z 426 [M+H] 94.3% purity.

Example 26

2-[4-chloro-5-phenyl-3-(trifluoromethyl)pyrazolo[3,4-c]pyridazin-1-yl]-1-pyrrolidin-1-yl-ethanone (Compound Iaa)

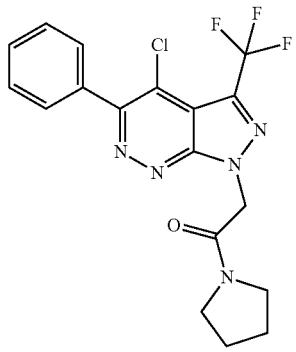 [SMILES: O=C(Cn1nc(C(F)(F)F)c2c(Cl)c(-c3ccccc3)nnc21)N1CCCC1]

Step 1: Synthesis of N-[3-(trifluoromethyl)-1H-pyrazol-5-yl]acetamide

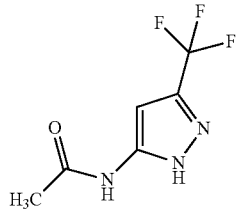

Acetyl chloride (7.7 ml, 108 mmol) was added over a period of 45 minutes to a solution of 3-(trifluoromethyl)-1H-pyrazol-5-amine (6.5 g, 43 mmol) and N-methylmorpholine (12.3 ml, 112 mmol) in CH$_2$Cl$_2$ (160 ml) with cooling in an ice bath. The reaction was allowed to warm to room temperature and stirred for 16 h, the solvent was removed in vacuo and the residue dissolved in methanol (150 ml). The solution was cooled in an ice bath and 25% aqueous NaOH (7.3 ml, 65 mmol) was added. After 3.25 h, 25% aqueous NaOH (0.5 ml, 4.4 mmol) was added and the reaction stirred for an additional 1.5 h. 2N HCl (20 ml) was added and the organic solvents were removed in vacuo at below 35° C. Water was added and the crude then extracted EtOAc (×2) and the extracts dried (MgSO$_4$) and concentrated in vacuo. The resultant residue was suspended in CH$_2$Cl$_2$ (20 ml) with stirring. The solid was filtered and washed with CH$_2$Cl$_2$ (2×3 ml) and dried in vacuo to provide the title compound as a white solid (7.3 g) which was used in the subsequent step.

Step 2: Synthesis of N-[4-iodo-3-(trifluoromethyl)-1H-pyrazol-5-yl]acetamide

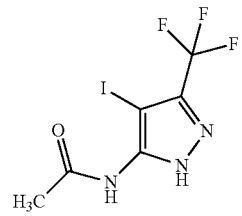

To a solution of N-[3-(trifluoromethyl)-1H-pyrazol-5-yl]acetamide (7.3 g, 38 mmol) in ethanol (120 mL) were added iodic acid (1.65 g, 9.4 mmol) and iodine (4.8 g, 18.9 mmol). The reaction was stirred for 3.25 h at 65° C. The reaction mixture was concentrated in vacuo and the residue was suspended in hot CH$_2$Cl$_2$ (150 ml) with stirring, the solid was filtered and resuspended in hot CH$_2$Cl$_2$ (100 ml) filtered and dried in vacuo to provide the title compound as a white solid (8.9 g) which was used in the subsequent step.

Step 3: Synthesis of N-[4-(2-phenylethynyl)-3-(trifluoromethyl)-1H-pyrazol-5-yl]acetamide

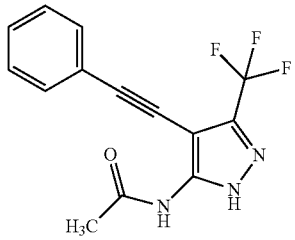 [SMILES: CC(=O)Nc1[nH]nc(C(F)(F)F)c1C#Cc1ccccc1]

A degassed solution of phenylacetylene (3.9 ml, 35 mmol) and Et$_3$N (36 mL) in DMF (13.5 mL) was added to N-[4-iodo-3-(trifluoromethyl)-1H-pyrazol-5-yl]acetamide (4.5 g, 14 mmol), CuI (530 mg, 2.8 mmol) and PdCl$_2$(PPh$_3$)$_2$ (980 mg, 1.4 mmol) under an atmosphere of N$_2$. The reaction was then heated to 85° C. for 3.5 h. The reaction mixture was concentrated in vacuo and the residue was purified by column chromatography (silica gel, ethyl acetate/isohexane 1:9 to 1:0) yielding the title compound as a brown oil (3 g) which was used in the subsequent step.

Step 4: Synthesis of 4-(2-phenylethynyl)-3-(trifluoromethyl)-1H-pyrazol-5-amine

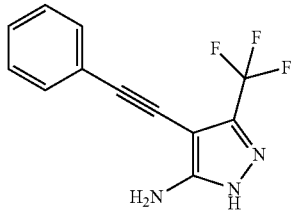 [SMILES: Nc1[nH]nc(C(F)(F)F)c1C#Cc1ccccc1]

A solution of N-[4-(2-phenylethynyl)-3-(trifluoromethyl)-1H-pyrazol-5-yl]acetamide (900 mg, 3.07 mmol) in ethanol (12 mL) and 25% NaOH (9 mL) was heated to 70° C. for 1.5 h. The organic layer was separated and the aqueous extracted with EtOAc (×2).

The combined organics were washed with water and the wash extracted with EtOAc. The combined organics were dried over MgSO₄, filtered and evaporated, yielding the title compound as a red oil (652 mg) which was used in the subsequent step.

Step 5: Synthesis of 4-chloro-5-phenyl-3-(trifluoromethyl)-1H-pyrazolo[3,4-c]pyridazine

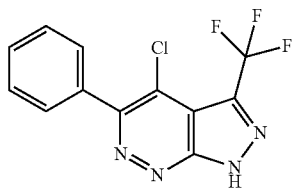 [SMILES: FC(F)(F)c1n[nH]c2nnc(-c3ccccc3)c(Cl)c12]

To a cooled (cooling bath −15° C.) stirred suspension of sodium nitrite (540 mg, 7.8 mmol) in conc. HCl (20 mL) was added a solution of 4-(2-phenylethynyl)-3-(trifluoromethyl)-1H-pyrazol-5-amine (652 mg, 2.6 mmol) in CH₂Cl₂ (3 mL). The cooling bath was removed and the reaction mixture was stirred at room temperature for 1 h. NaCl (900 mg) was added and the reaction heated at 50° C. for 16 h. CH₂Cl₂ was added to the cooled reaction mixture. The aqueous phase was extracted with CH₂Cl₂ twice and the organic phases combined, dried over MgSO₄, filtered and evaporated. The residue was purified by column chromatography (silica gel, ethyl acetate/isohexane 1:9 to 1:0) yielding the title compound as a yellow glass (115 mg) which was used in the subsequent step.

Step 6: Synthesis of 2-[4-chloro-5-phenyl-3-(trifluoromethyl)pyrazolo[3,4-c]pyridazin-1-yl]-1-pyrrolidin-1-yl-ethanone (Compound Iaa)

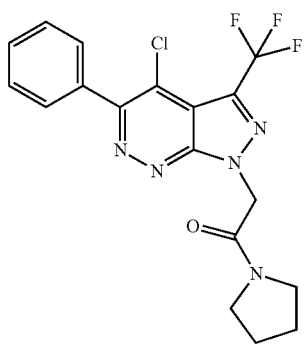 [SMILES: O=C(Cn1nc(C(F)(F)F)c2c(Cl)c(-c3ccccc3)nnc21)N1CCCC1]

Sodium hydride (18 mg, 0.45 mmol) was added to a solution of 4-chloro-5-phenyl-3-(trifluoromethyl)-1H-pyrazolo[3,4-c]pyridazine (115 mg, 0.38 mmol) and 2-chloro-1-pyrrolidin-1-yl-ethanone (81 mg, 0.55 mmol) in dry DMF (1.5 ml) and the reaction stirred for 21 h. Water and CH₂Cl₂ where added and the aqueous phase was extracted with CH₂Cl₂. The organic phases where combined, dried over MgSO₄, filtered and evaporated. The residue was purified by column chromatography (silica gel, ethyl acetate/isohexane 2:8 to 1:0) followed by preparative HPLC yielding Compound Iaa as a white solid (23 mg).

LCMS (15 cm_Bicarb_GeminiNX_HPLC_CH3CN) Rt 10.64 min; m/z 410 [M+H] 97.54% purity.

Example 27

3-bromo-4-chloro-5-phenyl-1H-pyrazolo[3,4-c]pyridazine (Compound Ibb)

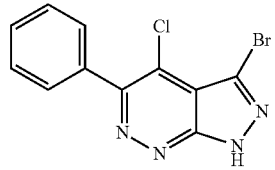 [SMILES: Clc1c(-c2ccccc2)nnc2[nH]nc(Br)c12]

A mixture of 4-chloro-5-phenyl-1H-pyrazolo[3,4-c]pyridazine (155 mg, 0.67 mmol), bromine (51 μL, 1 mmol) and triethylamine (98 μL, 0.7 mmol) in chloroform (4 mL) was stirred at room temperature for 1 h. Additional bromine (25 μL) and chloroform (4 mL) were added and the reaction mixture was stirred at room temperature for 4 h. Further bromine (25 μL) and triethylamine (98 μL) were added and the reaction mixture was stirred at room temperature for 16 h. The reaction mixture was diluted with CH₂Cl₂ and a sodium bicarbonate solution. The aqueous phase was extracted with CH₂Cl₂ and the combined organic phases were dried (phase separator cartridge) and concentrated in vacuo. The resultant residue was purified using chromatography (silica gel, ethyl acetate/isohexane 0:1 to 1:1), to provide Compound Ibb as a solid (97 mg).

¹H NMR δ (ppm) (CHCl₃-d): 11.75 (1 H, s), 7.79-7.70 (2 H, m), 7.59-7.51 (3 H, m).

LCMS (10 cm_Formic_ACE 3 C18 AR_HPLC_CH3CN) Rt 11.27 min; m/z 309 [M+H] 98.07% purity.

Example 28

4-chloro-1-[2-(4-methylpiperazin-1-yl)ethyl]-3-(5-methyl-2-thienyl)-5-phenyl-pyrazolo[3,4-c]pyridazine (Compound Icc)

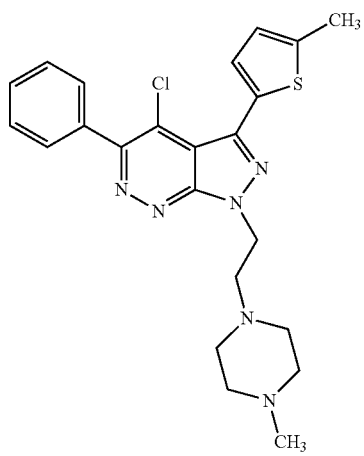 [SMILES: Cc1ccc(-c2nn(CCN3CCN(C)CC3)c3nnc(-c4ccccc4)c(Cl)c23)s1]

Compound Icc was synthesized following similar procedures outlined in Example 1, but using (5-methylthiophen-2-yl)boronic acid instead of 1-methyl-4-(4,4,5,5-tetramethyl-1,3,2-dioxaborolan-2-yl)-1H-pyrazole in Step 8.

¹H NMR δ (ppm) (CHCl₃-d): 7.67 (2 H, m), 7.43 (3 H, m), 7.36 (1 H, m), 6.72 (1 H, s), 4.79 (2 H, t), 2.96 (2 H, t), 2.61 (4 H, br s), 2.50-2.38 (7 H, m), 2.23 (3 H, s).

LCMS (10 cm_ESCI_Formic_MeCN) Rt 2.92 min; m/z 453 [M+H] 90.98% purity.

Example 29

4-chloro-3-cyclopropyl-5-phenyl-1H-pyrazolo[3,4-c]pyridazine (Compound Idd)

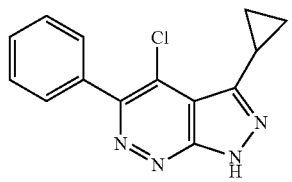 [SMILES: Clc1c(-c2ccccc2)nnc2[nH]nc(C3CC3)c12]

Compound Idd was synthesized according to Example 19, except using 3-cyclopropyl-1H-pyrazol-5-amine instead of 3-methyl-1H-pyrazol-5-amine.

¹H NMR δ (ppm) (CHCl₃-d): 10.71 (1 H, s), 7.80-7.76 (2 H, m), 7.57-7.49 (3 H, m), 2.64-2.56 (1 H, m), 1.17-1.11 (4 H, m).

LCMS (10 cm_ESCI_Bicarb_MeCN) Rt 3.76 min; m/z 271 [M+H] 98.22% purity.

Example 30

2-(4-chloro-3-cyclopropyl-5-phenyl-pyrazolo[3,4-c]pyridazin-1-yl)-1-pyrrolidin-1-yl-ethanone (Compound Iee)

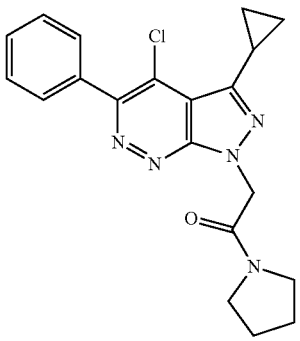 [SMILES: O=C(Cn1nc(C2CC2)c2c(Cl)c(-c3ccccc3)nnc21)N1CCCC1]

Sodium hydride (60% in mineral oil, 18 mg, 0.44 mmol) was added to a solution of 4-chloro-3-cyclopropyl-5-phenyl-1H-pyrazolo[3,4-c]pyridazine (100 mg, 0.37 mmol) and 2-chloro-1-(pyrrolidin-1-yl)ethanone (82 mg, 0.55 mmol) in dry DMF (3 mL) at room temperature for 16 h. The reaction mixture was diluted with ethyl acetate and water. The organic layer was washed with water, dried (MgSO₄), filtered and concentrated in vacuo. The residue was purified by column chromatography (silica gel, CH₂Cl₂/diethyl ether 8:2) to provide Compound Iee as a solid (65 mg).

¹H NMR δ (ppm) (CHCl₃-d): 7.76 (2 H, m), 7.56-7.45 (3 H, m), 5.39 (2 H, s), 3.65-3.57 (2 H, m), 3.54-3.45 (2 H, m), 2.61-2.53 (1 H, m), 2.11-2.01 (2 H, m), 1.94-1.84 (2 H, m), 1.20-1.04 (4 H, m).

LCMS (15 cm_Bicarb_GeminiNX_HPLC_CH3CN) Rt 10.44 min; m/z 382 [M+H] 97.47% purity.

Example 31

2-(4-chloro-3-cyclopropyl-5-phenyl-pyrazolo[3,4-c]pyridazin-1-yl)ethanol (Compound Iff)

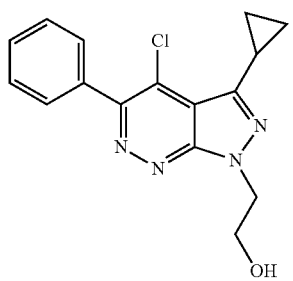 [SMILES: OCCn1nc(C2CC2)c2c(Cl)c(-c3ccccc3)nnc21]

Compound Iff was synthesized according to Example 55, Step 4, as described below, but using ethyl 2-(5-amino-3-cyclopropyl-pyrazol-1-yl)acetate instead of ethyl 2-(5-amino-3-phenyl-pyrazol-1-yl)acetate in Step 1.

¹H NMR δ (ppm) (CHCl₃-d): 7.79-7.75 (2 H, m), 7.57-7.49 (3 H, m), 4.79 (2 H, t), 4.21-4.15 (2 H, m), 3.18 (1 H, t), 2.61-2.56 (1 H, m), 1.14-1.09 (4 H, m).

LCMS (10 cm_Formic_ACE 3 C18 AR_HPLC_CH3CN) Rt 11.06 min; m/z 315 [M+H] 90.2% purity.

Example 32

2-[4-chloro-5-phenyl-3-(3-pyridyl)pyrazolo[3,4-c]pyridazin-1-yl]-N-(2-dimethylaminoethyl)acetamide (Compound Igg)

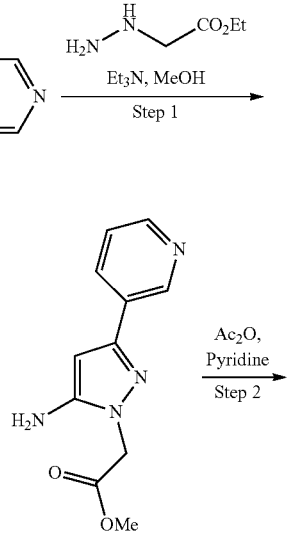

111
-continued

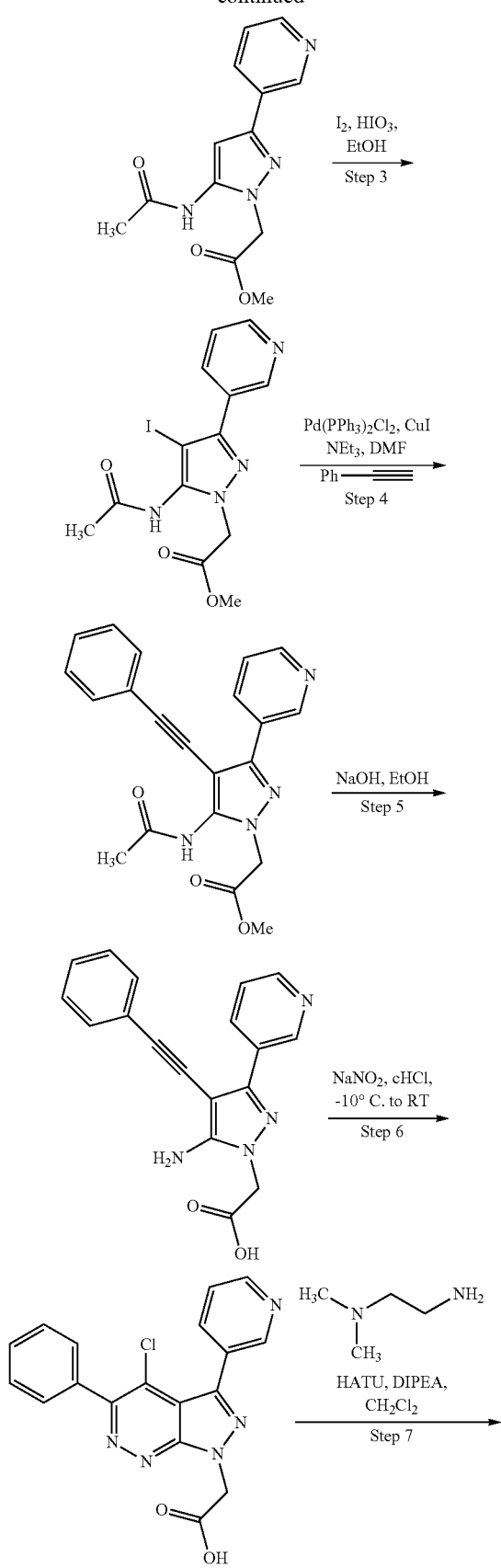

112
-continued

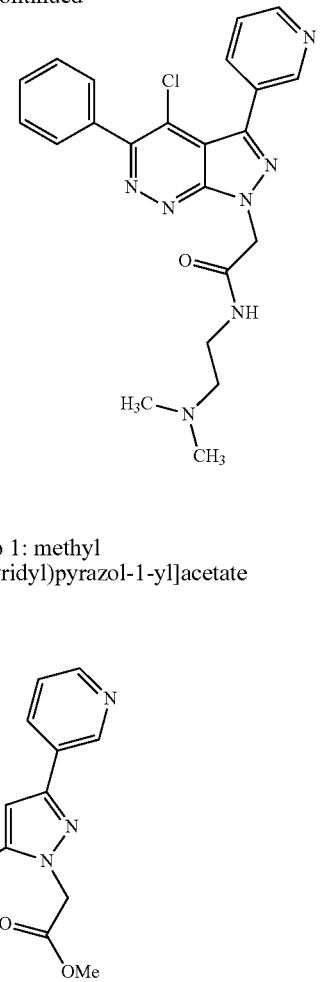

Step 1: methyl 2-[5-amino-3-(3-pyridyl)pyrazol-1-yl]acetate

A mixture of 3-oxo-3-pyridin-3-ylpropane nitrile (1.31 g, 9 mmol), ethyl hydrazinoacetate hydrochloride (1.39 g, 9 mmol) in methanol (9 mL) was heated under microwave irradiation at 120° C. for 1 h. The reaction mixture was concentrated in vacuo and the residue was purified by column chromatography (silica gel, ethyl acetate) yielding the title compound as a solid (510 mg).

Step 2: methyl 2-[5-acetamido-3-(3-pyridyl)pyrazol-1-yl]acetate

Acetic anhydride (431 µL, 4.4 mmol) was added dropwise to a solution of methyl 2-[5-amino-3-(3-pyridyl)pyrazol-1- yl]acetate (510 mg, 2.2 mmol) in pyridine (1.7 mL) at 0° C. under an atmosphere of nitrogen. Upon complete addition, the reaction mixture was warmed to room temperature and stirred for 16 h. The reaction mixture was filtered and the solid was washed with diethyl ether to provide the title compound as a white solid (430 mg).

Step 3 and 4: Methyl 2-[5-acetamido-4-(2-phenylethynyl)-3-(3-pyridyl)pyrazol-1-yl]acetate Methyl 2-[5-acetamido-4-(2-phenylethynyl)-3-(3-pyridyl)pyrazol-1-yl]acetate was synthesized according to Example 55, Steps 2 & 3, as described below, but using methyl 2-[5-acetamido-3-(3-pyridyl)pyrazol-1-yl]acetate.

Step 5: 2-[5-amino-4-(2-phenylethynyl)-3-(3-pyridyl)pyrazol-1-yl]acetic acid

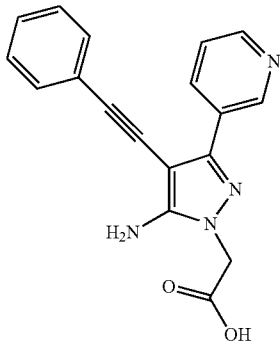 [SMILES: Nc1c(C#Cc2ccccc2)c(-c2cccnc2)nn1CC(=O)O]

To a suspension of ethyl 2-[5-acetamido-4-(2-phenylethynyl)-3-(3-pyridyl)pyrazol-1-yl]acetate (410 mg, 1.1 mmol) in ethanol (10 mL) was added 25% NaOH aqueous solution (6.5 mL). The reaction mixture was stirred at 85° C. for 6 h. The reaction mixture was cooled down to room temperature and ethanol was evaporated in vacuo. The resulting aqueous suspension was filtered and the solid was washed with acetonitrile and dried, yielding 235 mg of 2-[5-amino-4-(2-phenylethynyl)-3-(3-pyridyl)pyrazol-1-yl]acetic acid.

Step 6: 2-[4-chloro-5-phenyl-3-(3-pyridyl)pyrazolo[3,4-c]pyridazin-1-yl]acetic acid

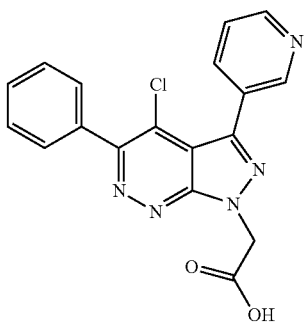 [SMILES: O=C(O)Cn1nc(-c2cccnc2)c2c(Cl)c(-c3ccccc3)nnc21]

Sodium nitrite (185 mg, 2.67 mmol) was added portion-wise to cHCl (5 mL) at 0° C. and stirred for 20 min. 2-[5-amino-4-(2-phenylethynyl)-3-(3-pyridyl)pyrazol-1-yl]acetic acid (285 mg, 0.89 mmol) was added as a solid. The reaction mixture was allowed to warm up, and stirred at room temperature for 16 h. The reaction mixture was filtered and the pH of the aqueous mother liquor was adjusted to 2 with sodium bicarbonate and 1N HCl. The aqueous mother liquor was extracted with $CH_2Cl_2$ three times and the combined organic phases were dried over $MgSO_4$, filtered and evaporated. The residue was triturated from diethyl ether, yielding 88 mg of a solid, consisting of 2-[4-chloro-5-phenyl-3-(3-pyridyl)pyrazolo[3,4-c]pyridazin-1-yl]acetic at an estimated 35% purity by LC/MS, which was used as such in the next step.

Step 7: 2-[4-chloro-5-phenyl-3-(3-pyridyl)pyrazolo[3,4-c]pyridazin-1-yl]-N-(2-dimethylaminoethyl)acetamide (Compound Igg)

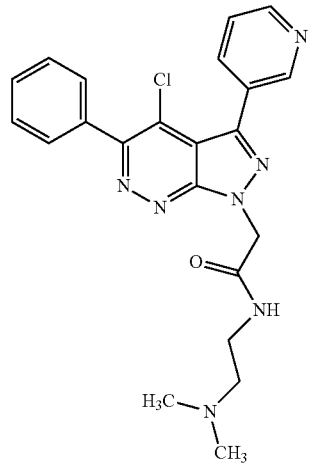 [SMILES: CN(C)CCNC(=O)Cn1nc(-c2cccnc2)c2c(Cl)c(-c3ccccc3)nnc21]

A mixture of 2-[4-chloro-5-phenyl-3-(3-pyridyl)pyrazolo[3,4-c]pyridazin-1-yl]acetic (88 mg, 35% pure, 0.084 mmol), DIPEA (67 µL, 0.38 mmol), HATU (112 mg, 0.30 mmol) and 2-(dimethylamino)ethylamine (32 µL, 0.30 mmol) in $CH_2Cl_2$ was stirred at room temperature for 1 h. The reaction mixture was diluted with water. The phases were separated and the aqueous phase was extracted with $CH_2Cl_2$. The combined organic layer were dried (phase separator cartridge) and concentrated in vacuo. The residue was purified by preparative HPLC to provide Compound Igg. (8 mg).

$^1$H NMR δ (ppm) ($CHCl_3$-d): 9.05 (1 H, d), 8.72 (1 H, dd), 8.48 (1 H, s), 8.13 (1 H, dt), 7.75-7.71 (2 H, m), 7.56-7.47 (3 H, m), 7.44 (1 H, dd), 5.53 (2 H, s), 3.67-3.59 (2 H, m), 2.98 (2 H, t), 2.64 (6 H, s).

LCMS (10 cm_ESCI_Bicarb_MeCN) Rt 2.79 min; m/z 436 [M+H] 95.24% purity.

Example 33

2-(4-chloro-3-methyl-5-phenyl-pyrazolo[3,4-c]pyridazin-1-yl)ethanol (Compound Ihh)

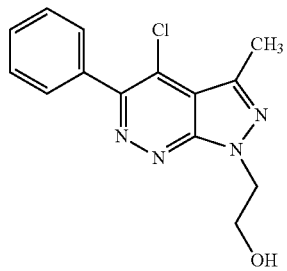 [SMILES: Cc1nn(CCO)c2nnc(-c3ccccc3)c(Cl)c12]

Compound Ihh was according to Example 55, Step 4, as described below, but using ethyl 2-(5-amino-3-methyl-pyrazol-1-yl)acetate instead of ethyl 2-(5-amino-3-phenyl-pyrazol-1-yl)acetate in Step 1.

$^1$H NMR δ (ppm) (CHCl$_3$-d): 7.78-7.75 (2 H, m), 7.56-7.49 (3 H, m), 4.85-4.80 (2 H, m), 4.24-4.18 (2 H, m), 3.13-3.08 (1 H, m), 2.81 (3 H, s).

LCMS (10 cm_ESCI_Bicarb_MeCN) Rt 3.35 min; m/z 289 [M+H] 95.23% purity.

Example 34

2-[4-chloro-5-phenyl-3-(3-pyridyl)pyrazolo[3,4-c]pyridazin-1-yl]ethanol (Compound Iii)

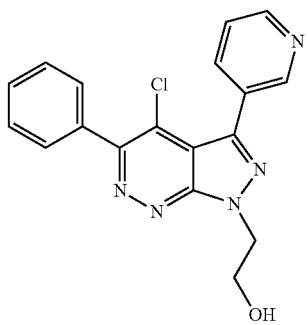 [SMILES: OCCn1nc(-c2cccnc2)c2c(Cl)c(-c3ccccc3)nnc21]

Compound Iii was synthesized according to Example 69, as shown below, but using 2-hydroxyethyl hydrazine instead of methyl hydrazine in Step 3.

$^1$H NMR δ (ppm) (CHCl$_3$-d): 9.04 (1 H, s), 8.73 (1 H, m), 8.11 (1 H, m), 7.76 (2 H, m), 7.54 (3 H, m), 7.45 (1 H, m), 5.01 (2 H, m), 4.31 (2 H, m), 2.92 (1 H, s).

LCMS (10 cm_ESCI_Formic_MeCN) Rt 3.1 min; m/z 352 [M+H] 98.44% purity.

Scheme III: General Scheme for Synthesising Compounds of Formula II

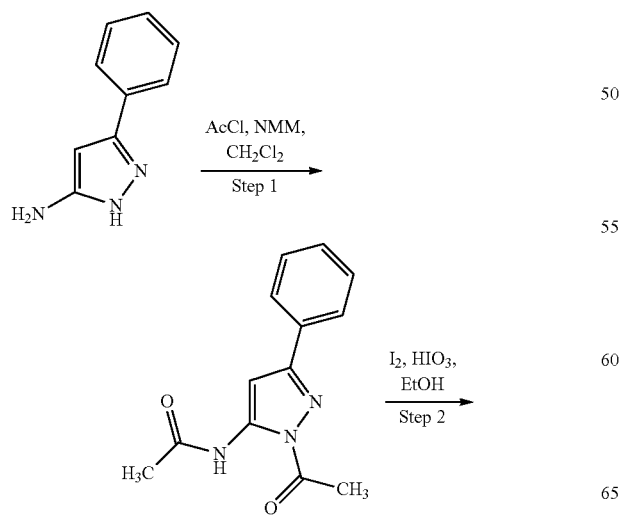

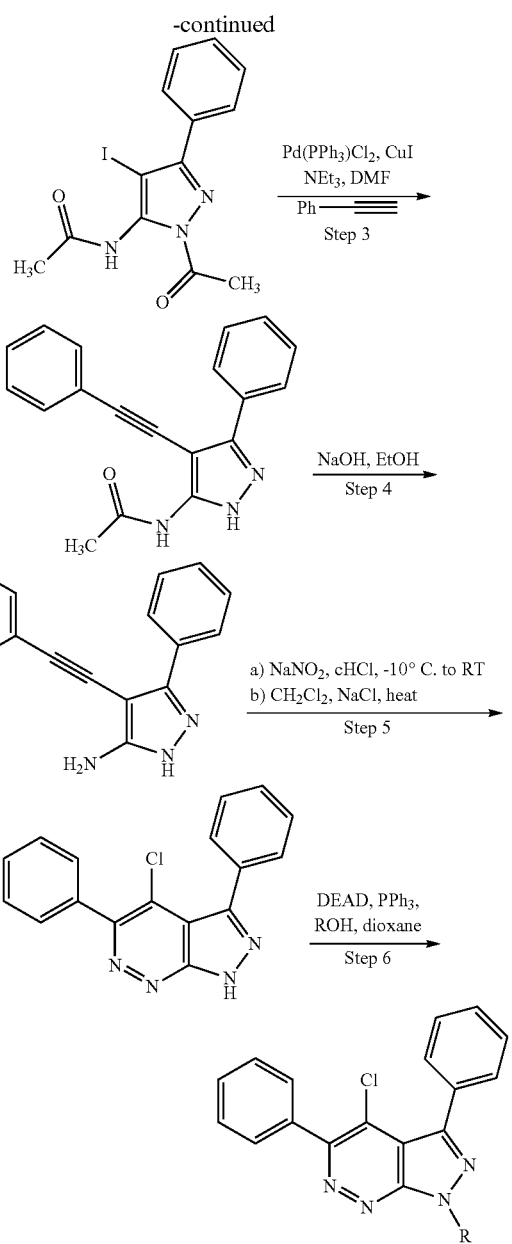

Example 35

4-chloro-1-[(3-methylimidazol-4-yl)methyl]-3,5-diphenyl-pyrazolo[3,4-c]pyridazine (Compound IIa)

Step 1: N-(2-acetyl-5-phenyl-pyrazol-3-yl)acetamide

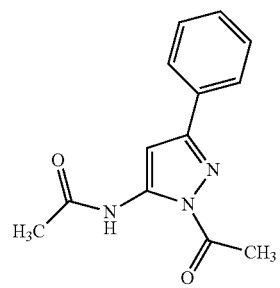 [SMILES: CC(=O)Nc1cc(-c2ccccc2)nn1C(C)=O]

To a solution of 5-phenyl-1H-pyrazol-3-amine (18.6 g, 0.117 mol) and N-methylmorpholine (30.8 mL, 0.281 mol) in CH$_2$Cl$_2$ (250 mL) was added acetyl chloride (20 mL, 0.281 mol) dropwise at 0° C. under an atmosphere of nitrogen. The reaction mixture was stirred at room temperature for 3 h. The reaction mixture was diluted with CH$_2$Cl$_2$ and water. The layers were separated and the organic layer was washed with water and brine, dried (phase separator cartridge) and concentrated in vacuo. Diethyl ether was added to the residue and the solid was collected by filtration, yielding the title compound as a solid (25.1 g).

Step 2: N-(2-acetyl-4-iodo-5-phenyl-pyrazol-3-yl) acetamide

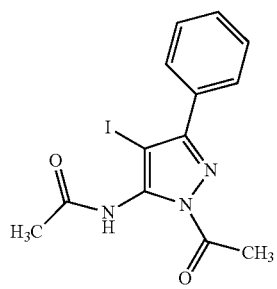 [SMILES: CC(=O)Nc1c(I)c(-c2ccccc2)nn1C(C)=O]

A suspension of N-(2-acetyl-5-phenyl-pyrazol-3-yl)acetamide (25.1 g, 0.103 mol), iodic acid (4.5 g, 0.026 mol) and iodine (15.7 g, 0.062 mol) in ethanol (250 mL) was heated at 50° C. for 3 h and cooled to room temperature. The reaction mixture was concentrated in vacuo and partitioned between CH$_2$Cl$_2$ and 2 M Na$_2$S$_2$O$_3$ aq. solution. The layers were separated and the organic washed with brine, dried (phase separator cartridge), and concentrated in vacuo to provide a mixture of the title compound and starting material (2.2:1, 30.3 g). The mixture was put in reaction again using iodic acid (1.6 g, 9.6 mmol) and iodine (9.7 g, 0.038 mol) in ethanol (250 mL) under the same conditions, to provide the title compound as a solid (31.9 g).

Step 3: N-[3-phenyl-4-(2-phenylethynyl)-H-pyrazol-5-yl]acetamide

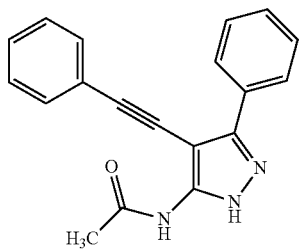 [SMILES: CC(=O)Nc1[nH]nc(-c2ccccc2)c1C#Cc1ccccc1]

Nitrogen was bubbled through a mixture of N-(2-acetyl-4-iodo-5-phenyl-pyrazol-3-yl)acetamide (31.87 g, 86.4 mmol), phenyl acetylene (17.6 g, 173 mmol), triethylamine (200 mL) and DMF (100 mL) for 15 min. Copper iodide (1.64 g, 8.6 mmol) and bis(triphenylphosphine)palladium(II) dichloride (3.0 g, 4.3 mmol) were added and the reaction mixture was stirred at 90° C. under nitrogen for 3 h. The reaction mixture was cooled to room temperature, diluted with ethyl acetate and water. The organic phase was washed with water and brine, dried (MgSO$_4$), filtered and concentrated in vacuo. The residue was purified by column chromatography (silica gel, iso-hexanes/ethyl acetate 5:1 to 1:1) yielding the title compound as a solid (12.5 g).

Step 4:
3-phenyl-4-(2-phenylethynyl)-1H-pyrazol-5-amine

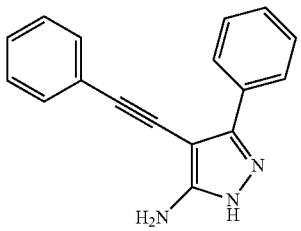 [SMILES: Nc1[nH]nc(-c2ccccc2)c1C#Cc1ccccc1]

A mixture of N-[3-phenyl-4-(2-phenylethynyl)-1H-pyrazol-5-yl]acetamide (12.5 g, 42 mmol), ethanol (100 mL) and 25% aq. NaOH solution (100 mL) was stirred and heated to 90° C. for 1 h and cooled to room temperature. The reaction mixture was diluted with ethyl acetate and water. The organic phase was washed with water and brine, dried (phase separator cartridge) and concentrated in vacuo. Diethyl ether was added to the residue and the solid was collected by filtration, washed with diethyl ether and dried in vacuo to provide the title compound as a solid (5.4 g).

Step 5:
4-chloro-3,5-diphenyl-1H-pyrazolo[3,4-c]pyridazine

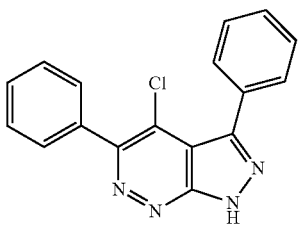 [SMILES: Clc1c(-c2ccccc2)nnc2[nH]nc(-c3ccccc3)c12]

Sodium nitrite (2.88 g, 42 mmol) was added portionwise to cHCl (314 mL) at −15° C. and stirred for 15 min. 3-phenyl-4-(2-phenylethynyl)-1H-pyrazol-5-amine (5.4 g, 21 mmol) was added as a solid, followed by the addition of CH$_2$Cl$_2$ (10 mL). The reaction mixture was allowed to warm up and stirred at room temperature for 1 h. The reaction mixture was diluted with CH$_2$Cl$_2$ (44 mL) and NaCl (2.7 g) was added. The reaction mixture was heated to 50° C. for 1 d. The layers were separated and the organic layer was washed with water, dried (phase separator cartridge) and concentrated in vacuo. The residue was purified by column chromatography (silica gel, iso-hexanes/ethyl acetate 4:1, then CH$_2$Cl$_2$/ethyl acetate 1:0 to 4:1) yielding the title compound as a solid (3.0 g).

Step 6: 4-chloro-1-[(3-methylimidazol-4-yl)methyl]-3,5-diphenyl-pyrazolo[3,4-c]pyridazine (Compound IIa)

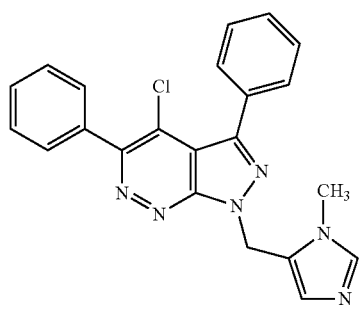 [SMILES: Cn1cncc1Cn1nc(-c2ccccc2)c2c(Cl)c(-c3ccccc3)nnc21]

A mixture of 4-chloro-3,5-diphenyl-1H-pyrazolo[3,4-c]pyridazine (100 mg, 0.33 mmol), 1-methyl-1H-imidazol-5-yl)methanol (73 mg, 0.65 mmol), diethyl azodicarboxylate (114 mg, 0.65 mmol) and triphenyl phosphine (171 mg, 0.65 mmol) in 1,4-dioxane (2 mL) was heated using microwave irradiation to 100° C. for 30 min. The reaction mixture was concentrated in vacuo and the residue was purified by preparative HPLC to provide Compound IIa (46 mg).

$^1$H NMR δ (ppm) (CHCl$_3$-d): 7.77-7.70 (4 H, m), 7.56-7.46 (7 H, m), 7.37 (1 H, s), 5.97 (2 H, s), 3.91 (3 H, s).

LCMS (10 cm_ESCI_Bicarb_MeCN) Rt 3.88 min; m/z 401 [M+H] 94.62% purity.

Example 36

General Procedure for Mitsunobu Reaction

A mixture of 4-chloro-3,5-diphenyl-1H-pyrazolo[3,4-c]pyridazine (0.33 mmol), the alcohol (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide the title compound.

Example 37

1-[2-(4-chloro-3,5-diphenyl-pyrazolo[3,4-c]pyridazin-1-yl)ethyl]pyrrolidin-2-one (Compound IIb)

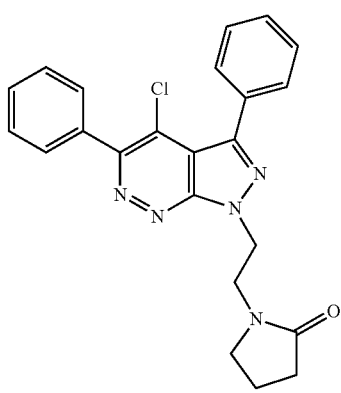 [SMILES: O=C1CCCN1CCn1nc(-c2ccccc2)c2c(Cl)c(-c3ccccc3)nnc21]

Compound IIb was synthesized from 4-chloro-3,5-diphenyl-1H-pyrazolo[3,4-c]pyridazine and 1-(2-hydroxyethyl) pyrrolidin-2-one following the general procedure for the Mitsunobu reaction as described above.

$^1$H NMR δ (ppm) (CHCl$_3$-d): 7.78-7.73 (4 H, m), 7.56-7.48 (6 H, m), 4.98 (2 H, t), 3.95 (2 H, t), 3.49 (2 H, t), 2.16 (2 H, t), 2.01-1.90 (2 H, m).

LCMS (10 cm_ESCI_Formic_MeCN) Rt 4.16 min; m/z 418 [M+H] 99.69% purity.

Example 38

4-chloro-1-(2-imidazol-1-ylethyl)-3,5-diphenyl-pyrazolo[3,4-c]pyridazine (Compound IIc)

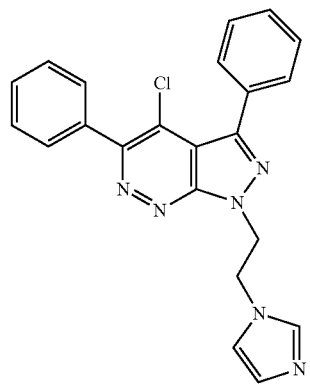 [SMILES: Clc1c(-c2ccccc2)nnc2c1c(-c1ccccc1)nn2CCn1ccnc1]

Compound IIc was synthesized from 4-chloro-3,5-diphenyl-1H-pyrazolo[3,4-c]pyridazine and 2-(1H-imidazol-1-yl)ethanol following the general procedure for the Mitsunobu reaction as described above.

$^1$H NMR δ (ppm) (CHCl$_3$-d): 7.76-7.71 (4 H, m), 7.55-7.48 (6 H, m), 7.31 (1 H, s), 6.98 (1 H, d), 6.96 (1 H, d), 5.16 (2 H, t), 4.72 (2 H, t).

LCMS (10 cm_ESCI_Bicarb_MeCN) Rt 3.38 min; m/z 401 [M+H] 98.08% pu

Example 39

4-chloro-3,5-diphenyl-1-(3,3,3-trifluoropropyl)pyrazolo[3,4-c]pyridazine (Compound IId)

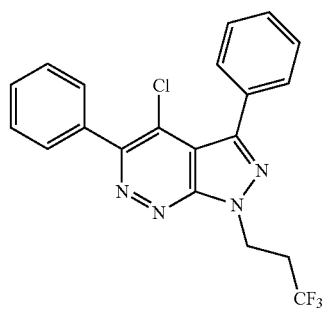 [SMILES: FC(F)(F)CCn1nc(-c2ccccc2)c2c(Cl)c(-c3ccccc3)nnc21]

Compound IId was synthesized from 4-chloro-3,5-diphenyl-1H-pyrazolo[3,4-c]pyridazine and 3,3,3-trifluoropropan-1-ol following the general procedure for the Mitsunobu reaction as described above.

$^1$H NMR δ (ppm) (CHCl$_3$-d): 7.79-7.74 (4 H, m), 7.56-7.47 (6 H, m), 5.09 (2 H, t), 3.07-2.94 (2 H, m).

LCMS (10 cm_Formic_ACE 3 C18 AR_HPLC_CH3CN) Rt 13.00 min; m/z 403 [M+H] 97.24% purity.

Example 40

4-chloro-3,5-diphenyl-1-tetrahydropyran-4-yl-pyrazolo[3,4-c]pyridazine (Compound IIe)

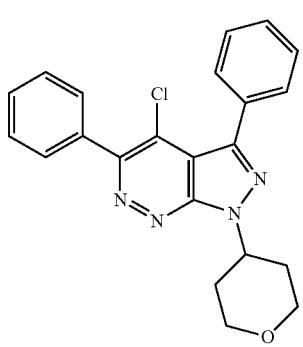 [SMILES: Clc1c(-c2ccccc2)nnc2c1c(-c1ccccc1)nn2C1CCOCC1]

Compound IIe was synthesized from 4-chloro-3,5-diphenyl-1H-pyrazolo[3,4-c]pyridazine and tetrahydro-2H-pyran-4-ol following the general procedure for the Mitsunobu reaction.

$^1$H NMR δ (ppm) (CHCl$_3$-d): 7.80-7.75 (4 H, m), 7.56-7.46 (6 H, m), 5.52-5.46 (1H, m), 4.23-4.19 (2 H, m), 3.71 (2 H, td), 2.60-2.54 (2 H, m), 2.18-2.14 (2 H, m).

LCMS (10 cm_Formic_ACE 3 C18 AR_HPLC_CH3CN) Rt 13.06 min; m/z 391 [M+H] 96.12% purity.

Example 41

4-chloro-1-[(3-methyloxetan-3-yl)methyl]-3,5-diphenyl-pyrazolo[3,4-c]pyridazine (Compound IIf)

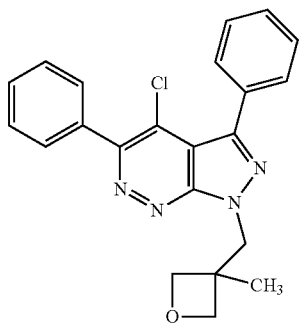 [SMILES: CC1(Cn2nc(-c3ccccc3)c3c(Cl)c(-c4ccccc4)nnc32)COC1]

Compound IIf was synthesized from 4-chloro-3,5-diphenyl-1H-pyrazolo[3,4-c]pyridazine and (3-methyloxetan-3-yl)methanol following the general procedure for the Mitsunobu reaction.

$^1$H NMR δ (ppm) (CHCl$_3$-d): 7.79-7.74 (4 H, m), 7.56-7.48 (6 H, m), 5.02 (2 H, s), 4.95 (2 H, d), 4.50 (2 H, d), 1.40 (3 H, s).

LCMS (15 cm_Bicarb_GeminiNX_HPLC_CH3CN) Rt 11.19 min; m/z 391 [M+H] 94.86% purity.

Example 42

4-chloro-1-[(1-methylpyrazol-4-yl)methyl]-3,5-diphenyl-pyrazolo[3,4-c]pyridazine (Compound IIg)

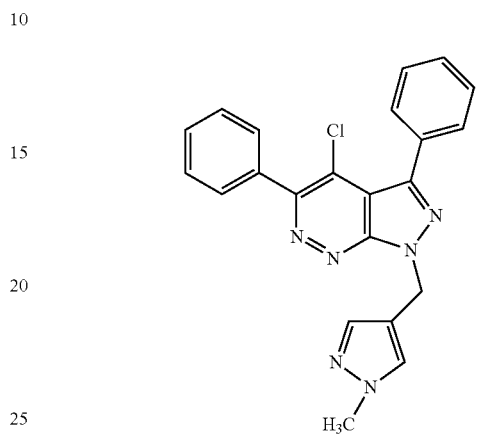

Compound IIg was synthesized from 4-chloro-3,5-diphenyl-1H-pyrazolo[3,4-c]pyridazine and (1-methyl-1H-pyrazol-4-yl)methanol following the general procedure for the Mitsunobu reaction as described above.

$^1$H NMR δ (ppm) (CHCl$_3$-d): 7.78-7.73 (4 H, m), 7.67 (1 H, s), 7.64 (1 H, s), 7.55-7.46 (6 H, m), 5.86 (2 H, s), 3.85 (3 H, s).

LCMS (10 cm_Formic_ACE 3 C18 AR_HPLC_CH3CN) Rt 12.26 min; m/z 401 [M+H] 95.22% purity.

Example 43

4-[(4-chloro-3,5-diphenyl-pyrazolo[3,4-c]pyridazin-1-yl)methyl]oxazole (Compound IIh)

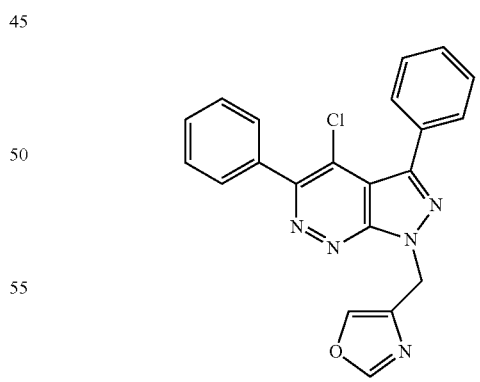

Compound IIh was synthesized from 4-chloro-3,5-diphenyl-1H-pyrazolo[3,4-c]pyridazine and oxazol-4-ylmethanol following the general procedure for the Mitsunobu reaction as described above.

$^1$H NMR δ (ppm) (CHCl$_3$-d): 7.85 (1 H, s), 7.83 (1 H, d, J=1.12 Hz), 7.79-7.75 (4H, m), 7.56-7.46 (6 H, m), 5.97 (2 H, s).

Example 44

4-chloro-1-(cyclopropylmethyl)-3,5-diphenyl-pyrazolo[3,4-c]pyridazine (Compound IIi)

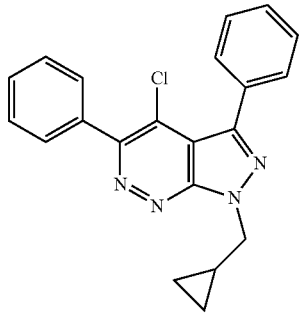 [SMILES: Clc1c(-c2ccccc2)nnc2c1c(-c1ccccc1)nn2CC1CC1]

Compound IIi was synthesized from 4-chloro-3,5-diphenyl-1H-pyrazolo[3,4-c]pyridazine and cyclopropylmethanol following the general procedure for the Mitsunobu reaction as described above.

¹H NMR δ (ppm) (CHCl₃-d): 7.81-7.76 (4 H, m), 7.55-7.45 (6 H, m), 4.69 (2 H, d), 1.62-1.58 (1 H, m), 0.65-0.61 (4 H, m).

LCMS (15 cm_Bicarb_GeminiNX_HPLC_CH3CN) Rt 11.77 min; m/z 361 [M+H] 96.25% purity.

Example 45

4-chloro-3,5-diphenyl-1-[[(2R)-tetrahydrofuran-2-yl]methyl]pyrazolo[3,4-c]pyridazine (Compound Ii)

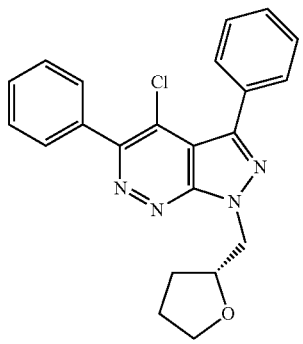 [SMILES: Clc1c(-c2ccccc2)nnc2c1c(-c1ccccc1)nn2C[C@H]1CCCO1]

Compound IIj was synthesized from 4-chloro-3,5-diphenyl-1H-pyrazolo[3,4-c]pyridazine and R)-(tetrahydrofuran-2-yl)methanol following the general procedure for the Mitsunobu reaction as described above.

¹H NMR δ (ppm) (CHCl₃-d): 7.80-7.76 (4 H, m), 7.55-7.44 (6 H, m), 4.97 (1 H, dd), 4.78-4.64 (2 H, m), 3.99 (1 H, q), 3.83-3.74 (1 H, m), 2.16-2.03 (1 H, m), 2.03-1.80 (3 H, m).

Example 46

4-chloro-3,5-diphenyl-1-(2,2,2-trifluoroethyl)pyrazolo[3,4-c]pyridazine (Compound IIk)

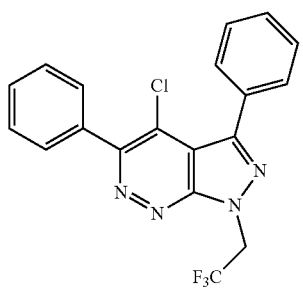 [SMILES: FC(F)(F)Cn1nc(-c2ccccc2)c2c(Cl)c(-c3ccccc3)nnc21]

Compound IIk was synthesized from 4-chloro-3,5-diphenyl-1H-pyrazolo[3,4-c]pyridazine and 2,2,2-trifluoroethanol following the general procedure for the Mitsunobu reaction as described above.

¹H NMR δ (ppm) (CHCl₃-d): 7.81-7.75 (4 H, m), 7.58-7.50 (6 H, m), 5.40 (2 H, q).

LCMS (10 cm_Formic_ACE 3 C18 AR_HPLC_CH3CN) Rt 12.89 min; m/z 389 [M+H] 97.09% purity.

Example 47

4-chloro-1-(2-fluoroethyl)-3,5-diphenyl-pyrazolo[3,4-c]pyridazine (Compound IIl)

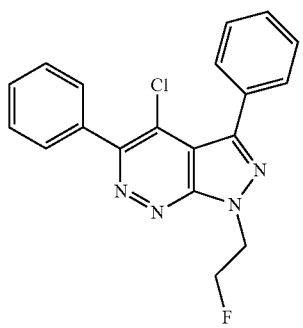 [SMILES: FCCn1nc(-c2ccccc2)c2c(Cl)c(-c3ccccc3)nnc21]

Compound IIl was synthesized from 4-chloro-3,5-diphenyl-1H-pyrazolo[3,4-c]pyridazine and 2-fluoroethanol following the general procedure for the Mitsunobu reaction as described above.

¹H NMR δ (ppm) (CHCl₃-d): 7.80-7.75 (4 H, m), 7.56-7.49 (6 H, m), 5.18-5.07 (3H, m), 5.01 (1 H, t).

LCMS (15 cm_Bicarb_GeminiNX_HPLC_CH3CN) Rt 11.05 min; m/z 353 [M+H] 96.03% purity.

Example 48

4-(4-chloro-3,5-diphenyl-pyrazolo[3,4-c]pyridazin-1-yl)butan-2-one (Compound IIm)

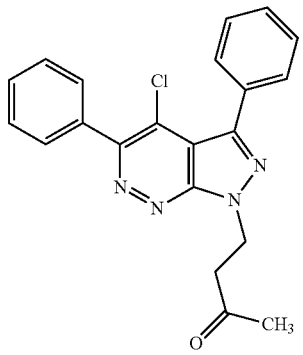 [SMILES: CC(=O)CCn1nc(-c2ccccc2)c2c(Cl)c(-c3ccccc3)nnc21]

Compound IIm was synthesized from 4-chloro-3,5-diphenyl-1H-pyrazolo[3,4-c]pyridazine and 4-hydroxybutan-2-one following the general procedure for the Mitsunobu reaction as described above.

$^1$H NMR δ (ppm) (CHCl$_3$-d): 7.78-7.73 (4 H, m), 7.56-7.45 (6 H, m), 5.09 (2 H, t), 3.34 (2 H, t), 2.26 (3 H, s).

LCMS (10 cm_Formic_ACE 3 C18 AR_HPLC_CH3CN) Rt 12.5 min; m/z 377 [M+H] 95.07% purity.

Example 49

4-chloro-3,5-diphenyl-1-(3-pyridylmethyl)pyrazolo[3,4-c]pyridazine (Compound IIn)

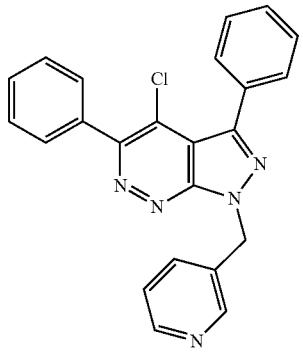 [SMILES: Clc1c(-c2ccccc2)nnc2c1c(-c1ccccc1)nn2Cc1cccnc1]

Compound IIn was synthesized from 4-chloro-3,5-diphenyl-1H-pyrazolo[3,4-c]pyridazine and pyridin-3-ylmethanol following the general procedure for the Mitsunobu reaction.

$^1$H NMR δ (ppm) (CHCl$_3$-d): 8.85 (1 H, d), 8.57 (1 H, dd), 7.93 (1 H, dt), 7.79-7.73 (4 H, m), 7.56-7.48 (6 H, m), 7.31-7.27 (1 H, m), 6.00 (2 H, s).

LCMS (10 cm_ESCI_Formic_MeCN) Rt 4.03 min; m/z 398 [M+H] 97.31% purity.

Example 50

4-chloro-3,5-diphenyl-1-(4-pyridylmethyl)pyrazolo[3,4-c]pyridazine (Compound IIo)

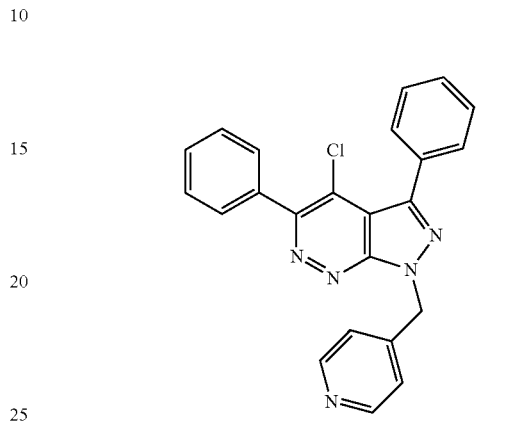

Compound IIo was synthesized from 4-chloro-3,5-diphenyl-1H-pyrazolo[3,4-c]pyridazine and pyridin-4-ylmethanol following the general procedure for the Mitsunobu reaction as described above.

$^1$H NMR δ (ppm) (CHCl$_3$-d): 8.60 (2 H, dd), 7.79-7.75 (4 H, m), 7.56-7.48 (6 H, m), 7.39 (2 H, d), 5.98 (2 H, s).

LCMS (10 cm_ESCI_Formic_MeCN) Rt 3.77 min; m/z 398 [M+H] 97.2% purity.

Example 51

4-chloro-3,5-diphenyl-1-(2-pyridylmethyl)pyrazolo[3,4-c]pyridazine (Compound IIp)

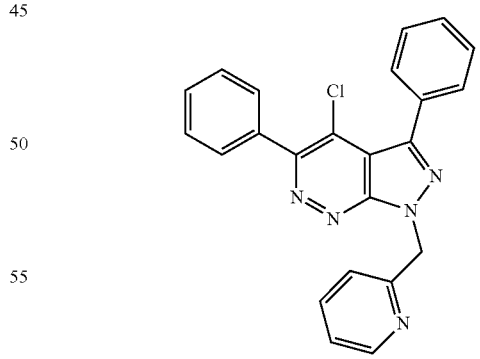

Compound IIp was synthesized from 4-chloro-3,5-diphenyl-1H-pyrazolo[3,4-c]pyridazine and pyridin-2-ylmethanol following the general procedure for the Mitsunobu reaction as described above.

$^1$H NMR δ (ppm) (CHCl$_3$-d): 8.60-8.57 (1 H, m), 7.80-7.75 (4 H, m), 7.68-7.62 (1H, m), 7.55-7.46 (7 H, m), 7.23-7.20 (1 H, m) 6.15 (2 H, s).

LCMS (15 cm_Bicarb_GeminiNX_HPLC_CH3CN) Rt 11.05 min; m/z 398 [M+H] 95.92% purity.

Example 52

4-chloro-1-(2-methylsulfonylethyl)-3,5-diphenyl-pyrazolo[3,4-c]pyridazine (Compound IIq)

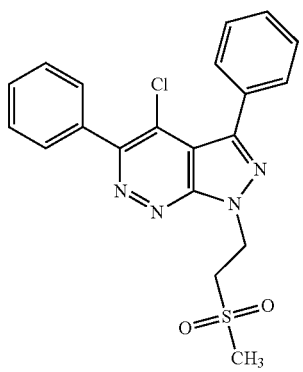 [SMILES: CS(=O)(=O)CCn1nc(-c2ccccc2)c2c(Cl)c(-c3ccccc3)nnc21]

Compound IIq was synthesized from 4-chloro-3,5-diphenyl-1H-pyrazolo[3,4-c]pyridazine and 2-(methylsulfonyl)ethanol following the general procedure for the Mitsunobu reaction as described above.

$^1$H NMR δ (ppm) (CHCl$_3$-d): 7.78-7.74 (4 H, m), 7.56-7.48 (6 H, m), 5.34-5.29 (2H, m), 3.88 (2 H, t), 3.05 (3 H, s).

LCMS (10 cm_ESCI_Formic_MeCN) Rt 4.13 min; m/z 413 [M+H] 97.31% purity.

Scheme IV: General Scheme for Synthesising Compounds of Formula II

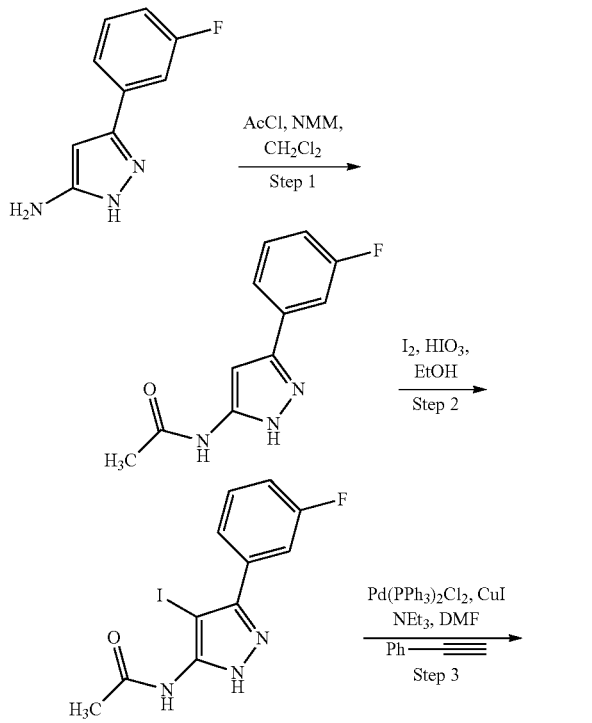

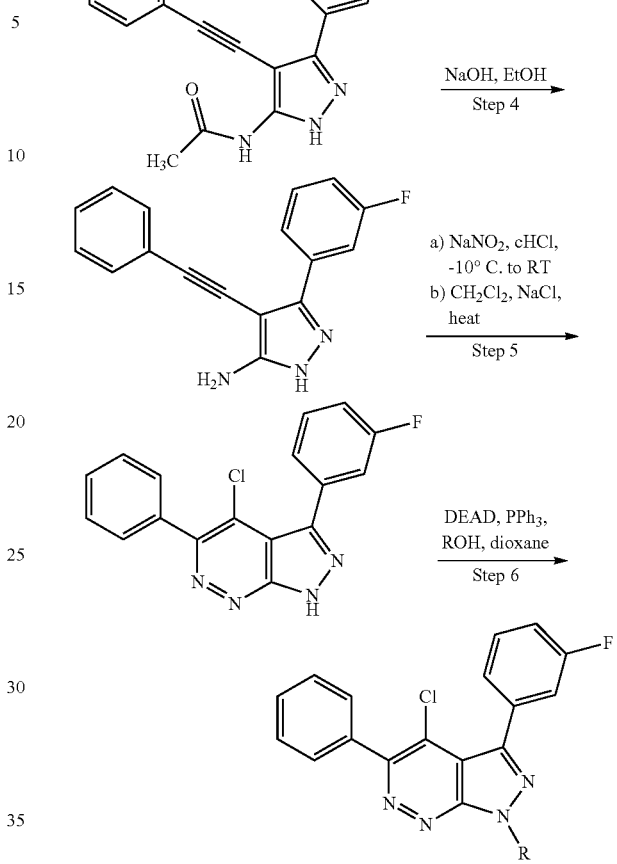

Example 53

1-[2-[4-chloro-3-(3-fluorophenyl)-5-phenyl-pyrazolo[3,4-c]pyridazin-1-yl]ethyl]pyrrolidin-2-one (Compound IIr)

Step 1:
N-[3-(3-fluorophenyl)-1H-pyrazol-5-yl]acetamide

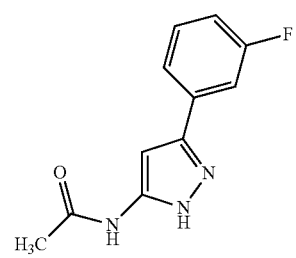 [SMILES: CC(=O)Nc1cc(-c2cccc(F)c2)n[nH]1]

To a solution of 3-(3-fluorophenyl)-1H-pyrazol-5-amine (6.5 g, 36 mmol) and N-methylmorpholine (9.7 mL, 88 mmol) in CH$_2$Cl$_2$ (150 mL) was added acetyl chloride (6 mL, 85 mmol) dropwise at 0° C. under an atmosphere of nitrogen. The reaction mixture was stirred at room temperature for 1 d. The reaction mixture was concentrated in vacuo. MeOH (50 mL) and THF (50 mL) were added to the residue, followed by the addition of NaOH solution (aq. 2.5 M, 42.5 mL) at 0° C. The reaction mixture was stirred at room temperature for 15 min and HCl solution was added until pH reached ~6. The organic solvents were evaporated in vacuo. The solid from the resulting aqueous suspension was collected by filtration, yielding the title compound as a solid (7.6 g).

Step 2: N-[3-(3-fluorophenyl)-4-iodo-1H-pyrazol-5-yl]acetamide

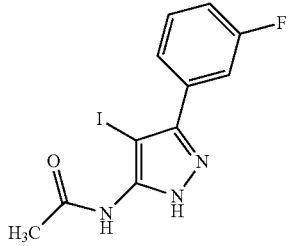 [SMILES: CC(=O)Nc1[nH]nc(-c2cccc(F)c2)c1I]

A suspension of N-[3-(3-fluorophenyl)-1H-pyrazol-5-yl] acetamide (7.6 g, 34.7 mmol), iodic acid (1.5 g, 8.5 mmol) and iodine (4.4 g, 17.3 mmol) in ethanol (200 mL) was heated at 60° C. for 1 h and cooled to room temperature. The reaction mixture was concentrated in vacuo and partitioned between CH$_2$Cl$_2$ and 2 M Na$_2$S$_2$O$_3$ aq. solution. The layers were separated and the organic washed with brine, dried (MgSO$_4$), and concentrated in vacuo to provide the title compound as a solid (10.8 g).

Step 3: N-[3-(3-fluorophenyl)-4-(2-phenylethynyl)-1H-pyrazol-5-yl]acetamide

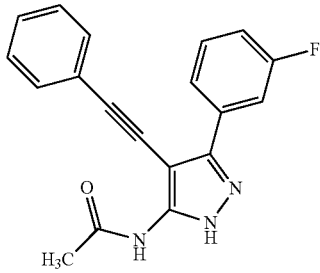 [SMILES: CC(=O)Nc1[nH]nc(-c2cccc(F)c2)c1C#Cc1ccccc1]

Nitrogen was bubbled through a mixture of N-[3-(3-fluorophenyl)-4-iodo-1H-pyrazol-5-yl]acetamide (10.8 g, 44 mmol), phenyl acetylene (12.5 g, 123 mmol), triethylamine (100 mL) and DMF (40 mL) for 15 min. Copper iodide (840 mg, 4.42 mmol) and bis(triphenylphosphine)palladium(II) dichloride (1.5 g, 2.1 mmol) were added and the reaction mixture was stirred at 90° C. under nitrogen for 6 h. The reaction mixture was cooled to room temperature, diluted with ethyl acetate and water. The organic phase was washed with water and brine, dried (MgSO$_4$), filtered and concentrated in vacuo. The residue was purified by column chromatography (silica gel, isohexane/ethyl acetate 1:0 to 0:1) yielding the title compound as a solid (4 g).

Step 4: 3-(3-fluorophenyl)-4-(2-phenylethynyl)-1H-pyrazol-5-amine

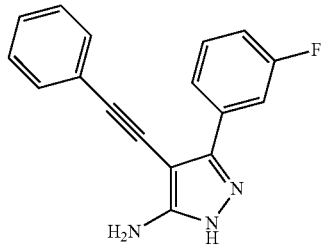 [SMILES: Nc1[nH]nc(-c2cccc(F)c2)c1C#Cc1ccccc1]

A mixture of N-[3-(3-fluorophenyl)-4-(2-phenylethynyl)-1H-pyrazol-5-yl]acetamide (2 g, 6.2 mmol), ethanol (22 mL) and 25% aq. NaOH solution (22 mL) was stirred and heated to 80° C. for 1 h and cooled to room temperature. The reaction mixture was diluted with ethyl acetate and water. The organic phase was washed with water and brine, dried (phase separator cartridge) and concentrated in vacuo, to provide the title compound as a solid (1.2 g).

Step 5: 4-chloro-3-(3-fluorophenyl)-5-phenyl-1H-pyrazolo[3,4-c]pyridazine

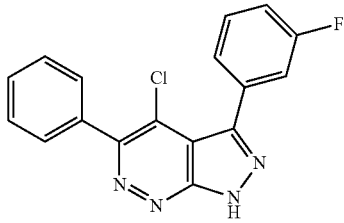 [SMILES: Fc1cccc(-c2n[nH]c3nnc(-c4ccccc4)c(Cl)c23)c1]

Sodium nitrite (740 mg, 10.7 mmol) was added portionwise to cHCl (24 mL) at −15° C. and stirred for 15 min. 3-(3-fluorophenyl)-4-(2-phenylethynyl)-1H-pyrazol-5-amine (1 g, 3.6 mmol) was added as a solid, followed by the addition of CH$_2$Cl$_2$ (10 mL). The reaction mixture was allowed to warm up and stirred at room temperature for 1.5 h. The reaction mixture was diluted with CH$_2$Cl$_2$ (20 mL) and NaCl (0.5 g) was added. The reaction mixture was heated to 50° C. for 1 d. The layers were separated and the organic layer was washed with water, dried (phase separator cartridge) and concentrated in vacuo. The residue was purified by column chromatography (silica gel, ethyl acetate/isohexane 0:1 to 7:3) yielding the title compound as a solid (500 mg).

Step 6: 1-[2-[4-chloro-3-3-fluorophenyl)-5-phen-pyrazolo[3,4-c]pyridazin-1-yl]ethyl]pyrrolidin-2-one (Compound IIr)

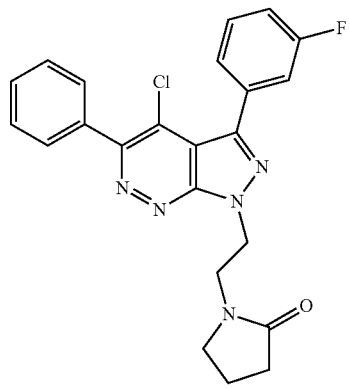 [SMILES: O=C1CCCN1CCn1nc(-c2cccc(F)c2)c2c(Cl)c(-c3ccccc3)nnc21]

Compound IIr was synthesized from 4-chloro-3-(3-fluorophenyl)-5-phenyl-1H-pyrazolo[3,4-c]pyridazine and 1-(2-hydroxyethyl)pyrrolidin-2-one following the general procedure for the Mitsunobu reaction as described.

$^1$H NMR δ (ppm) (CHCl$_3$-d): 7.77-7.74 (2 H, m), 7.59-7.51 (4 H, m), 7.51-7.43 (2H, m), 7.22-7.16 (1 H, m), 4.98 (2 H, t), 3.94 (2 H, t), 3.51 (2 H, t), 2.14 (2 H, t), 2.02-1.92 (2H, m).

LCMS (10 cm_ESCI_Bicarb_MeCN) Rt 3.92 min; m/z 436 [M+H] 99.49% purity.

Example 54

4-chloro-3-(3-fluorophenyl)-1-(2-imidazol-1-yl-ethyl)-5-phenyl-pyrazolo[3,4-c]pyridazine (Compound IIs)

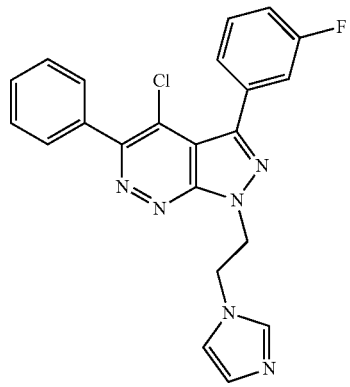 [SMILES: Fc1cccc(-c2nn(CCn3ccnc3)c3nnc(-c4ccccc4)c(Cl)c23)c1]

Compound IIs was synthesized from 4-chloro-3-(3-fluorophenyl)-5-phenyl-1H-pyrazolo[3,4-c]pyridazine and 2-(1H-imidazol-1-yl)ethanol following the general procedure for the Mitsunobu reaction as described above.

$^1$H NMR δ (ppm) (CHCl$_3$-d): 7.77-7.73 (2 H, m), 7.55-7.46 (6 H, m), 7.36 (1 H, s), 7.31-7.23 (1 H, m), 7.01-6.99 (1 H, m), 6.97 (1 H, s), 5.17 (2 H, t), 4.72 (2 H, t).

LCMS (10 cm_ESCI_Formic_MeCN) Rt 2.85 min; m/z 419 [M+H] 92.97% purity.

Example 55

4-chloro-1-[2-[(3S)-3-fluoropyrrolidin-1-yl]ethyl]-3,5-diphenyl-pyrazolo[3,4-c]pyridazine (Compound IIt)

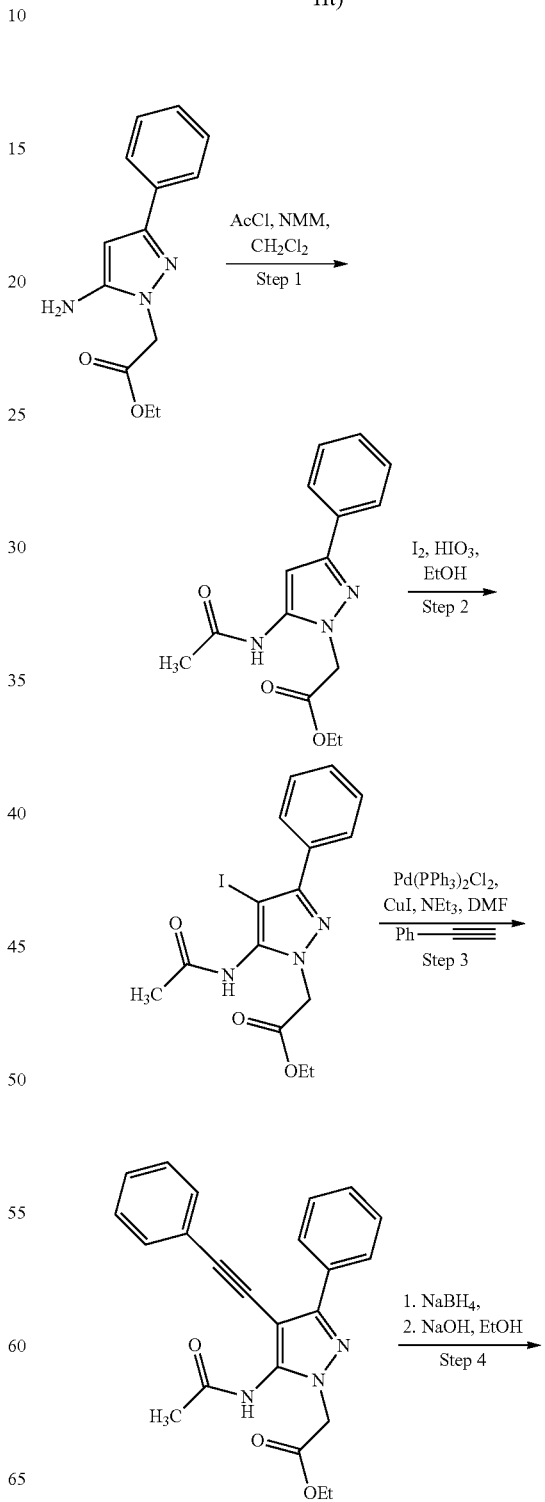

133
-continued

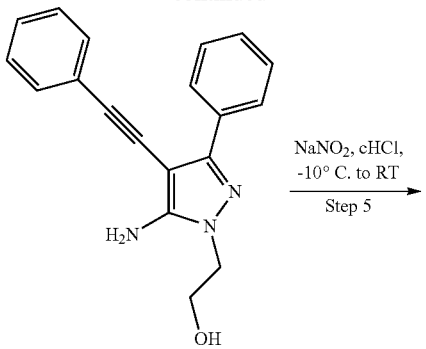

NaNO₂, cHCl,
-10° C. to RT
Step 5

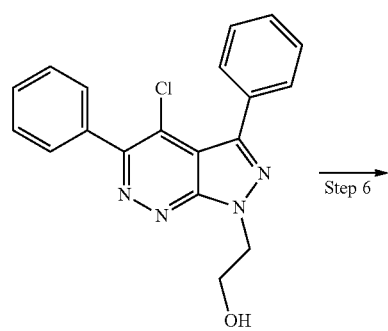

Step 6

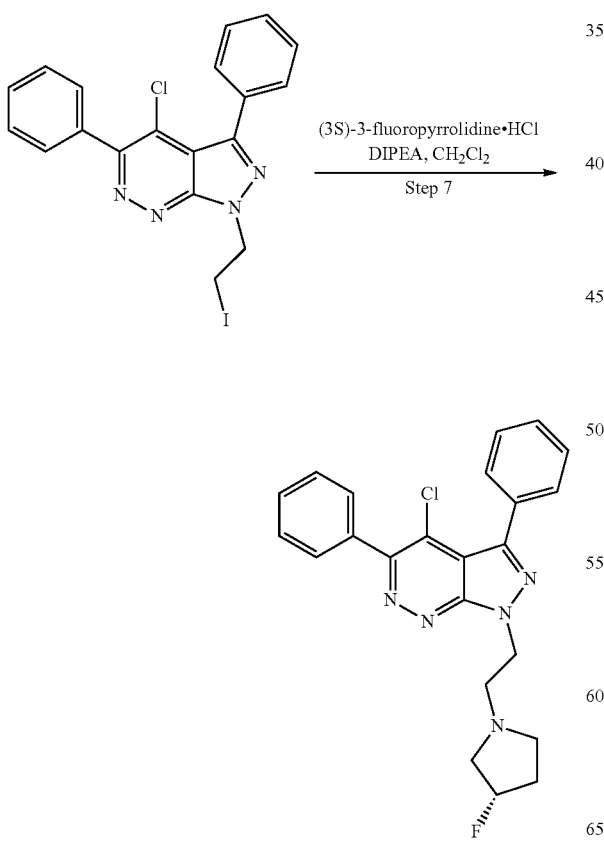

(3S)-3-fluoropyrrolidine•HCl
DIPEA, CH₂Cl₂
Step 7

134

Step 1: Ethyl 2-(5-acetamido-3-phenyl-pyrazol-1-yl)acetate

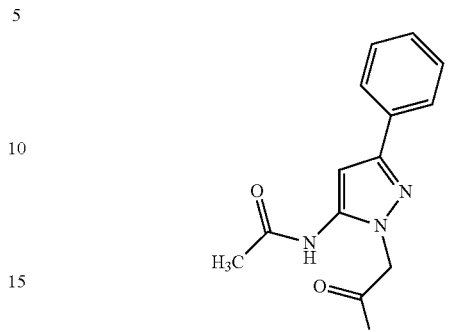

Acetic anhydride (12.7 mL, 134.8 mmol) was added dropwise to a solution of ethyl 2-(5-amino-3-phenyl-pyrazol-1-yl)acetate (31.5 g, 128.4 mmol) in pyridine (200 mL) at 0° C. under an atmosphere of nitrogen. Upon complete addition, the reaction mixture was warmed to room temperature and stirred for 16 h. The reaction mixture was concentrated in vacuo. The residue was diluted in CH₂Cl₂ (250 mL). The organic phase was washed with water and brine, dried (MgSO₄), filtered and concentrated in vacuo. The residue was triturated from diethyl ether, filtered and dried to provide the title compound as a white solid (34.81 g).

Step 2: Ethyl 2-(5-acetamido-4-iodo-3-phenyl-pyrazol-1-yl)acetate

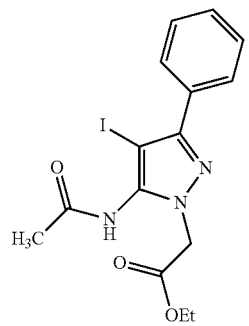 [SMILES: CCOC(=O)Cn1nc(-c2ccccc2)c(I)c1NC(C)=O]

A suspension of ethyl 2-(5-acetamido-3-phenyl-pyrazol-1-yl)acetate (34.81 g, 60.6 mmol), iodic acid (5.33 g, 30.3 mmol) and iodine (15.37 g, 60.6 mmol) in ethanol (250 mL) was heated at 50° C. for 1.5 h and cooled to room temperature. The reaction mixture was concentrated in vacuo and the residue was dissolved in CH₂Cl₂ (250 mL). The solution was washed twice with 2 M Na₂S₂O₃ followed by brine solution. The organic layer was dried (magnesium sulphate), filtered and concentrated in vacuo. The residue was triturated from diethyl ether, filtered and dried to provide the title compound as a solid (44.13 g).

Step 3: Ethyl 2-[5-acetamido-3-phenyl-4-(2-phenyl-ethynyl)pyrazol-1-yl]acetate

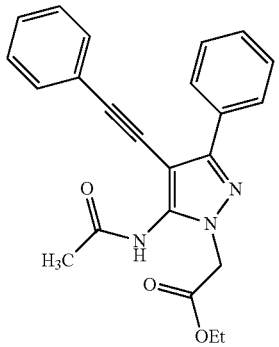 [SMILES: CCOC(=O)Cn1nc(-c2ccccc2)c(C#Cc2ccccc2)c1NC(C)=O]

Nitrogen was bubbled through a mixture of ethyl 2-(5-acetamido-4-iodo-3-phenyl-pyrazol-1-yl)acetate (34.95 g, 84.58 mmol), phenyl acetylene (18.6 mL, 169.16 mmol), triethylamine (300 mL) and DMF (120 mL) for 1.5 h. Copper iodide (1.61 g, 8.46 mmol) and bis(triphenylphosphine)palladium(II) dichloride (3 g, 4.23 mmol) were added and the reaction mixture was stirred at 90° C. under nitrogen for 2 h. The reaction mixture was concentrated in vacuo, and the residue was co-evaporated with toluene to remove excess DMF. The residue was diluted with ethyl acetate (300 mL) and washed with water (2×100 mL). The organic phase was filtered through celite, washed with water and brine, dried (MgSO$_4$), filtered and concentrated in vacuo. The residue was triturated from ethyl acetate, yielding the title compound as a solid (25.67 g).

Step 4: 2-[5-Amino-3-phenyl-4-(2-phenylethynyl)pyrazol-1-yl]ethanol

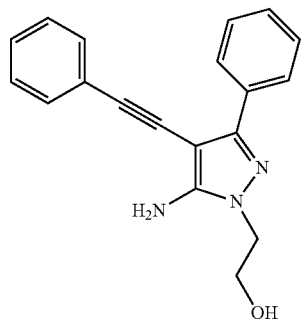 [SMILES: Nc1c(C#Cc2ccccc2)c(-c2ccccc2)nn1CCO]

To a suspension of ethyl 2-[5-acetamido-3-phenyl-4-(2-phenylethynyl)pyrazol-1-yl]acetate (22.4 g, 58 mmol) in ethanol (290 mL) was added sodium borohydride (11 g, 289 mmol) and the reaction stirred at room temperature for 16 h. The reaction mixture was partially concentrated to a final volume of 250 mL. 25% NaOH (250 mL) was added and the reaction mixture was stirred at 80° C. for 4 h. The reaction mixture was cooled down to room temperature and the two phases were separated. The aqueous phase was extracted with ethyl acetate three times and the organic phases combined, dried over MgSO$_4$, filtered and evaporated. The residue was triturated from diethyl ether (20 mL) and the product was filtered and dried in vacuo to provide the title compound as an off-white solid (9.96 g). The mother liquor was concentrated in vacuo and purified by column chromatography (silica gel, gradient 0 to 100% ethyl acetate/isohexane) yielding a further 1.79 g of the title compound.

Step 5: 2-(4-Chloro-3,5-diphenyl-pyrazolo[3,4-c]pyridazin-1-yl)ethanol

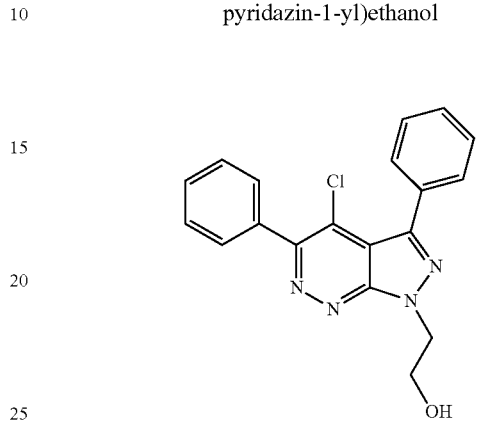

Sodium nitrite (3.42 g, 49.5 mmol) was added portionwise to cHCl (165 mL) at −10° C. and stirred for 20 min. 2-[5-amino-3-phenyl-4-(2-phenylethynyl)pyrazol-1-yl]ethanol (5 g, 16.5 mmol) was added as a solid. The reaction mixture was allowed to warm up, sonicated for 5 min then stirred at room temperature for 2 h. The reaction mixture was diluted with CH$_2$Cl$_2$ and water and the aqueous phase was extracted with CH$_2$Cl$_2$. The organic phases where combined, dried over MgSO$_4$, filtered and evaporated. The residue was partially purified by column chromatography (silica gel, gradient 0 to 100% ethyl acetate/isohexane). The resulting residue was then triturated from diethyl ether, yielding the title compound as a solid (956 mg).

Step 6: 4-Chloro-1-(2-iodoethyl)-3,5-diphenyl-1H-pyrazolo[3,4-c]pyridazine

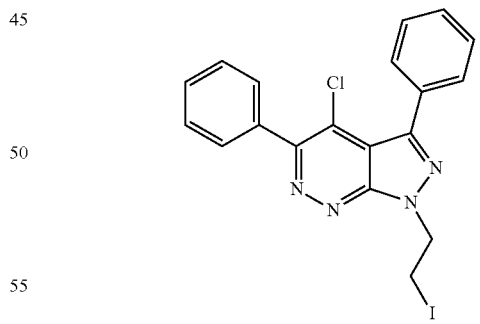

Triphenylphosphine (160 mg, 0.62 mmol), imidazole (42 mg, 0.62 mmol) and iodine (160 mg, 0.62 mmol) were added to a solution of 2-(4-chloro-3,5-diphenyl-1Hpyrazolo[3,4-c]pyridazin-1-yl)ethanol (181 mg, 0.52 mmol) in CH$_2$Cl$_2$ (6 mL). After stirring at ambient temperature for 1 h the reaction was filtered and solvent removed in vacuo. Purification using chromatography (silica gel, gradient 10 to 60% ethyl acetate/isohexane) gave 4-chloro-1-(2-iodoethyl)-3,5-diphenyl-1H-pyrazolo[3,4-c]pyridazine as a clear oil (202 mg) which was used as such in the subsequent step.

Step 7: 4-Chloro-1-[2-[(3S)-3-fluoropyrrolidin-1-yl]ethyl]-3,5-diphenyl-pyrazolo[3,4-c]pyridazine (Compound IIt)

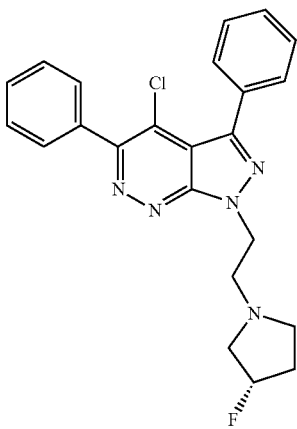 [SMILES: F[C@H]1CCN(CCn2nc(-c3ccccc3)c3c(Cl)c(-c4ccccc4)nnc32)C1]

A solution of 4-chloro-1-(2-iodoethyl)-3,5-diphenyl-1H-pyrazolo[3,4-c]pyridazine (90 mg, 0.2 mmol) in dry $CH_2Cl_2$ (2 mL) was added to (S)-3-fluoropyrrolidine hydrochloride (126 mg, 1 mmol), DIPEA (0.21 mL, 1.2 mmol) was added and the reaction stirred for 2 days. Further $CH_2Cl_2$ (3 mL), (S)-3-fluoropyrrolidine hydrochloride (126 mg, 1 mmol) and DIPEA (0.21 mL, 1.2 mmol) was added and the reaction stirred for an additional 7 days. The resultant residue was purified using chromatography (silica gel, gradient 20 to 100% ethyl acetate/isohexane), followed by preparative HPLC to provide Compound IIt as a white solid (25 mg).

$^1$H NMR δ (ppm) (DMSO-$d_6$): 7.76-7.70 (2 H, m), 7.70-7.66 (2 H, m), 7.53-7.43 (6 H, m), 5.15-5.01 (1 H, m), 4.83 (2 H, t), 3.07 (2 H, t), 2.93-2.77 (2 H, m), 2.74-2.58 (1 H, m), 2.41-2.45 (1 H, m), 2.07-1.90 (1 H, m), 1.82-1.68 (1 H, m).

LCMS (15 cm_Bicarb_GeminiNX_HPLC_CH3CN) Rt 11.27 min; m/z 422 [M+H] 98.15% purity.

Example 56

4-chloro-1-[2-[(3R)-3-fluoropyrrolidin-1-yl]ethyl]-3,5-diphenyl-pyrazolo[3,4-c]pyridazine (Compound IIu)

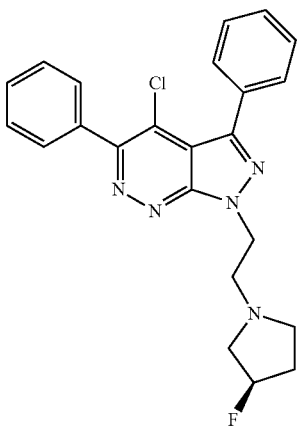 [SMILES: F[C@@H]1CCN(CCn2nc(-c3ccccc3)c3c(Cl)c(-c4ccccc4)nnc32)C1]

Compound IIu was synthesized according to Example 55, but using (R)-3-fluoropyrrolidine hydrochloride instead of (S)-3-fluoropyrrolidine hydrochloride.

$^1$H NMR δ (ppm) (DMSO-$d_6$): 7.76-7.70 (2 H, m), 7.70-7.66 (2 H, m), 7.53-7.43 (6 H, m), 5.15-5.01 (1 H, m), 4.83 (2 H, t), 3.07 (2 H, t), 2.93-2.77 (2 H, m), 2.74-2.58 (1 H, m), 2.41-2.45 (1 H, m), 2.07-1.90 (1 H, m), 1.82-1.68 (1 H, m).

LCMS (10 cm_ESCI_Formic_MeCN) Rt 2.84 min; m/z 422 [M+H] 98.06% purity.

Example 57

4-chloro-1-[2-(3,3-difluoropyrrolidin-1-yl)ethyl]-3,5-diphenyl-pyrazolo[3,4-c]pyridazine (Compound IIv)

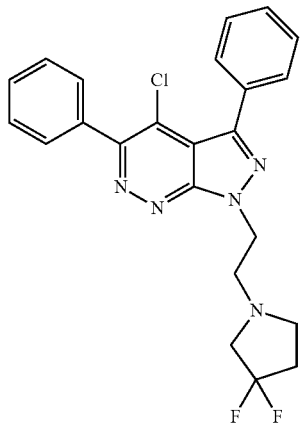 [SMILES: FC1(F)CCN(CCn2nc(-c3ccccc3)c3c(Cl)c(-c4ccccc4)nnc32)C1]

A solution of 4-chloro-1-(2-iodoethyl)-3,5-diphenyl-1H-pyrazolo[3,4-c]pyridazine (91 mg, 0.2 mmol) in dry $CH_2Cl_2$ (2 mL) was added to 3,3-difluoropyrrolidine hydrochloride (143 mg, 1 mmol), DIPEA (0.2 mL, 1.1 mmol) was added and the reaction stirred for 5 days. The resultant residue was purified using chromatography (silica gel, gradient 20 to 50% ethyl acetate/isohexane), followed by preparative HPLC to provide Compound IIv as a white solid (24.5 mg).

$^1$H NMR δ (ppm) (DMSO-$d_6$): 7.74-7.70 (2 H, m), 7.70-7.65 (2 H, m), 7.52-7.41 (6 H, m), 4.84 (2 H, t), 3.07 (2 H, t), 2.97 (2 H, t), 2.75 (2 H, t), 2.16-2.03 (2 H, m).

LCMS (10 cm_ESCI_Formic_MeCN) Rt 4.45 min; m/z 440 [M+H] 99.4% purity.

Example 58

4-chloro-1-[2-(3,3-difluoroazetidin-1-yl)ethyl]-3,5-diphenyl-pyrazolo[3,4-c]pyridazine (Compound 11w)

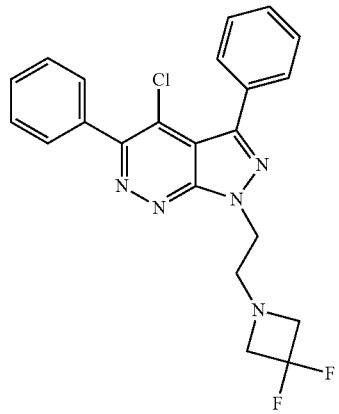 [SMILES: FC1(F)CN(CCn2nc(-c3ccccc3)c3c(Cl)c(-c4ccccc4)nnc32)C1]

Compound IIw was synthesized according to Example 57, but using 3,3-difluoroazetidine hydrochloride instead of 3,3-difluoropyrrolidine hydrochloride.

$^1$H NMR δ (ppm) (DMSO-d$_6$): 7.74-7.70 (2 H, m), 7.70-7.66 (2 H, m), 7.53-7.43 (6 H, m), 4.74 (2 H, t), 3.56 (4 H, t), 3.15 (2 H, t).

LCMS (10 cm_ESCI_Formic_MeCN) Rt 4.35 min; m/z 426 [M+H] 95.4% purity.

Example 59

4-chloro-3-(3-fluorophenyl)-1-[2-[(3R)-3-fluoropyrrolidin-1-yl]ethyl]-5-phenyl-pyrazolo[3,4-c]pyridazine (Compound IIx)

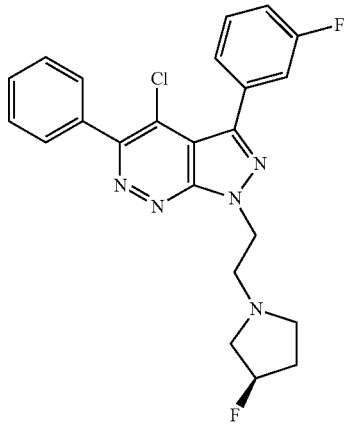 [SMILES: Fc1cccc(-c2nn(CCN3CC[C@@H](F)C3)c3nnc(-c4ccccc4)c(Cl)c23)c1]

Compound IIx was synthesized according to Example 1, using 3-fluorophenylboronic acid instead of 1-methyl-4-(4,4,5,5-tetramethyl-1,3,2-dioxaborolan-2-yl)-1H-pyrazole and 4-chloro-1-[2-[(3R)-3-fluoropyrrolidin-1-yl]ethyl]-3-iodo-5-phenyl-pyrazolo[3,4-c]pyridazine instead of 4-chloro-3-iodo-1-(2-(4-methylpiperazin-1-yl)ethyl)-5-phenyl-1H-pyrazolo[3,4-c]pyridazine in Step 8.

$^1$H NMR δ (ppm) (CHCl$_3$-d): 7.79-7.75 (2 H, m), 7.60-7.44 (6 H, m), 7.18 (1 H, tdd), 5.22-5.04 (1 H, m), 4.96 (2 H, t), 3.25 (2 H, t), 3.01-2.91 (3 H, m), 2.68 (1 H, q), 2.13-1.96 (2 H, m).

LCMS (15 cm_Bicarb_GeminiNX_HPLC_CH3CN) Rt 11.32 min; m/z 440 [M+H] 96.24% purity.

Example 60

4-chloro-3-(4-fluorophenyl)-1-[2-[(3R)-3-fluoropyrrolidin-1-yl]ethyl]-5 phenyl-pyrazolo[3,4-c]pyridazine (Compound IIy)

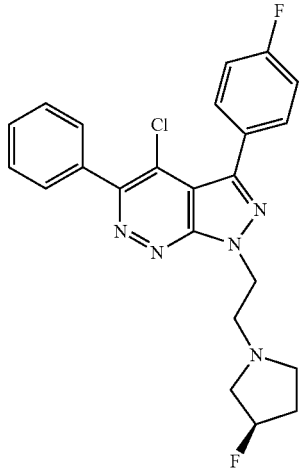 [SMILES: Fc1ccc(-c2nn(CCN3CC[C@@H](F)C3)c3nnc(-c4ccccc4)c(Cl)c23)cc1]

Compound IIy was synthesized according to Example 1, but using 4-fluorophenylboronic acid instead of 1-methyl-4-(4,4,5,5-tetramethyl-1,3,2-dioxaborolan-2-yl)-1H-pyrazole and 4-chloro-1-[2-[(3R)-3-fluoropyrrolidin-1-yl]ethyl]-3-iodo-5-phenyl-pyrazolo[3,4-c]pyridazine instead of 4-chloro-3-iodo-1-(2-(4-methylpiperazin-1-yl)ethyl)-5-phenyl-1H-pyrazolo[3,4-c]pyridazine in Step 8.

$^1$H NMR δ (ppm) (CHCl$_3$-d): 7.78-7.73 (4 H, m), 7.55-7.46 (3 H, m), 7.23-7.15 (2 H, m), 5.21-5.03 (1 H, m), 4.95 (2 H, t), 3.24 (2 H, t), 3.01-2.91 (3 H, m), 2.68 (1 H, q), 2.12-1.96 (2 H, m).

LCMS (15 cm_Bicarb_GeminiNX_HPLC_CH3CN) Rt 11.29 min; m/z 440 [M+H] 93.55% purity.

Scheme V: General Scheme for Synthesising Compounds of Formula III

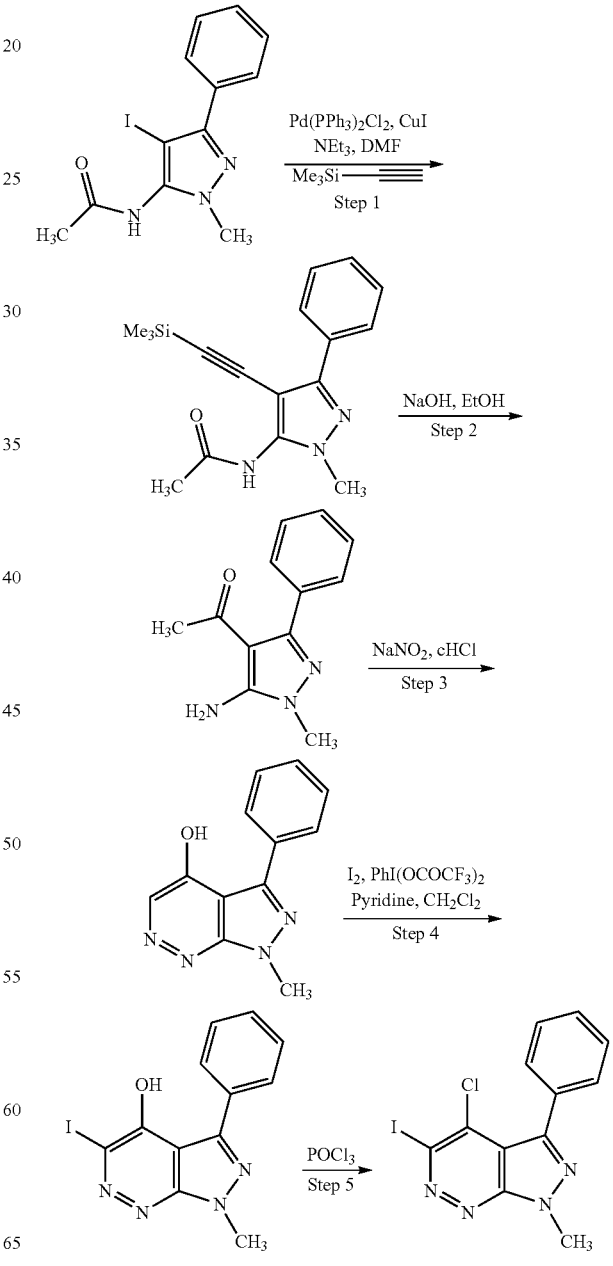

Example 61

4-chloro-5-iodo-1-methyl-3-phenyl-pyrazolo[3,4-c]pyridazine (Compound IIIa)

Step 1: N-(1-methyl-3-phenyl-4-((trimethylsilyl)ethynyl)-H-pyrazol-5-yl)acetamide

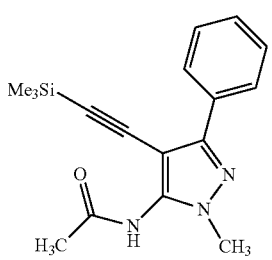 [SMILES: CC(=O)Nc1c(C#C[Si](C)(C)C)c(-c2ccccc2)nn1C]

Nitrogen was bubbled through a mixture of N-(4-iodo-1-methyl-3-phenyl-1H-pyrazol-5-yl)acetamide (5 g, 15 mmol) in DMF (15 mL) and triethylamine (35 mL) for 15 min. Copper iodide (0.56 g, 3.0 mmol), bis(triphenylphosphine)palladium(II) dichloride (0.53 g, 0.75 mmol) and ethynyltrimethylsilane (3.0 g, 30 mmol) were added and the reaction mixture was stirred in a sealed tube at 90° C. under nitrogen for 3 h. The reaction mixture was cooled to room temperature, diluted with ethyl acetate and water. The organic phase was washed with water and brine, dried (phase separation cartridge) and concentrated in vacuo. The residue was purified by column chromatography (silica gel, isohexane/ethyl acetate 5:1 to 10:3) yielding the title compound as a solid (2.3 g).

Step 2: 1-(5-amino-1-methyl-3-phenyl-pyrazol-4-yl)ethanone

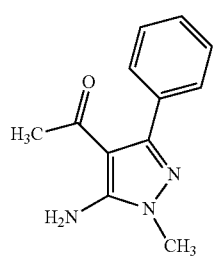 [SMILES: CC(=O)c1c(-c2ccccc2)nn(C)c1N]

A mixture of N-(1-methyl-3-phenyl-4-((trimethylsilyl)ethynyl)-1H-pyrazol-5-yl)acetamide (2.3 g, 7.4 mmol), ethanol (20 mL) and 25% aq. NaOH solution (20 mL) was heated with stirring at 90° C. for 6 h and cooled to room temperature. The reaction mixture was diluted with ethyl acetate and water. The organic phase was washed with water and brine, dried (phase separator cartridge) and concentrated in vacuo. The residue was purified using chromatography (silica gel, gradient 0 to 40% ethyl acetate/$CH_2Cl_2$), followed by trituration in diethyl ether to provide the title compound as a white solid (724 mg).

Step 3: 1-methyl-3-phenyl-pyrazolo[3,4-c]pyridazin-4-ol

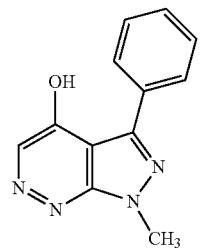 [SMILES: Cn1nc(-c2ccccc2)c2c(O)cnnc21]

A suspension of 1-(5-amino-1-methyl-3-phenyl-pyrazol-4-yl)ethanone (241 mg, 1.12 mmol) in cHCl (6.7 mL) and water (1 mL) was cooled to −5° C. A solution of sodium nitrite (155 mg, 2.24 mmol) in water (0.6 mL) was added and the reaction mixture was stirred at −5° C. for 20 min, then at room temperature for 10 min, then at 65° C. for 30 min and finally cooled to room temperature. The reaction mixture was filtered and the solid was washed with cHCl (2 mL), suspended in MeOH/$CH_2Cl_2$ (9:1), filtered and dried, to yield the title compound as a solid (125 mg).

Step 4: 5-iodo-1-methyl-3-phenyl-pyrazolo[3,4-c]pyridazin-4-ol

Phenyl[bis(2,2,2-trifluoroacetoxy)]-$\lambda^3$-iodane (190 mg, 0.43 mmol) was added to a suspension of 1-methyl-3-phenyl-pyrazolo[3,4-c]pyridazin-4-ol (166 mg, 0.73 mmol) in $CH_2Cl_2$ (3.7 mL), followed by the addition of iodine (111 mg, 0.43 mmol) and pyridine (71 µL). The reaction mixture was stirred at room temperature for 16 h, then filtered. The collected solid was washed with $CH_2Cl_2$ and dried, to yield the title compound (160 mg).

Step 5: 4-chloro-5-iodo-1-methyl-3-phenyl-pyrazolo[3,4-c]pyridazine (Compound IIIa)

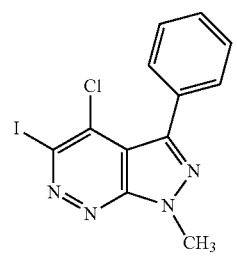 [SMILES: Cn1nc(-c2ccccc2)c2c(O)c(I)nnc21]

5-Iodo-1-methyl-3-phenyl-pyrazolo[3,4-c]pyridazin-4-ol (160 mg, 0.45 mmol) in phosphorous oxychloride (0.6 mL) was heated to 120° C. for 10 min. The reaction mixture was cooled to room temperature and the suspension was filtered. The collected solid was dissolved in $CH_2Cl_2$ and washed with water. The organic phase was dried (phase separator cartridge) and concentrated in vacuo, to yield Compound IIIa (130 mg).

$^1$H NMR δ (ppm) (DMSO-$d_6$): 7.80-7.76 (2 H, m), 7.62-7.56 (3 H, m), 4.43-4.35 (3 H, m).

LCMS (10 cm_ESCI_Formic_MeCN) Rt 4.52 min; m/z 371 [M+H] 97.73% purity.

Example 62

4-chloro-5-(cyclopenten-1-yl)-1-methyl-3-phenyl-pyrazolo[3,4-c]pyridazine (Compound IIIb)

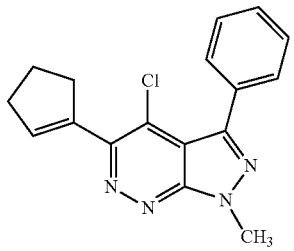 [SMILES: Cn1nc(-c2ccccc2)c2c(Cl)c(C3=CCCC3)nnc21]

Nitrogen was bubbled through a suspension of 4-chloro-5-iodo-1-methyl-3-phenyl-pyrazolo[3,4-c]pyridazine (60 mg, 0.16 mmol), 2-(cyclopenten-1-yl)-4,4,5,5-tetramethyl-1,3,2-dioxaborolane (35 mg, 0.18 mmol) and $K_3PO_4$ (103 mg, 0.48 mmol) in DMF (1 mL) and water (0.3 mL) for 15 min. 1,1'-Bis(diphenylphosphino)ferrocene-palladium(II)dichloride dichloromethane complex (13 mg, 0.016 mmol) was added and the tube sealed and heated to 30° C. for 16 h. The reaction mixture was diluted with $CH_2Cl_2$ and water. The aqueous phase was extracted with $CH_2Cl_2$ and the combined organic phases were dried (phase separator cartridge) and concentrated in vacuo. The resultant residue was purified using chromatography (silica gel, $CH_2Cl_2$/isohexane 1:1 to 1:0), to provide Compound IIIb as a solid (10 mg).

$^1$H NMR δ (ppm) ($CHCl_3$-d): 7.75-7.69 (2 H, m), 7.52-7.46 (3 H, m), 6.62-6.59 (1 H, m), 4.39 (3 H, s), 3.11-3.04 (2 H, m), 2.71-2.64 (2 H, m), 2.14-2.04 (2 H, m).

LCMS (15 cm_Bicarb_GeminiNX_HPLC_CH3CN) Rt 11.75 min; m/z 311 [M+H] 93.15% purity.

Example 63

4-chloro-1-methyl-3-phenyl-5-(3-thienyl)pyrazolo[3,4-c]pyridazine (Compound IIIc)

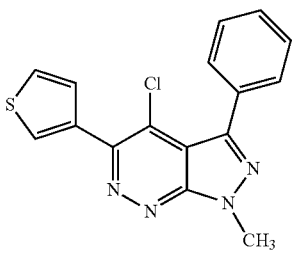 [SMILES: Cn1nc(-c2ccccc2)c2c(Cl)c(-c3ccsc3)nnc21]

Compound IIIc was synthesized according to Example 19, but using N-(2-methyl-5-phenyl-pyrazol-3-yl)acetamide instead of N-(3-methyl-1H-pyrazol-5-yl)acetamide in Step 2 and using 3-ethynylthiophene instead of phenylacetylene in Step 3.

$^1$H NMR δ (ppm) ($CHCl_3$-d): 8.01 (1H, dd), 7.79-7.75 (3H, m), 7.53-7.49 (3H, m), 7.46 (1H, dd), 4.44 (3H, s).

LCMS (15 cm_Formic_ASCENTIS_HPLC_CH3CN) Rt 10.65 min; m/z 327 [M+H] 98.32% purity.

Example 64

4-chloro-1-methyl-3-phenyl-5-(3-pyridyl)pyrazolo[3,4-c]pyridazine (Compound IIId)

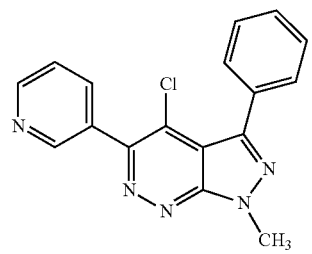 [SMILES: Cn1nc(-c2ccccc2)c2c(Cl)c(-c3cccnc3)nnc21]

Compound IIId was synthesized according to Example 19, but using N-(2-methyl-5-phenyl-pyrazol-3-yl)acetamide instead of N-(3-methyl-1H-pyrazol-5-yl)acetamide in Step 2 and using 3-ethynylpyridine instead of phenylacetylene in Step 3.

$^1$H NMR δ (ppm) ($CHCl_3$-d): 9.06 (1 H, s), 8.74 (1 H, s), 8.14 (1 H, dt), 7.79-7.74 (2 H, m), 7.55-7.43 (4 H, m), 4.47 (3 H, s).

LCMS (15 cm_Formic_ASCENTIS_HPLC_CH3CN) Rt 8.99 min; m/z 322 [M+H] 98.02% purity.

Example 65

4-chloro-3-cyclopropyl-1-methyl-5-phenyl-pyrazolo[3,4-c]pyridazine (Compound 21)

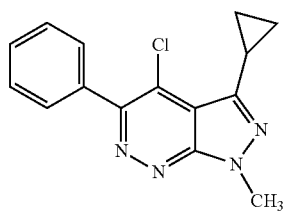 [SMILES: Cn1nc(C2CC2)c2c(Cl)c(-c3ccccc3)nnc21]

Compound 21 was synthesized according to Example 19, but using N-(5-cyclopropyl-2-methyl-pyrazol-3-yl)acetamide instead of N-(3-methyl-1H-pyrazol-5-yl)acetamide in Step 2.

$^1$H NMR δ (ppm) ($CHCl_3$-d): 7.78 (2 H, m), 7.57-7.47 (3 H, m), 4.26 (3 H, s), 2.61-2.52 (1 H, m), 1.13-1.08 (4 H, m).

LCMS (10 cm_ESCI_Bicarb_MeCN) Rt 3.79 min; m/z 285 [M+H] 99.51% purity.

Example 66

4-chloro-1,3-dimethyl-5-phenyl-pyrazolo[3,4-c]pyridazine (Compound 22)

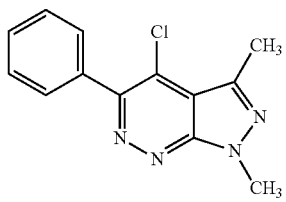 [SMILES: Cc1nn(C)c2nnc(-c3ccccc3)c(Cl)c12]

Compound 22 can be synthesized according to Vasilevsky, S. F. and Tretyakov, E. V. (1995), "Cinnolines and pyrazolopyridazines: Novel synthetic and mechanistic aspects of the Richter reaction." *Liebigs Ann./Recl.,* 1995: 775-779.

$^1$H NMR δ (ppm) (CHCl$_3$-d): 7.79-7.75 (2 H, m), 7.56-7.47 (3 H, m), 4.30 (3 H, s), 2.80 (3 H, s).

LCMS (10 cm_ESI_Formic_MeCN) Rt 3.69 min; m/z 259 [M+H] 99.32% purity.

Example 67

4-bromo-1,3-dimethyl-5-phenyl-pyrazolo[3,4-c]pyridazine (Compound 23)

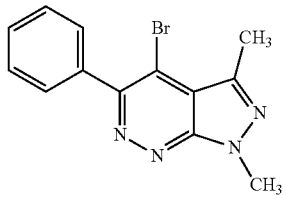 [SMILES: Cc1nn(C)c2nnc(-c3ccccc3)c(Br)c12]

Compound 23 can be synthesized according to Vasilevsky, S. F. and Tretyakov, E. V. (1995), "Cinnolines and pyrazolopyridazines: Novel synthetic and mechanistic aspects of the Richter reaction." *Liebigs Ann./Recl.,* 1995: 775-779.

$^1$H NMR δ (ppm) (CHCl$_3$-d): 7.73-7.70 (2 H, m), 7.55-7.46 (3 H, m), 4.30 (3 H, s), 2.80 (3 H, s).

LCMS (10 cm_ESI_Formic_MeCN) Rt 3.74 min; m/z 303 [M+H] 99.15% purity.

Example 68

4-fluoro-1,3-dimethyl-5-phenyl-pyrazolo[3,4-c]pyridazine (Compound 24)

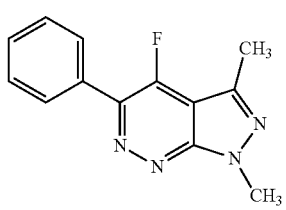 [SMILES: Cc1nn(C)c2nnc(-c3ccccc3)c(F)c12]

A suspension of 4-chloro-1,3-dimethyl-5-phenyl-pyrazolo[3,4-c]pyridazine (44 mg, 0.17 mmol), potassium fluoride (50 mg, 0.85 mmol) in dry DMF (1 mL) was stirred at 120° C. for 16 h. The reaction mixture was purified by preparative HPLC to provide Compound 24 (12 mg).

$^1$H NMR δ (ppm) (CHCl$_3$-d): 8.04-8.00 (2 H, m), 7.58-7.46 (3 H, m), 4.31 (3 H, s), 2.75 (3 H, s).

LCMS (15 cm_Bicarb_GeminiNX_HPLC_CH3CN) Rt 10.25 min; m/z 243 [M+H] 91.64% purity.

Example 69

4-chloro-5-(3-fluorophenyl)-1,3-dimethyl-pyrazolo[3,4-c]pyridazine (Compound 25)

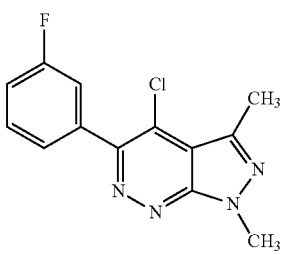 [SMILES: Cc1nn(C)c2nnc(-c3cccc(F)c3)c(Cl)c12]

Compound 25 was synthesized according to Example 19, but using N-(2,5-dimethylpyrazol-3-yl)acetamide instead of N-(3-methyl-1H-pyrazol-5-yl)acetamide in Step 2 and using 3-fluorophenylacetylene instead of phenylacetylene in Step 3.

$^1$H NMR δ (ppm) (CHCl$_3$-d): 7.59-7.46 (3 H, m), 7.23-7.17 (1 H, m), 4.31 (3 H, s), 2.80 (3 H, s).

LCMS (10 cm_ESCI_Bicarb_MeCN) Rt 4.01 min; m/z 277 [M+H] 99.46% purity.

Example 70

4-chloro-1-methyl-5-phenyl-3-(3-pyridyl)pyrazolo[3,4-c]pyridazine (Compound 26)

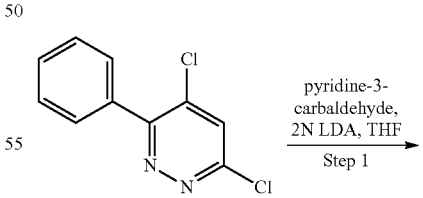

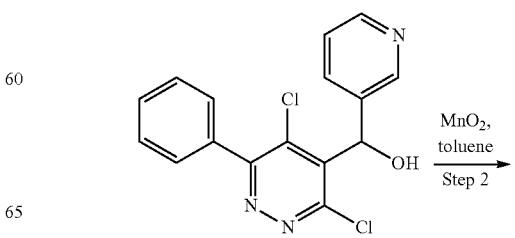

Step 1: (3,5-dichloro-6-phenyl-pyridazin-4-yl)-(3-pyridyl)methanol

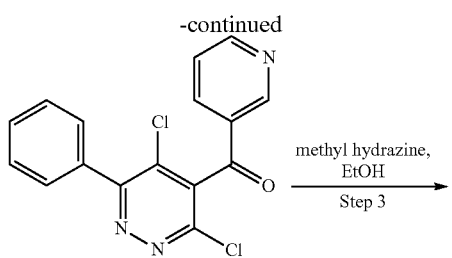

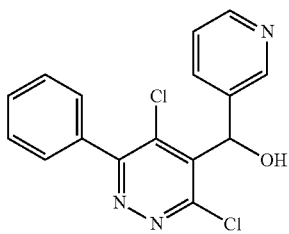 [SMILES: OC(c1cccnc1)c1c(Cl)nnc(-c2ccccc2)c1Cl]

To a solution of 4,6-dichloro-3-phenyl-pyridazine (2.27 g, 0.01 mol) in dry THF (30 mL) was added pyridine-3-carbaldehyde (1.3 g, 0.012 mol). The reaction mixture was cooled down to −78° C. and a solution of LDA (2 N, 22 mL) was added dropwise, keeping the internal temperature below −50° C. The reaction mixture was stirred for 3 h, then water and ethyl acetate were added. Phases were separated and the aqueous phase was extracted with ethyl acetate. The combined organic phases were dried (phase separator cartridge) and concentrated in vacuo. The residue was purified by column chromatography (silica gel, isohexane/ethyl acetate 9:1 to 8:2) yielding the title compound as a solid (4.1 g).

Step 2: (3,5-dichloro-6-phenyl-pyridazin-4-yl)-(3-pyridyl)methanone

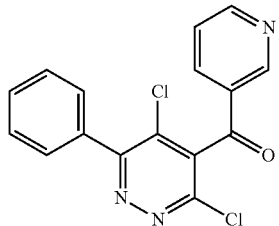 [SMILES: O=C(c1cccnc1)c1c(Cl)nnc(-c2ccccc2)c1Cl]

A mixture of 3,5-dichloro-6-phenyl-pyridazin-4-yl)-(3-pyridyl)methanol (850 mg, 2.57 mmol) and manganese dioxide (1.1 g, 12.8 mmol) in toluene (20 mL) was stirred at reflux in a Dean-Stark apparatus for 2 h. The reaction mixture was filtered and the collected solid was washed with CH₂Cl₂. The filtrate was concentrated in vacuo and the residue was purified by column chromatography (silica gel, isohexane/ethyl acetate 8:2) yielding the title compound as a solid (360 mg).

Step 3: 4-chloro-1-methyl-5-phenyl-3-(3-pyridyl)pyrazolo[3,4-c]pyridazine (Compound 26)

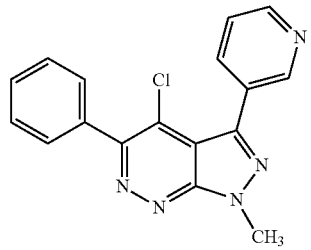

A mixture of (3,5-dichloro-6-phenyl-pyridazin-4-yl)-(3-pyridyl)methanone (100 mg, 0.3 mmol) and methyl hydrazine (19.5 mg, 0.42 mmol) in ethanol (1.5 mL) was stirred in a sealed tube at 60° C. for 3 h. The reaction mixture was concentrated in vacuo and the residue was purified by column chromatography (silica gel, isohexane/ethyl acetate 9:1 to 8:2) yielding Compound 26 as a solid (30 mg).

¹H NMR δ (ppm) (CHCl₃-d): 9.05 (1 H, m), 8.73 (1 H, dd), 8.12 (1 H, dt), 7.79-7.76 (2 H, m), 7.57-7.48 (3 H, m), 7.46 (1 H, dd), 4.48 (3 H, s).

LCMS (10 cm_ESCI_Formic_MeCN) Rt 3.6 min; m/z 322 [M+H] 98.72% purity.

Example 71

4-chloro-3-cyclopentyl-1-methyl-5-phenyl-pyrazolo[3,4-c]pyridazine (Compound 27)

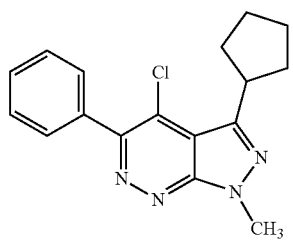 [SMILES: Cn1nc(C2CCCC2)c2c(Cl)c(-c3ccccc3)nnc21]

Compound 27 was synthesized according to Example 70, but using cyclopentane carboxaldehyde instead of pyridine-3-carbaldehyde in Step 1.

¹H NMR δ (ppm) (CHCl₃-d): 7.77 (2 H, m), 7.57-7.47 (3 H, m), 4.30 (3 H, s), 3.87-3.77 (1 H, m), 2.22-2.14 (2 H, m), 2.06-1.93 (2 H, m), 1.95-1.83 (2 H, m), 1.80-1.71 (2 H, m).

LCMS (15 cm_Bicarb_GeminiNX_HPLC_CH3CN) Rt 11.97 min; m/z 313 [M+H] 98.14% purity.

Example 72

4-chloro-2-methyl-3,5-diphenyl-pyrazolo[3,4-c]pyridazine (Compound 28)

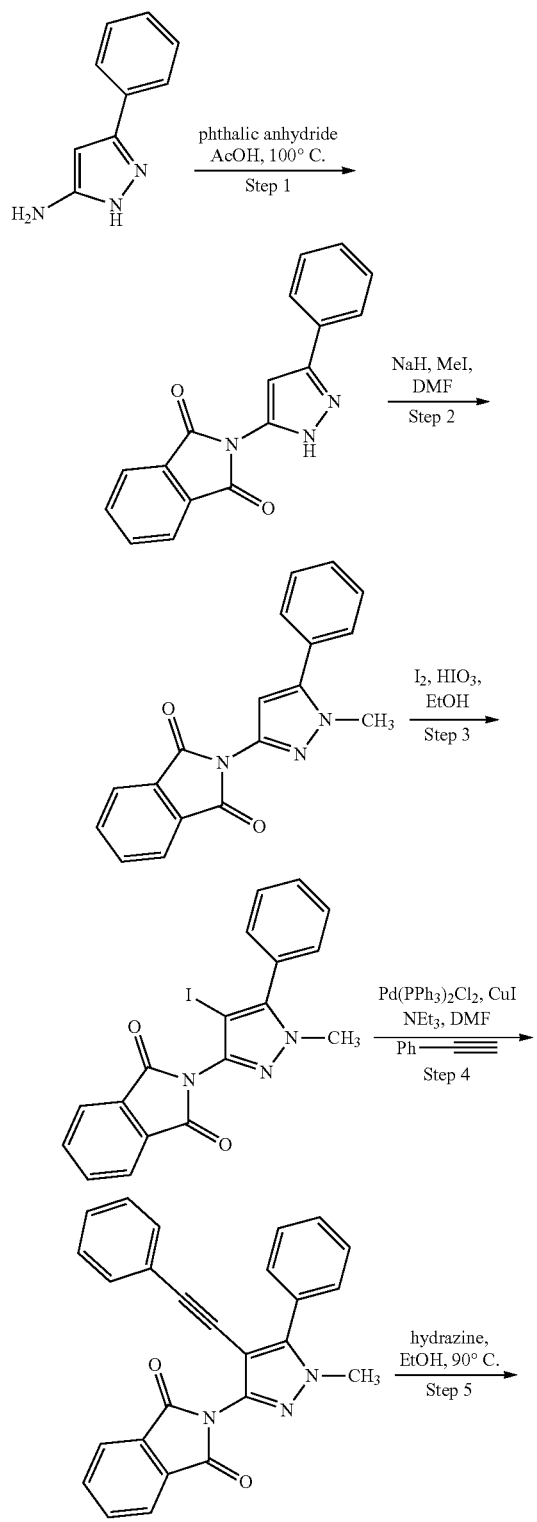

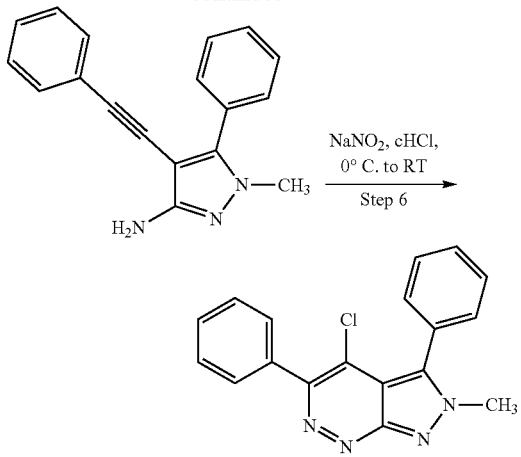

Step 1: 2-(3-phenyl-1H-pyrazol-5-yl)isoindoline-1,3-dione

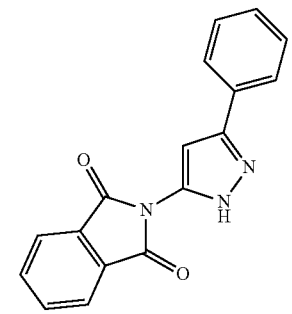 [SMILES: O=C1c2ccccc2C(=O)N1c1cc(-c2ccccc2)n[nH]1]

A mixture of 3-phenyl-1H-pyrazol-5-amine (6 g, 0.038 mol), phthalic anhydride (5.6 g, 0.038 mol) in acetic acid (60 mL) was heated at 100° C. for 2 h and at 120° C. for 2 h and cooled to room temperature. The reaction mixture was diluted with water and the suspension was filtered. The collected solid was washed with water, dried, yielding the title compound as a solid (10 g).

Step 2: 2-(2-methyl-5-phenyl-pyrazol-3-yl)isoindoline-1,3-dione

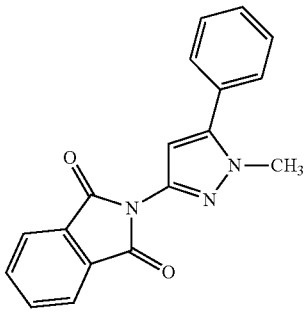 [SMILES: Cn1nc(N2C(=O)c3ccccc3C2=O)cc1-c1ccccc1]

Sodium hydride (830 mg, 0.02 mol) was added portionwise to a mixture of 2-(3-phenyl-1H-pyrazol-5-yl)isoindoline-1,3-dione (5 g, 0.0173 mol) and methyl iodide (1.5 mL, 0.024 mol) in DMF (80 mL) at 10° C. The reaction mixture was stirred at room temperature for 16 h. The reaction mixture was diluted with water and the aqueous phase was extracted with ethyl acetate twice. The combined organic phases were dried (MgSO$_4$), filtered and concentrated in vacuo. The residue was purified by column chromatography (silica gel, ethyl acetate/isohexane 1:19 to 2:8) yielding a mixture of the title compound and the regioisomer 2-(2-methyl-5-phenyl-pyrazol-3-yl)isoindoline-1,3-dione (850 mg, 5:1).

Step 3: 2-(4-iodo-1-methyl-5-phenyl-pyrazol-3-yl)isoindoline-1,3-dione

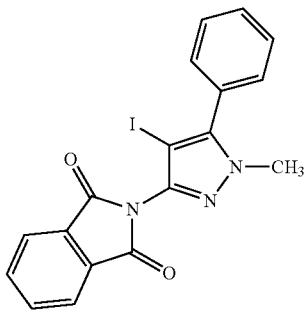 [SMILES: Cn1nc(N2C(=O)c3ccccc3C2=O)c(I)c1-c1ccccc1]

A suspension of 2-(2-methyl-5-phenyl-pyrazol-3-yl)isoindoline-1,3-dione (850 mg 2.8 mmol), iodic acid (123 mg, 0.7 mmol) and iodine (427 mg, 1.68 mmol) in ethanol (30 mL) was heated at 50° C. for 2 h and cooled to room temperature. The reaction mixture was concentrated in vacuo. The residue was partially purified by column chromatography (silica gel, CH$_2$Cl$_2$), then triturated with diethyl ether, yielding the title compound as a solid (660 mg).

Step 4: 2-[1-methyl-5-phenyl-4-(2-phenylethynyl)pyrazol-3-yl]isoindoline-1,3-dione

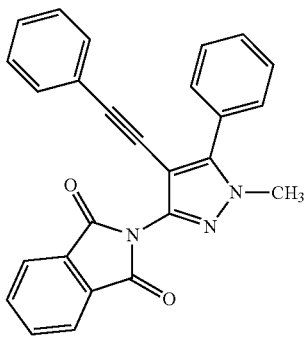 [SMILES: Cn1nc(N2C(=O)c3ccccc3C2=O)c(C#Cc2ccccc2)c1-c1ccccc1]

Nitrogen was bubbled through a mixture of 2-(4-iodo-1-methyl-5-phenyl-pyrazol-3-yl)isoindoline-1,3-dione (660 mg, 1.49 mmol), phenyl acetylene (182 mg, 1.78 mmol), triethylamine (8 mL) and DMF (3 mL) for 15 min. Copper iodide (28 mg, 0.149 mmol) and bis(triphenylphosphine)palladium(II) dichloride (52 g, 0.074 mmol) were added and the reaction mixture was stirred at 90° C. under nitrogen for 3 h. The reaction mixture was cooled to room temperature, diluted with ethyl acetate and water. The organic phase was washed with water and brine, dried (MgSO$_4$), filtered and concentrated in vacuo. The residue was purified by column chromatography (silica gel, isohexane/ethyl acetate 8:2 to 6:4) yielding the title compound as a solid (600 mg).

Step 5: 1-methyl-5-phenyl-4-(2-phenylethynyl)pyrazol-3-amine

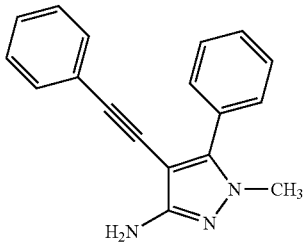 [SMILES: Cn1nc(N)c(C#Cc2ccccc2)c1-c1ccccc1]

A mixture of 2-[1-methyl-5-phenyl-4-(2-phenylethynyl)pyrazol-3-yl]isoindoline-1,3-dione (300 mg, 0.74 mmol), ethanol (5 mL) and hydrazine hydrate (56 µL, 1.11 mL) was stirred in a sealed tube at 90° C. for 1 h and cooled to room temperature. The reaction mixture was filtered. The filtrate was concentrated in vacuo and purified by column chromatography (silica gel, isohexane/ethyl acetate 7:3 to 1:1) yielding the title compound as a solid (150 mg).

Step 6: 4-chloro-2-methyl-3,5-diphenyl-pyrazolo[3,4-c]pyridazine (Compound 28)

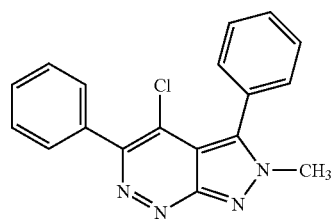 [SMILES: Cn1nc2nnc(-c3ccccc3)c(Cl)c2c1-c1ccccc1]

Sodium nitrite (57 mg, 0.82 mmol) was added portionwise to a mixture of 1-methyl-5-phenyl-4-(2-phenylethynyl)pyrazol-3-amine (150 mg, 0.55 mmol) in cHCl (5 mL) at 0° C. and the reaction mixture was allowed to warm up to room temperature and stirred for 16 h.

The reaction mixture was poured onto a sodium carbonate solution and the aqueous phase was extracted with ethyl acetate three times. The combined organic phases were dried (phase separator cartridge) and concentrated in vacuo. The residue was purified by column chromatography (silica gel, ethyl acetate/isohexane 2:8 to 4:6) yielding Compound 28 as a solid (76 mg).

$^1$H NMR δ (ppm) (CHCl$_3$-d): 7.84-7.80 (2 H, m), 7.60-7.55 (3 H, m), 7.53-7.44 (5 H, m), 4.21 (3 H, s).

LCMS (10 cm_ESCI_Bicarb_MeCN) Rt 3.47 min; m/z 321 [M+H] 97.05% purity.

Example 73

1-[(8-azabicyclo[3.2.1]octan-3-yl]-4-chloro-3-methyl-5-phenyl-pyrazolo[3,4-c]pyridazine (Compound XIIIa)

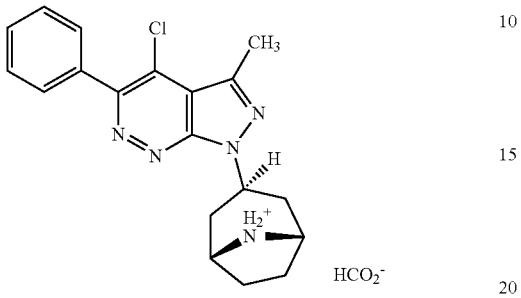

Compound XIIIa was synthesized from 4-chloro-3-methyl-5-phenyl-1H-pyrazolo[3,4-c]pyridazine and nortropine following the general procedure for the Mitsunobu reaction described in Example 20.

$^1$H NMR δ (ppm) (CHCl$_3$-d): 8.62 (1 H, s), 7.77 (2 H, m), 7.57-7.48 (3 H, m), 5.62-5.52 (1 H, m), 4.14 (2 H, s), 2.79 (3 H, s), 2.73 (2 H, m), 2.32 (2 H, m), 2.19-2.06 (4 H, m).

LCMS (15 cm_Formic_ASCENTIS_HPLC_CH3CN) Rt 7.7 min; m/z 354 [M+H] 93.89% purity.

Example 74

4-chloro-1-[(3-methylimidazol-4-yl)methyl]-3-(1-methylpyrrol-2-yl)-5-phenyl-pyrazolo[3,4-c]pyridazine (Compound XIIIb)

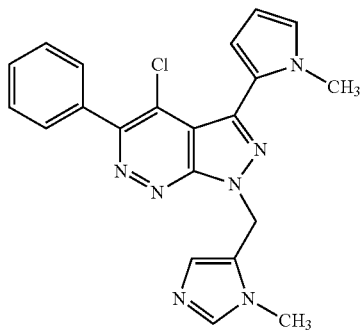 [SMILES: Cn1cncc1Cn1nc(-c2cccn2C)c2c(Cl)c(-c3ccccc3)nnc21]

Compound XIIIb was synthesised following similar procedures of Example 1 (Compound Ic), using (1-methyl-1H-imidazol-5-yl)methanol instead of 2-(4-methylpiperazin-1-yl)ethanol in Step 7 and 1-methyl-2-(4,4,5,5-tetramethyl-1,3,2-dioxaborolan-2-yl)-1H-pyrrole instead of 1-methyl-4-(4,4,5,5-tetramethyl-1,3,2-dioxaborolan-2-yl)-1H-pyrazole in Step 8.

$^1$H NMR δ (ppm) (CHCl$_3$-d): 7.76-7.73 (2 H, m), 7.55-7.46 (3 H, m), 7.43 (1H, s), 7.31 (1 H, s), 6.81 (1 H, t), 6.57 (1 H, dd), 6.25 (1 H, dd), 5.94 (2 H, s), 3.86 (3 H, s), 3.68 (3 H, s).

LCMS (10 cm_Formic_ACE 3 C18 AR_HPLC_CH3CN) Rt 9.81 min; m/z 404 [M+H] 92.03% purity.

Example 75

4-chloro-1-methyl-5-phenyl-3-pyrrolidin-1-yl-pyrazolo[3,4-c]pyridazine (Compound XIIIc)

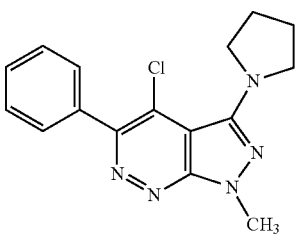 [SMILES: Cn1nc(N2CCCC2)c2c(Cl)c(-c3ccccc3)nnc21]

Step 1: 4-chloro-3-iodo-1-methyl-5-phenyl-1H-pyrazolo[3,4-c]pyridazine

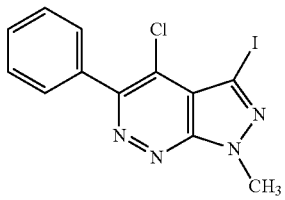 [SMILES: Cn1nc(I)c2c(Cl)c(-c3ccccc3)nnc21]

Sodium hydride (60% in mineral oil, 674 mg, 16.9 mmol) was added to a suspension of 4-chloro-3-iodo-5-phenyl-1H-pyrazolo[3,4-c]pyridazine (3 g, 8.4 mmol) in dry DMF (42 mL) then methyl iodide (1.05 mL, 16.9 mmol) was added. The reaction mixture was stirred for 2 h. LiCl solution (4% in water) and ethyl acetate were added and the aqueous phase was extracted with ethyl acetate. The organic phases were combined, dried (MgSO$_4$), filtered and evaporated. The residue was purified by column chromatography (silica gel, ethyl acetate/isohexane 0:1 to 1:1) yielding the intermediate as a solid (1.51 g).

Step 2: 3-iodo-1-methyl-5-phenyl-1H-pyrazolo[3,4-c]pyridazin-4-ol

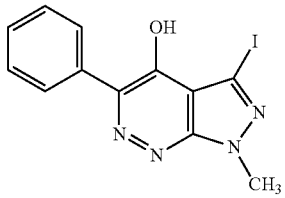 [SMILES: Cn1nc(I)c2c(O)c(-c3ccccc3)nnc21]

A mixture of 4-chloro-3-iodo-1-methyl-5-phenyl-1H-pyrazolo[3,4-c]pyridazine (1.5 g, 4.05 mmol) and NaOH aqueous solution (4 M, 2 mL) in DMSO (6 mL) and dioxane (6 mL) was heated to 50° C. for 2.5 h. The mixture was left to cool to rt, then neutralised to pH 2-3, when a precipitate formed. The solid was filtered, washed with water and dried, to give 1.33 g of the intermediate.

Step 3: 1-methyl-5-phenyl-3-(pyrrolidin-1-yl)-1H-pyrazolo[3,4-c]pyridazin-4-ol

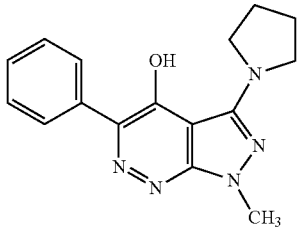 [SMILES: Cn1nc(N2CCCC2)c2c(O)c(-c3ccccc3)nnc21]

A mixture of 3-iodo-1-methyl-5-phenyl-1H-pyrazolo[3,4-c]pyridazin-4-ol (100 mg, 0.28 mmol), copper iodide (11 mg, 0.056 mmol), L-proline (13 mg, 0.11 mmol), $K_2CO_3$ (193 mmol, 1.4 mmol) in anhydrous DMF (5.6 mL) was degassed by bubbling nitrogen through for 10 minutes, then heated to 110° C. for 20 h. The mixture was left to cool to room temperature, then partitioned between ethyl acetate and water, and the aqueous phase was extracted with ethyl acetate. The organic phases were combined, dried ($MgSO_4$), filtered and evaporated. The residue (117 mg) was used as such in the next step.

Step 4: 4-chloro-1-methyl-5-phenyl-3-pyrrolidin-1-yl-pyrazolo[3,4-c]pyridazine (Compound XIIIc)

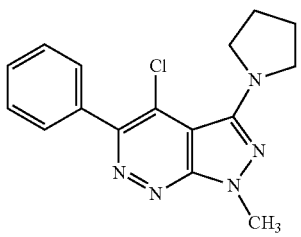 [SMILES: Cn1nc(N2CCCC2)c2c(Cl)c(-c3ccccc3)nnc21]

A suspension of 1-methyl-5-phenyl-3-(pyrrolidin-1-yl)-1H-pyrazolo[3,4-c]pyridazin-4-ol (117 mg) in $POCl_3$ (1.9 mL) was heated to 60° C. for 2.5 h. The mixture was concentrated in vacuo and the residue was partitioned between $CH_2Cl_2$ and sat. aq. $NaHCO_3$ solution. The layers were separated and the aqueous was extracted with $CH_2Cl_2$, the combined organics were dried ($MgSO_4$), filtered and concentrated in vacuo. The residue was purified by chromatography on silica gel to give the title compound (81 mg).

$^1$H NMR δ (ppm) ($CHCl_3$-d): 7.74-7.70 (2 H, m), 7.53-7.44 (3 H, m), 4.18 (3 H, s), 3.62-3.56 (4 H, m), 2.05-1.97 (4 H, m).

LCMS (10 cm_ESCI_Formic_MeCN) Rt 4.55 min; m/z 314.04 [M+H] 97.21% purity.

Example 76

4-chloro-3-methyl-5-phenyl-1-(2-pyrrolidin-1-yl-ethyl)pyrazolo[3,4-c]pyridazine (Compound XIIId)

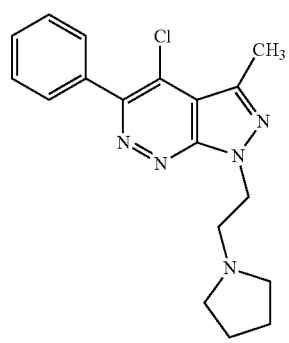 [SMILES: Cc1nn(CCN2CCCC2)c2nnc(-c3ccccc3)c(Cl)c12]

Compound XIIId was synthesized from 4-chloro-3-methyl-5-phenyl-1H-pyrazolo[3,4-c]pyridazine and 2-(pyrrolidin-1-yl)ethanol following the general procedure for the Mitsunobu reaction described in Example 20.

$^1$H NMR δ (ppm) ($CHCl_3$-d): 7.79-7.76 (2 H, m), 7.56-7.47 (3 H, m), 4.82 (2 H, t), 3.11 (2 H, t), 2.80 (3 H, s), 2.64 (4 H, m), 1.78-1.72 (4 H, m).

LCMS (10 cm_Formic_ACE 3 C18 AR_HPLC_CH3CN) Rt 9.07 min; m/z 342 [M+H] 91.77% purity.

Example 77

4-chloro-3,5-diphenyl-1-(2-pyrazol-1-ylethyl)pyrazolo[3,4-c]pyridazine (Compound XIVa)

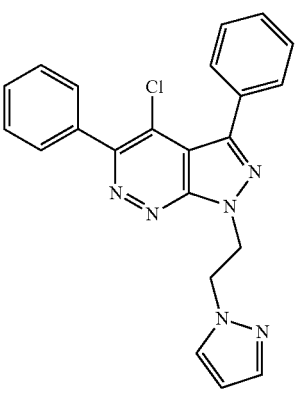 [SMILES: Clc1c(-c2ccccc2)nnc2c1c(-c1ccccc1)nn2CCn1cccn1]

Compound XIVa was synthesized from 4-chloro-3,5-diphenyl-1H-pyrazolo[3,4-c]pyridazine and 2-(1H-pyrazol-1-yl)ethanol following the general procedure for the Mitsunobu reaction described in Example 20.

$^1$H NMR δ (ppm) ($CHCl_3$-d): 7.78-7.69 (4 H, m), 7.55-7.46 (7 H, m), 7.25 (1 H, m), 6.17 (1H, t), 5.25 (2 H, t), 4.87 (2 H, t).

LCMS (10 cm_ESCI_Bicarb_MeCN) Rt 3.67 min; m/z 401 [M+H] 99.6% purity.

Scheme VI: General Scheme for Synthesising Compounds of Formula XIII

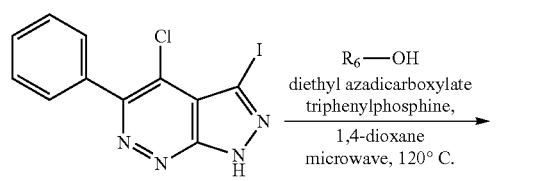

$R_6$—OH
diethyl azadicarboxylate
triphenylphosphine,
1,4-dioxane
microwave, 120° C.

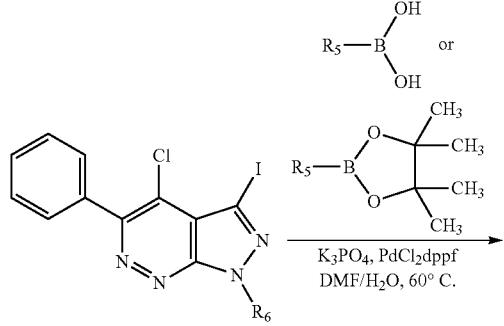

$R_5$—B(OH)$_2$ or $R_5$—Bpin $K_3PO_4$, PdCl$_2$dppf
DMF/H$_2$O, 60° C.

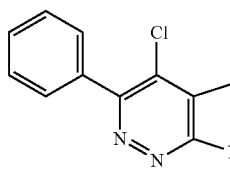

$R_6$—OH

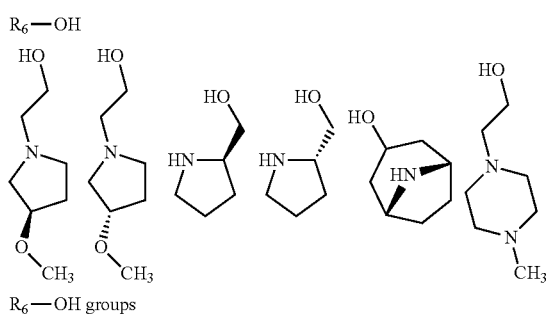

$R_6$—OH groups $R_5$—B(OH)$_2$ or $R_5$—Bpin

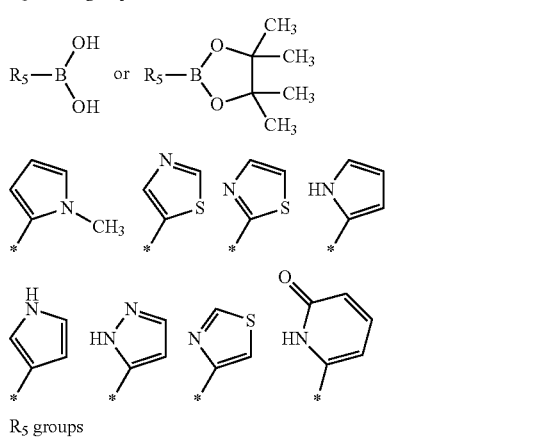

$R_5$ groups

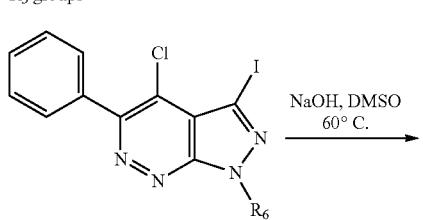

NaOH, DMSO
60° C.

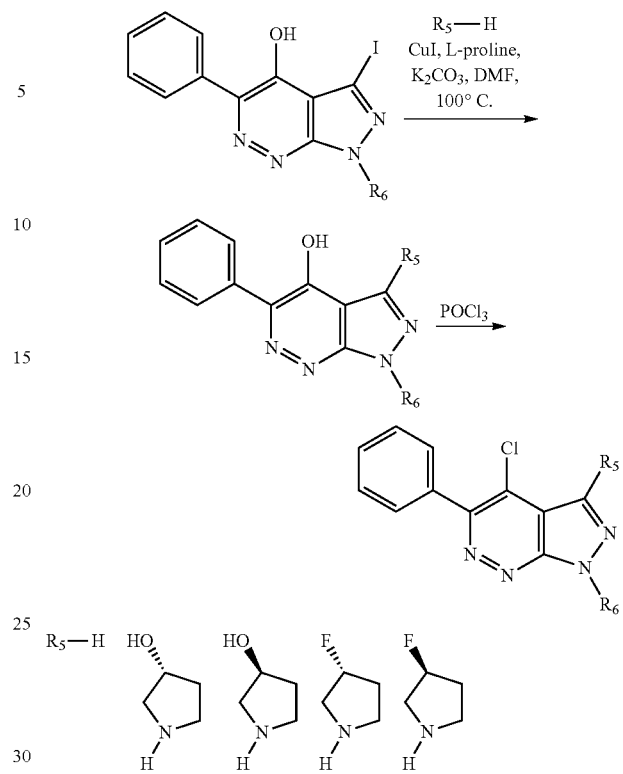

$R_5$—H
CuI, L-proline,
K$_2$CO$_3$, DMF,
100° C.

POCl$_3$ $R_5$—H groups

Scheme VII: General Scheme for Synthesising Compounds of Formula XV

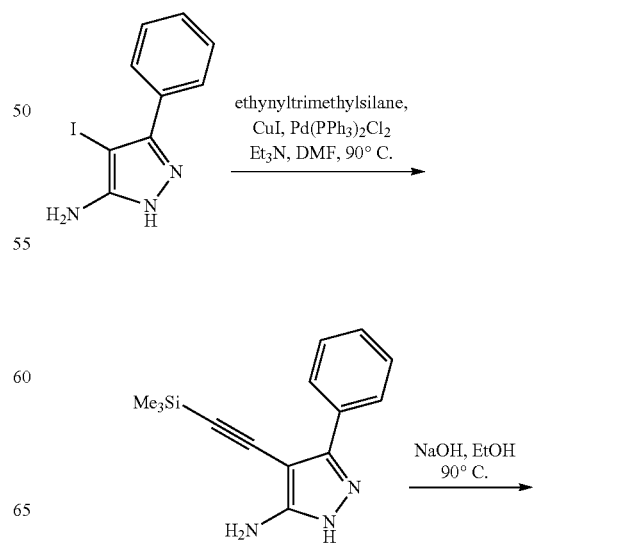

ethynyltrimethylsilane,
CuI, Pd(PPh$_3$)$_2$Cl$_2$
Et$_3$N, DMF, 90° C.

NaOH, EtOH
90° C.

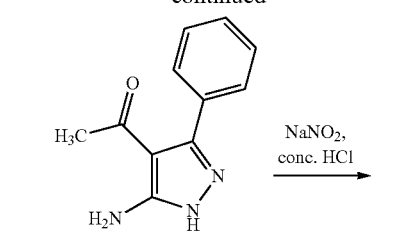
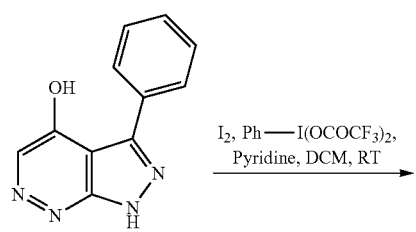
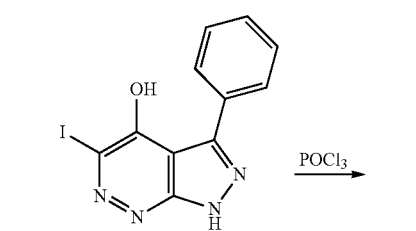
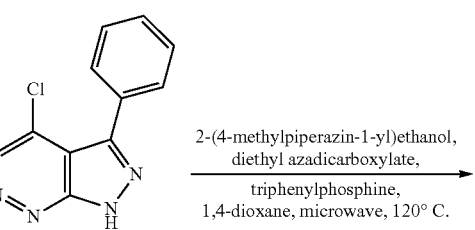
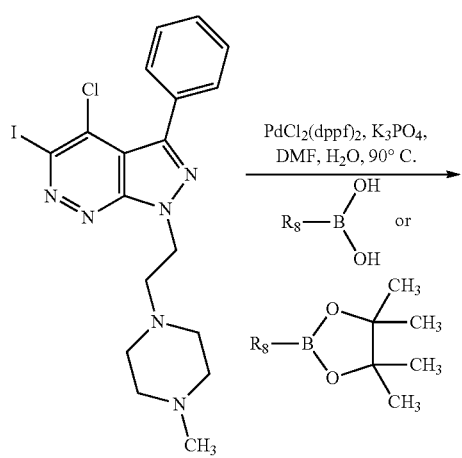
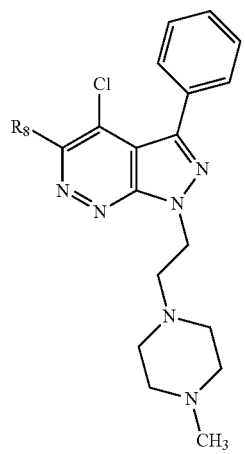
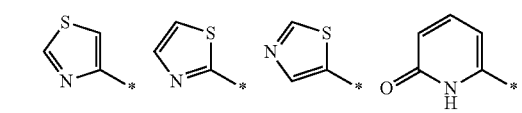
$R_8$ groups
Scheme VIII: Scheme for Synthesising Compounds 29-31 from Compound Ik:
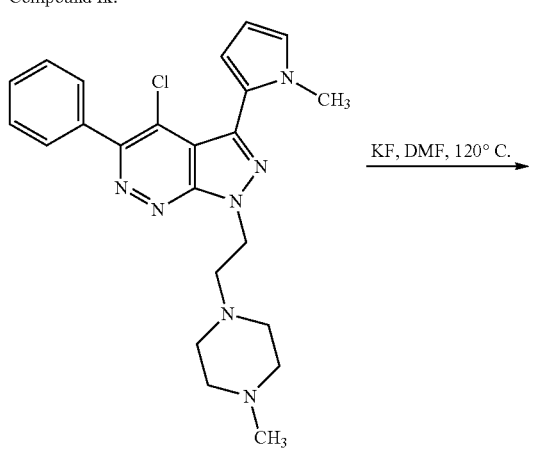

-continued

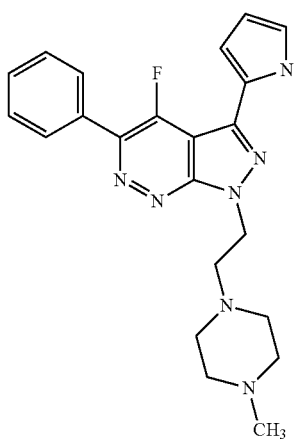

Compound 29

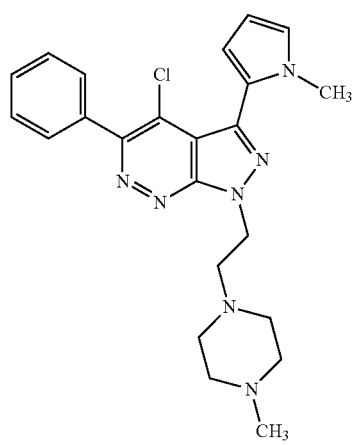

Compound 30

-continued

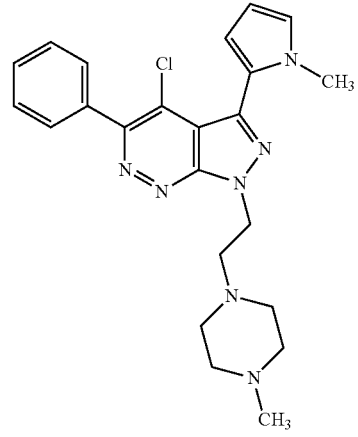

sodium methanesulfinate,
DMF, 60° C.
→

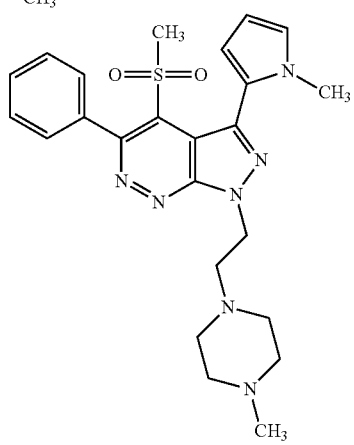

Compound 31

1. NaOH, DMSO
2. POBr₃
→

Example 78

Assay Method Showing Activity of Compounds of the Invention that Restore Expression of N48K Clarin-1 (24 Hour Incubation)

Clarin-1 is the protein encoded by the gene mutated in Usher III Syndrome (Adato et al., 2002). The most prevalent mutation in Clarin-1 in North America is N48K, which is reported to cause loss of glycosylation and a trafficking defect (Tian et al., 2009). As a consequence, the N48K protein does not reach the plasma membrane and is degraded by the proteasome. Thus it is believed that restoring the trafficking of N48K Clarin-1 to the cell surface provides an avenue of intervention for Usher III Sydrome.

A useful cellular model to demonstrate the utility of compounds of the invention that restore expression of N48K Clarin-1 is the HEK293-Clarin-1 N48K-HA D9 cell line (Tian et al., 2009). In a typical experiment, these cells were seeded on collagen-coated 96-well plates at a cell density of 20,000 cells per well in Dulbecco's Modified Eagle Medium (DMEM) contain 10% fetal bovine serum in a humidified incubator at 37° C., 5% $CO_2$. After an overnight incubation, compounds were added for a 24 hr incubation in DMEM medium contain 10% fetal bovine serum in a humidified incubator at 37° C., 5% $CO_2$. As a negative control, DMSO was used at 0.25% final concentrations. Compounds were typically tested in triplicate fashion. After the 24 hr incubation with compounds, the cells were fixed by the addition of 10% buffered formalin to the wells to achieve a final concentration of 4% formalin. After a 20 min fixation at room temperature, wells were washed three times with phosphate-buffered saline (PBS) containing Triton X-100 (0.02 phosphate, 150 mM NaCl, 0.1% Triton X-100).

The HA-tagged N48K Clarin-1 was detected with an antibody against the HA tag (HA. 11 Clone 16B12 Monoclonal antibody, Covance #MMS-101P) at a dilution of 1:1000 in PBS containing Triton X-100. After a 90 min incubation, wells were washed three times with PBS containing Triton X-100, and a secondary antibody (Goat anti-mouse IgG-Cy3 (1.5 mg/ml), Jackson IR Europe #115165003) was added to the wells at a dilution of 1:250 in PBS containing Triton X-100 for 45 min. Wells were subsequently washed three times with PBS containing Triton X-100, and a final staining for nuclei was performed by the addition of DAPI (4',6-diamidino-2-phenylindole) at a dilution of 1:10,000. The imaging of the stained cells was performed on an InCell 1000 High Content Imager (GE Healthcare), reading out the Cy3 channel for N48K Clarin-1 and the DAPI channel for nuclei. The images were analyzed and quantitated using a specific algorithm. This algorithm measured the HA-Clarin-1 staining for each cell based on the additional nuclear segmentation of the DAPI signal (FIG. 1). This algorithm measured the intensity per cell, and thus it is less sensitive for variation in cell number. Per well, approximately 2,000 cells were measured to achieve an average density per cell measurement.

Example 79

An Assay Method Showing Activity of Compounds of the Invention that Restore Expression of N48K Clarin-1 (2 Hour Incubation)

Clarin-1 is the protein encoded by the gene mutated in Usher III Syndrome (Adato et al., 2002). The most prevalent mutation in Clarin-1 in North America is N48K, which is reported to cause loss of glycosylation and a trafficking defect (Tian et al., 2009). As a consequence, the N48K protein does not reach the plasma membrane and is degraded by the proteasome. Thus it is believed that restoring the trafficking of N48K Clarin-1 to the cell surface provides an avenue of intervention for Usher III Sydrome.

A useful cellular model to demonstrate the utility of compounds of the invention that restore expression of N48K Clarin-1 is the HEK293-Clarin-1 N48K-HA D9 cell line (Tian et al., 2009). In a typical experiment, these cells were seeded on collagen-coated 96-well plates at a cell density of 20,000 cells per well in Dulbecco's Modified Eagle Medium (DMEM) contain 10% fetal bovine serum in a humidified incubator at 37° C., 5% $CO_2$. After an overnight incubation, compounds were added for a 2 hr incubation in DMEM medium contain 10% fetal bovine serum in a humidified incubator at 37° C., 5% $CO_2$. As a negative control, DMSO was used at 0.25% final concentrations. Compounds were typically tested in triplicate fashion. After the 2 hr incubation with compounds, the cells were incubated in fresh medium for 22 hr. The cells were then fixed by the addition of 10% buffered formalin to the wells to achieve a final concentration of 4% formalin. After a 20 min fixation at room temperature, wells were washed three times with phosphate-buffered saline (PBS) containing Triton X-100 (0.02 phosphate, 150 mM NaCl, 0.1% Triton X-100).

The HA-tagged N48K Clarin-1 was detected with an antibody against the HA tag (HA.11 Clone 16B12 Monoclonal antibody, Covance #MMS-101P) at a dilution of 1:1000 in PBS containing Triton X-100. After a 90 min incubation, wells were washed three times with PBS containing Triton X-100, and a secondary antibody (Goat anti-mouse IgG-Cy3 (1.5 mg/ml), Jackson IR Europe #115165003) was added to the wells at a dilution of 1:250 in PBS containing Triton X-100 for 45 min. Wells were subsequently washed three times with PBS containing Triton X-100, and a final staining for nuclei was performed by the addition of DAPI (4',6-diamidino-2-phenylindole) at a dilution of 1:10,000. The imaging of the stained cells was performed on an InCell 1000 High Content Imager (GE Healthcare), reading out the Cy3 channel for N48K Clarin-1 and the DAPI channel for nuclei. The images are analyzed and quantitated using a specific algorithm. This algorithm measured the HA-Clarin-1 staining for each cell based on the additional nuclear segmentation of the DAPI signal (FIG. 1). This algorithm measured the intensity per cell, and thus it is less sensitive for variation in cell number. Per well, approximately 2,000 cells were measured to achieve an average density per cell measurement.

Example 80

$IC_{50}$ Data for Illustrative Compounds of the Invention $IC_{50}$ values for illustrative Pyrazolopyridazine compounds of the invention were obtained according to the assay method of Example 77. Results are show below in Table 1.

TABLE 1

| Compound | $IC_{50}$* |
|---|---|
| Ia | A |
| Ib | C |
| Ic | A |
| Id | A |
| Ie | A |
| If | A |
| Ig | A |
| Ih | B |
| Ii | A |
| Ij | A |
| Ik | A |
| Il | A |
| Im | A |
| In | A |
| Iu | B |
| Iv | A |
| Iw | B |
| Iaa | B |
| Ibb | B |
| Idd | A |
| Iee | B |
| Iff | A, B |
| Igg | B |
| Ihh | A |
| Iii | A |
| IIa | A |
| IIb | A |
| IIc | A |
| IId | A |
| IIe | A |
| IIf | A |
| IIg | A |
| IIh | A |
| IIi | A |
| IIj | A |
| IIk | A |
| IIl | A |
| IIm | A |
| IIn | A |
| IIo | A |
| IIp | A |
| IIq | A |
| IIr | A |

TABLE 1-continued

| Compound | IC$_{50}$* |
|---|---|
| IIs | A |
| IIIc | A |
| IIId | A |
| 20 | C |
| 21 | B |
| 22 | A |
| 23 | B |
| 24 | A |
| 25 | A |
| 26 | A |
| 27 | B |

*A = Less than or equal to 2 μM
B = Greater than 2 μM and less than or equal to 5 μM
C = Greater than 5 μM and less than or equal 21 μM IC$_{50}$ values for illustrative Pyrazolopyridazine compounds of the invention were obtained according to the assay method Example 79. Results are show below in Table 2.

TABLE 2

| Compound | IC$_{50}$** |
|---|---|
| Ic | E |
| Ii | D |
| Ik | D |
| Il | D |
| Io | D |
| Ip | E |
| Iq | E |
| Ir | D |
| Is | D |
| It | E |
| Ix | F |
| Iy | D |
| Iz | D |
| Icc | D |
| IIa | E |
| IIb | D |
| IIc | D |
| IIf | D |
| IIg | D |
| IIh | D |
| IIj | D |
| IIl | D |
| IIn | D |
| IIq | D |
| IIs | D |
| IIt | D |
| IIu | D |
| IIv | E |
| IIw | E |
| IIx | D |
| IIy | D |
| IIIa | E |
| IIIb | E |
| XIIIa | E |
| XIIIb | E |
| XIIIc | F |
| XIIId | E |
| XIVa | D |

**D = Less than or equal to 4 μM
E = Greater than 4 μM and less than or equal to 8 μM
F = Greater than 8 μM and less than or equal 12 μM Each reference disclosed in this application is incorporated by reference herein in its entirety.

What is claimed is:

1. A method for treating a retinal degenerative disease, comprising administering to a subject in need thereof an effective amount of a compound having the structure 22:

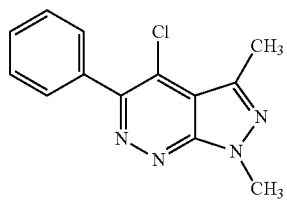 [SMILES: Cc1nn(C)c2nnc(-c3ccccc3)c(Cl)c12]

or 23:

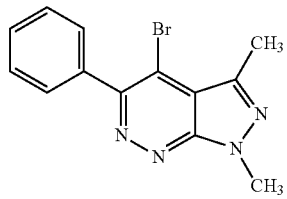 [SMILES: Cc1nn(C)c2nnc(-c3ccccc3)c(Br)c12]

or a pharmaceutically acceptable salt thereof.

2. A method for treating hearing loss associated with Usher syndrome, comprising administering to a subject in need thereof an effective amount of a compound having the structure 22:

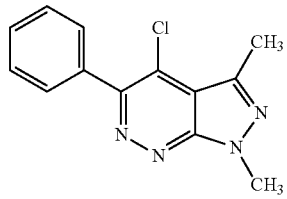 [SMILES: Cc1nn(C)c2nnc(-c3ccccc3)c(Cl)c12]

or 23:

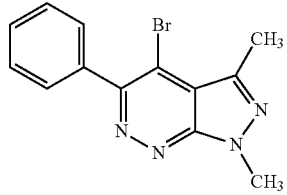 [SMILES: Cc1nn(C)c2nnc(-c3ccccc3)c(Br)c12]

or a pharmaceutically acceptable salt thereof.

* * * * *